United States Patent
El-Baz et al.

(10) Patent No.: US 11,238,975 B2
(45) Date of Patent: Feb. 1, 2022

(54) COMPUTER AIDED DIAGNOSIS SYSTEM FOR CLASSIFYING KIDNEYS

(71) Applicant: University of Louisville Research Foundation, Inc., Louisville, KY (US)

(72) Inventors: Ayman S. El-Baz, Louisville, KY (US); Amy Dwyer, Goshen, KY (US); Ahmed Soliman, Louisville, KY (US); Mohamed Shehata, Louisville, KY (US); Hisham Abdeltawab, Louisville, KY (US); Fahmi Khalifa, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 63 days.

(21) Appl. No.: 16/282,753

(22) Filed: Feb. 22, 2019

(65) Prior Publication Data
US 2019/0237186 A1    Aug. 1, 2019

Related U.S. Application Data

(63) Continuation-in-part of application No. 15/903,769, filed on Feb. 23, 2018, now Pat. No. 10,453,569.
(Continued)

(51) Int. Cl.
*G16H 30/40*    (2018.01)
*G06T 7/143*    (2017.01)
(Continued)

(52) U.S. Cl.
CPC .......... *G16H 30/40* (2018.01); *A61B 5/0261* (2013.01); *A61B 5/0295* (2013.01); *A61B 5/201* (2013.01);
(Continued)

(58) Field of Classification Search
CPC . G06T 2207/20081; G06T 2207/10088; G06T 7/0012; G06T 7/143; G06T 7/33;
(Continued)

(56) References Cited

U.S. PATENT DOCUMENTS

2004/0122790 A1* 6/2004 Walker ................. G16H 50/70
2005/0176057 A1* 8/2005 Bremer ................. G16B 20/50
                                                               435/6.16
(Continued)

OTHER PUBLICATIONS

Khalifa, Fahmi, et al. "Dynamic contrast-enhanced MRI-based early detection of acute renal transplant rejection." IEEE transactions on medical imaging 32.10 (2013): 1910-1927. (Year: 2013).*

(Continued)

*Primary Examiner* — Pinalben Patel
(74) *Attorney, Agent, or Firm* — Dentons Bingham Greenebaum LLP; Brian W. Chellgren

(57) ABSTRACT

A computer aided diagnostic system and automated method to classify a kidney utilizes medical image data and clinical biomarkers in evaluation of kidney function pre- and post-transplantation. The system receives image data from a medical scan that includes image data of a kidney, then segments kidney image data from other image data of the medical scan. The kidney is then classified by analyzing at least one feature determined from the kidney image data and the at least one clinical biomarker.

23 Claims, 29 Drawing Sheets
(10 of 29 Drawing Sheet(s) Filed in Color)

Related U.S. Application Data which is a continuation of application No. 14/676,111, filed on Apr. 1, 2015, now Pat. No. 9,928,347.

(60) Provisional application No. 62/633,917, filed on Feb. 22, 2018, provisional application No. 61/974,134, filed on Apr. 2, 2014.

(51) Int. Cl.

| | |
|---|---|
| *G06T 7/12* | (2017.01) |
| *G06T 7/33* | (2017.01) |
| *G06T 7/00* | (2017.01) |
| *G16H 30/20* | (2018.01) |
| *G16H 50/20* | (2018.01) |
| *A61B 5/20* | (2006.01) |
| *A61B 5/026* | (2006.01) |
| *A61B 5/00* | (2006.01) |
| *A61B 5/0295* | (2006.01) |
| *G16H 50/30* | (2018.01) |
| *A61B 5/145* | (2006.01) |

(52) U.S. Cl.
CPC .......... *A61B 5/4848* (2013.01); *A61B 5/7264* (2013.01); *G06T 7/0012* (2013.01); *G06T 7/12* (2017.01); *G06T 7/143* (2017.01); *G06T 7/33* (2017.01); *G16H 30/20* (2018.01); *G16H 50/20* (2018.01); *A61B 5/14546* (2013.01); *A61B 2505/05* (2013.01); *A61B 2576/02* (2013.01); *G06T 2207/10088* (2013.01); *G06T 2207/10096* (2013.01); *G06T 2207/20081* (2013.01); *G06T 2207/30084* (2013.01); *G16H 50/30* (2018.01)

(58) Field of Classification Search
CPC . G06T 2207/10096; G06T 2207/30084; G06T 7/12; G16H 30/40; G16H 50/30; G16H 30/20; G16H 50/20; A61B 5/201; A61B 5/14546; A61B 5/7264; A61B 5/0261; A61B 2576/02; A61B 2505/05; A61B 5/0295; A61B 5/4848
See application file for complete search history.

(56) References Cited

U.S. PATENT DOCUMENTS

| | | | | |
|---|---|---|---|---|
| 2005/0286768 | A1* | 12/2005 | Battle | G06K 9/3233 382/190 |
| 2008/0002870 | A1* | 1/2008 | Farag | G06K 9/6215 382/128 |
| 2009/0005693 | A1* | 1/2009 | Brauner | G06T 7/62 600/481 |
| 2013/0329973 | A1* | 12/2013 | Cao | A61B 5/0033 382/128 |

OTHER PUBLICATIONS

A. Kukla et al., "Ckd stage-to-stage progression in native and transplant kidney disease," Nephrology Dialysis Transplantation, vol. 23, No. 2, pp. 693-700, 2007.

E. Hollis et al., "Towards non-invasive diagnostic techniques for early detection of acute renal transplant rejection: A review," The Egyptian Journal of Radiology and Nuclear Medicine, vol. 48, No. 1, pp. 257-269, 2017.

F. Khalifa et al., "Models and methods for analyzing DCE-MRI: a review," Med. Phys., vol. 41, No. 12, pp. 1-32, 2014.

M. Abou-El-Ghar et al., "Role of diffusion-weighted MRI in diagnosis of acute renal allograft dysfunction: A prospective preliminary study," Br. J Radiol., vol. 85, No. 1014, pp. e206-e211, 2014.

G. Liu et al., "Detection of renal allograft rejection using blood oxygen level-dependent and diffusion weighted magnetic resonance imaging: A retrospective study," BMC Nephrol., vol. 15, No. 1, p. 158, 2014.

G. Myers et al., "Recommendations for improving serum creatinine measurement: A report from the laboratory working group of the national kidney disease education program," Clin. chem., vol. 52, No. 1, pp. 5-18, 2006.

A. Sharfuddin et al., "Renal relevant radiology: imaging in kidney transplantation," Clinical Journal of the American Society of Nephrology, vol. 9 No. 2, pp. 416-429, 2014.

E.D. Brown et al., "Complications of renal transplantation: Evaluation with US and radionuclide imaging," Radiograph., vol. 20, No. 3, pp. 607-622, 2000.

Z. Dostbil et al., "Comparison of split renal function measured by 99mT-c-DTPA, 99mTcMAG3 and 99mTc-DMSA rena scintigraphics in paediatric age groups," Clin. Reviews and Opinions, No. 2, pp. 20-25, 2011.

E. Giele, "Computer methods for semi-automatic MR renogram determination," Ph.D dissertation, Eindhoven University of Technology, Eindhoven, 2002.

A. Taylor and J.V. Nally, "Clinical applications of of renal scintigriphy," Am. J. Roentgenol, vol. 164, pp. 31-41, 1995.

J.G. Heaf and J. Iversen, "Uses and limitations of renal scintigraphy in renal transplantation monitoring," Eur. J. Nuc. Med., vol. 27, No. 7, pp. 871-879, 2000.

C. Sebastia et al., "Helical CT in renal transplantation: Normal findings and early and late complications," Radiograph, vol. 21, No. 5, pp. 1103-1117, 2001.

A. Grabner et al., Non-invasive diagnosis of acute renal allograft rejection-special focus on gamma scintigraphy and positron emission tomography. INTECH Open Access Publisher, 2013.

* cited by examiner

COMPUTER AIDED DIAGNOSIS SYSTEM FOR CLASSIFYING KIDNEYS

CROSS REFERENCE TO RELATED APPLICATION

This application is a continuation-in-part of U.S. application Ser. No. 15/903,769, entitled COMPUTER AIDED DIAGNOSTIC SYSTEM FOR CLASSIFYING KIDNEYS, filed Feb. 23, 2018, which is a continuation of U.S. application Ser. No. 14/676,111, entitled COMPUTER AIDED DIAGNOSTIC SYSTEM FOR CLASSIFYING KIDNEYS, filed Apr. 1,2015, which claims the benefit of U.S. Application No. 61/974,134, entitled COMPUTER AIDED DIAGNOSTIC SYSTEM FOR CLASSIFYING KIDNEYS, filed Apr. 2, 2014. This application further claims the benefit of U.S. Application No. 62/633,917, entitled NON-INVASIVE DIAGNOSIS PLATFORM FOR EVALUATING KIDNEY FUNCTION BY INTEGRATING CLINICAL-BIOMARKERS WITH MULTI-MODALITY MR IMAGE-MARKERS, filed Feb. 22, 2018. The contents of each of these related applications are hereby incorporated by reference in their entireties.

GOVERNMENT LICENSE RIGHTS

This invention was made with government support under grant number R15 AM 35924 awarded by the National Institutes of Health. The government has certain rights in the invention.

FIELD OF THE INVENTION

A computer aided diagnostic system and automated method to classify a kidney utilizes medical image data and clinical biomarkers in evaluation of kidney function pre- and post-transplantation. The system receives image data from a medical scan that includes image data of a kidney, then segments kidney image data from other image data of the medical scan. The kidney is then classified by analyzing at least one feature determined from the kidney image data and the at least one clinical biomarker.

BACKGROUND OF THE INVENTION

The kidney is the main filtration organ in the human body, keeping the nutrients that the body needs in and expelling the waste that can become toxic. Maintaining the health of this organ is very important. There are diseases that can cause the kidney to decrease in function such as diabetes, hypertension, glomerular disease, and polycystic kidney disease. These can result in a gradual loss of kidney function leading to waste build up in the body and cause the patient to develop chronic kidney disease (CKD). CKD affects about 26 million people and because only 17,000 transplants being performed each year in the U.S. and a limited number of donors, the assessment of a transplanted kidney is of critical importance to a clinician to ensure renal recovery. Though this has greatly improved the outcome of patients diagnosed with stage 5 CKD, complications can still arise. One of the main concerns is graft dysfunction. The immunological response of the patient to a transplanted kidney is referred to as acute rejection (AR) post-transplantation and is considered to be the leading cause of renal dysfunction after the transplantation. Early detection of renal dysfunction increases the survival rate of the transplanted kidney. Thus, calling for essential medical biomarkers to assess renal transplants is very necessary to distinguish the AR from other diagnoses, including acute tubular necrosis (ATN), tubular inflammation, acute tubular injury, graft amyloidosis, and immune drug toxicity, especially at an early stage (i.e. before major changes in creatinine clearance and serum plasma creatinine are detected). Traditional blood tests and urine sampling to evaluate renal transplant dysfunction cannot assess the function of individual kidneys.

The glomerular filtration rate (GFR) is often used since it is based on measuring the serum creatinine level and has been approved by the National Kidney Foundation to evaluate the overall kidney function. The GFR is a relatively imprecise and late indicator of renal dysfunction (significant changes in creatinine levels are only detectable after a 60% loss of renal function). Biopsy, which remains the gold standard for assessing renal transplant dysfunction, uses a relatively small needle to remove a small sample of tissue from the kidney. Biopsies are invasive, expensive, have a high morbidity rate, and may over- or under-estimate the extent of inflammation (an indicator of rejection) in the entire graft.

In addition to the GFR and the needle biopsy, several studies have investigated the ability of image-markers to assess renal transplant status. A quick overview of these imaging techniques is provided below and the reader is referred to A. Sharfuddin, "Renal relevant radiology: imaging in kidney transplantation," *Clinical Journal of the American Society of Nephrology*, vol. 9, no. 2, pp. 416-429, 2014, for more details about renal function assessment using diagnostic imaging. For example, scintigraphy (radionuclide) has been clinically used to qualitatively and quantitatively evaluate graft function. However, functional abnormalities inside different parts of the kidney (e.g., cortex and medulla) cannot be discriminated precisely due to scintigraphy's limited spatial resolution. Also, radionuclide imaging includes radiation exposure, thus limiting the range of its applications. Computed tomography (CT) is a commonly used imaging modality that allows an accurate evaluation of different renal transplant diseases. However, the contrast agents used are still nephrotoxic and the information gathered by CT to detect acute rejection (AR) is unspecific, thus limiting the CT role in AR diagnosis. The aforementioned shortcomings make those imaging techniques impractical for clinical use and has led to the use of alternative modalities (e.g., the ultrasound (US) and MRIs) to assess renal transplant functionality.

In contrast to radionuclides and CTs, US is a safer imaging technique for diagnosing kidney diseases. However, shadowing artifacts, low signal-to-noise ratios (SNRs), and speckles notably decrease the quality of US image and diagnostic confidence. Moreover, conventional US parameters are not exact indicators of renal graft dysfunction, and it can only provide a prognostic graft marker or even a similar indication like other diagnostic possibilities, such as ATN. These shortcomings have been circumvented recently by evaluating kidney functions with MRI, which allows advanced analysis of different aspects of renal function. Various MRI scan types are used to assess renal transplants. While some of MRI modalities only provide anatomical information, others provide anatomical and functional kidney information together (e.g., dynamic contrast-enhanced (DCE), diffusion-weighted (DW), and blood oxygen level dependent (BOLD) MRI).

Renal dynamic MRI is an emerging imaging technique for assessing kidney function. The technique is based on repeated imaging of the organ-of-interest before and after administration of a contrast-gent. FIG. 15 shows a typical example of DCE-MRI of the kidney. In recent years, several studies have exploited DCE-MRI to non-invasively analyze kidney function in both native and transplanted kidneys. This imaging modality has the ability to non-invasively characterize important functional parameters (e.g., renal blood flow (RBF), GFR, and renal plasma flow (RPF)) as well as tissue-specific functional changes. Recently, evaluation of kidney functions using dynamic contrast-enhanced magnetic resonance imaging (DCE-MRI) has been addressed in several studies. The ability to provide both anatomical and functional kidney information is the main advantage and reason for using DCE-MRI in kidney functions' evaluation.

On the other hand, DW-MRIs does not require intravenous contrast agents be delivered to the patient like DCE-MRI, which may induce nephrogenic systemic fibrosis. Therefore, DCE-MRI is preferably used only if the GFR>30 ml/min, otherwise, nephrologists recommend the use of DW-MRI. Thus, DW-MRI has been used an emerging imaging modality for renal function assessment, requires no radiation, while also providing both anatomical and physiological information. DW-MRI measures water molecules in soft tissues (e.g. kidney); when combined with the capillary perfusion and water diffusion, the apparent diffusion coefficients (ADC) can be quantified.

In addition to DCE-MRI and DW-MRI, another imaging technique, BOLD-MRI, has also been utilized to study renal rejection, using the amount of oxygen diffused blood in the kidney to examine the proper functionality of the kidney. Namely, the amount of deoxyhemoglobin is measured by the apparent relaxation rate (R2*) parameter.

Current studies utilizing DCE-MRI, DW-MRI, and BOLD-MRI to study renal rejection share some limitations. For example, their methods employ a manual delineation of the kidney using a 2D region of interest (ROI), which makes this delineation subjective. In addition, their methods are unable to compensate for the motion of the kidney since they did not account for the whole kidney. Furthermore, none of the aforementioned studies integrates both image- and clinical-based biomarkers to evaluate the kidney function. Moreover, the studies mentioned above did not investigate the fusion of multiple MR imaging modalities (e.g. DCE- and/or DW- with BOLD-MRI) to evaluate kidney function. Finally, none of these studies investigated neither the differentiation between AR and different renal disease (DRD) nor between the different AR types (e.g., T-cell mediated-rejection (TMR) or anti-body mediated-rejection (AMR)).

SUMMARY

The invention addresses these and other problems associated with the prior art by providing a computer aided diagnostic system and automated method for classifying a kidney by analyzing image data of an abdomen scan that includes image data for the kidney. Consistent with some embodiments of the invention, image data associated with an abdomen scan that includes image data of a kidney may be received. In some embodiments of the invention, the abdomen scan may comprise dynamic contrast-enhanced magnetic resonance imaging (DCE-MRI) data, diffusion-weighted magnetic resonance imaging (DW-MRI) data, blood oxygen level-dependent magnetic resonance imaging (BOLD-MRI) data and/or other such types of image data that may be collected for medical imaging. Moreover, the abdomen scan may generally comprise a plurality of time slice images (e.g., images of a time series), such that each time slice image generally corresponds to a particular time at which the image data was captured.

Kidney image data may be segmented from other image data of the abdomen scan, and one or more iso-contours of the kidney image data may be registered. In general, registering one or more iso-contours of the kidney image data may compensate for movement of the kidney across the plurality of time slices. Based on the one or more registered iso-contours, image data for a renal cortex of the kidney may be segmented from the kidney image data. Based on the renal cortex image data, the kidney may be classified as one of an acutely rejected transplant or a non-rejected transplant by analyzing at least one feature determined from the segmented renal cortex image data using a learned model associated with the at least one feature.

Consistent with further embodiments of the invention, a novel framework for the early assessment of kidney function integrates imaging markers that quantify the physiological status of the kidney (e.g., blood perfusion, water diffusion, bioavailability oxygenation) and clinical biomarkers that quantify renal function (e.g., serum plasma creatinine (SPCr) and creatinine clearance (CrCl)) using state-of-the-art deep-learning approaches in a computer-aided diagnostic system to enable accurate identification and classification of renal transplants without the need for renal biopsy. In some embodiments, the imaging markers are magnetic resonance imaging (MRI)-derived markers obtained from different imaging modalities (e.g., 3D dynamic contrast-enhanced (DCE-MRI) and/or 4D diffusion-weighted (DW-MRI) and 3D blood oxygen level dependent (Bold-MRI)). If the renal transplant was found abnormal, then the reason of the abnormality has to be determined to provide the proper treatment for the renal allograft. The abnormality of the renal allograft could happen because of the body refusal to the foreign transplanted organ known as acute rejection, which is one of the main barriers for renal allografts after transplantation, or it could be a different renal disease (DRD) (e.g., tubular inflammation, acute tubular injury, graft amyloidosis, etc.). Certain embodiments of the present invention are designed to help classify the different types of acute rejection (AR) post-transplantation into either T-cell mediated-rejection (TMR) or anti-body mediated-rejection (AMR). Certain embodiments of the present invention include five steps: (i) 3D kidney objects are segmented from adjacent abdomen structures with a level set-based deformable model approach that is guided by a stochastic speed relationship, which is based on an adaptive shape prior guided by the visual appearance of the DW-MRI data; (ii) a Laplace-based non-rigid registration approach is used to account for local deformations caused by physiological effects. Namely, the target kidney object is deformed over closed, equispaced surfaces (iso-surfaces) to closely match the reference object; (iii) estimated or calculated perfusion indices from DCE-MRI and/or diffusion indices from DW-MRI, and apparent relaxation rate from BOLD-MRI serve as MRI-derived markers for the detection of kidneys with abnormalities, DRD, assessment of kidney function, and classifying different AR types; (iv) the estimated MRI-derived markers are integrated with the clinical biomarkers (e.g., CrCl and SPCr) to provide discriminatory features for the detection of kidneys with abnormalities, DRD, and classification of AR types based on deep learning of a non-negative constrained stacked auto-encoders (SNCAEs) and; (v) color-maps depiction for kidneys with DRD are generated to provide the accurate assessment of kidney functionality of the diseased kidney and for visualization purposes to help radiologists identifying regions that need more attention from clinicians. In other embodiments, other visualization techniques may be used.

Preliminary results on a total of 66 1.5 T DW-MRI subjects (16 normal and 50 abnormal) to detect kidney transplants with abnormalities, using a SNCAE, have shown showed a 97% correct classification using leave-one-subject-out (LOSO) approach. In addition, initial results for discrimination of 50 abnormal kidney transplants (45 AR and 5 DRD) have shown a 95% accuracy as well. Moreover, the initial results to discriminate TMR from AMR on the 45 subjects diagnosed with AR have shown a 93% accuracy. Additionally, initial diagnostic results on a total of 373T DW-MRI subjects (16 normal and 21 abnormal) to detect kidney transplants with abnormalities, using a SNCAE, have shown showed a 95% correct classification using the same LOSO approach. In addition, initial results to discriminate the 21 abnormal kidney transplants (14 AR and 7 DRD) have shown a 90% accuracy. Moreover, initial results on the total of 50 DCE-MRI subjects (27 normal and 23 AR) to detect kidney transplants with abnormalities, using a SNCAE, have shown showed a 96% correct classification using the same LOSO approach. The present invention therefore shows promise as a reliable non-invasive diagnostic tool.

It will be appreciated that the various systems and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A better understanding of the present invention will be had upon reference to the following description in conjunction with the accompanying drawings.

DETAILED DESCRIPTION OF THE PREFERRED EMBODIMENTS

Embodiments consistent with the invention provide for automated classification of a kidney based on image analysis of at least a portion of the kidney that is in image data of a medical scan, such as an abdomen scan. Consistent with embodiments of the invention, a transplanted kidney may be classified as acutely rejected or non-rejected based at least on image analysis performed on a medical scan associated with the transplanted kidney. For example, embodiments of the invention may receive an abdomen scan that comprises a plurality of time sliced dynamic contrast-enhanced magnetic response imaging (DCE-MRI) data that includes kidney image data. Embodiments of the invention may analyze the kidney image data, and based on a learned model that classifies kidneys, the transplanted kidney may be classified based on one or more features determined from the analyzed kidney image data.

Further details are provided in [1] F. Khalifa, M. El-Ghar, B. Abdollahi, H. Frieboes, T. El-Diasty, and A El-Baz, "A Comprehensive Non-Invasive Framework for Automated Evaluation of Acute Rental Transplant Rejection Using DCE-MRf", NMR in Biomedicine, vol. 26, issue 11, pg. 1460-1470, November 2013; [2] F. Khalifa, G. Beache, M. ElGhar, T. El-Diasty, G. Gimel'farb, M. Kong, and A El-Baz, "Dynamic Contrast-Enhanced MRIBased Early Detection of Acute Renal Transplant Rejection", IEEE Transactions on Medical Imaging, vol. 32, issue 10, pg. 1910-1927, October 2013; [3]M. Shehata, F. Khalifa, A Soliman, R. Alrefai, M. A El-Ghar, A Dwyer, R. Ouseph, and A El-Baz, "A Novel Framework for Automatic Segmentation of Kidney from DW-MRI", IEEE International Symposium on Biomedical Imaging, Apr. 18, 2015; and [4] M. Shehata, F. Khalifa, A Soliman, M. A El-Ghar, A Dwyer, R. Ouseph, and A El-Baz, "4D Diffusion MRI-Based CAD System for Early Diagnosis of Acute Renal Rejection", MICCAI 2015, Berlin, Germany, October 2015, all of which are incorporated by reference in their entirety, and thus form a part of the instant disclosure.

Figure 1:
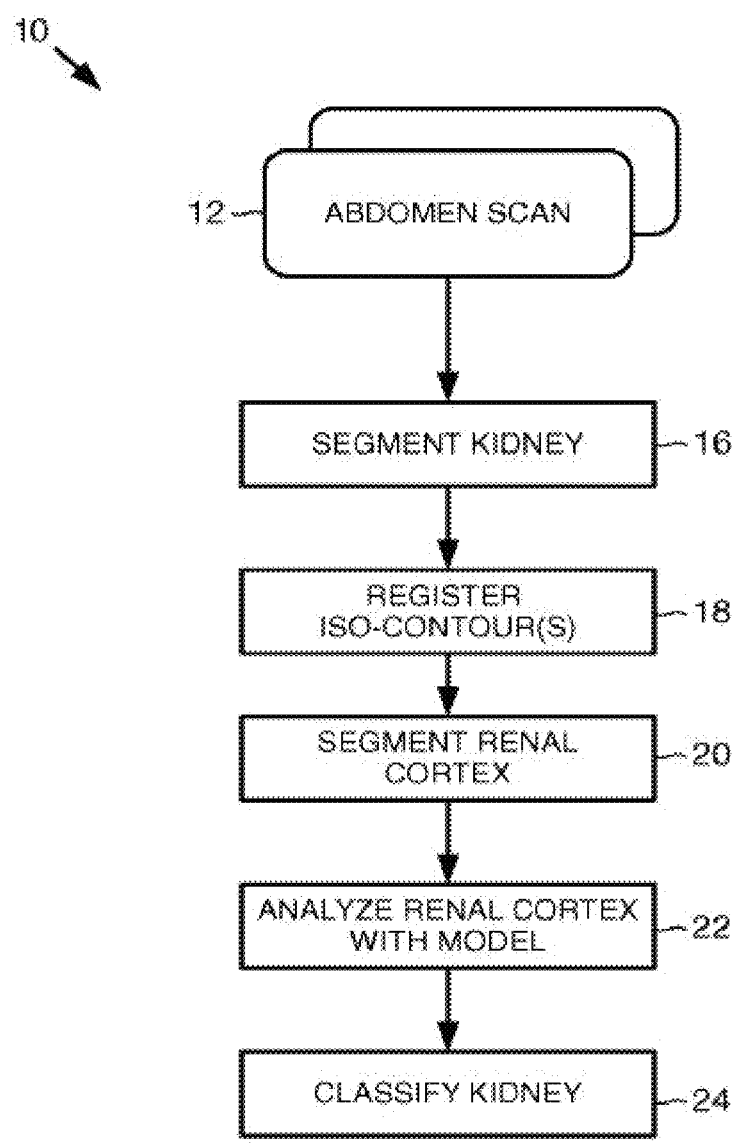
FIG. 1 is a flowchart of an automated kidney classification process.

Now turning to FIGS. 1-13, wherein like numbers denote like parts throughout the several views, FIG. 1 illustrates an exemplary automated process 10 classification of a kidney. Process 10 in particular is based upon the determination/classification of a transplanted kidney as acutely rejected or non-rejected. Process 10 receives as input one or more abdomen scans, and begins by segmenting kidney image data from the other image data of the one or more abdomen scans (block 16). In general, an abdomen scan may include one or more two dimensional "slices" of image data generated from a medical imaging device such as a CT scanner, an MRI imager, or other medical imaging device.

Once the kidney image data is segmented, one or more iso-contours may be used to register the kidney image data (block 18). In general, because a medical image scan may include a plurality of time sliced images, motion effects may be compensated for between the image frames of the plurality of time slices to thereby facilitate analysis of corresponding features across the time series. Therefore, consistent with embodiments of the invention, one or more iso-contours may be registered such that perfusion-related features are accurately identified and analyzed across the time series. Consistent with embodiments of the invention, the one or more iso-contours of the kidney image data may be registered based on geometric features of the kidney image data. For example, the one or more iso-contours of the kidney image data may be registered by using a Laplace partial differential equation to determine point-to-point correspondences between kidney objects to identify and register iso-contours across the time series of the kidney image data. Based on the registered kidney objects, renal cortex image data may be segmented from the kidney image data (block 20).

Following cortex segmentation, embodiments of the invention may determine one or more features associated with the kidney based on the renal cortex image data. Based on the one or more features, the renal cortex may be analyzed with one or more learned models associated with the one or more features (block 22). Generally, a learned model may be developed based on known training sets of classified transplanted kidneys and based on the one or more features determined for such classified transplanted kidneys. In some embodiments of the invention, perfusion values may be a feature that may be determined based on the renal cortex image data. For example, perfusion values for a transplanted kidney may be determined based at least in part on signal intensity versus time curves for at least a portion of the kidney image data, including for example, at least a portion of the renal cortex image data. Moreover, to compensate for various other physiological characteristics of patients, some embodiments of the invention may normalize the one or more determined features based at least in part on a corresponding feature for a segment of image data not associated with the kidney, such as a segment of image data corresponding to a body wall muscle proximate the kidney.

After analyzing the renal cortex image data with the learned model, including for example, analyzing the one or more determined features with the learned model, embodiments of the invention may classify the kidney associated with the received abdominal scan (block 24). Therefore, consistent with some embodiments of the invention, a kidney may be classified and/or evaluated. In particular, in some embodiments, a transplanted kidney may be classified as acutely rejected or non-rejected—i.e., the success of a kidney transplant may be evaluated.

Figure 2:
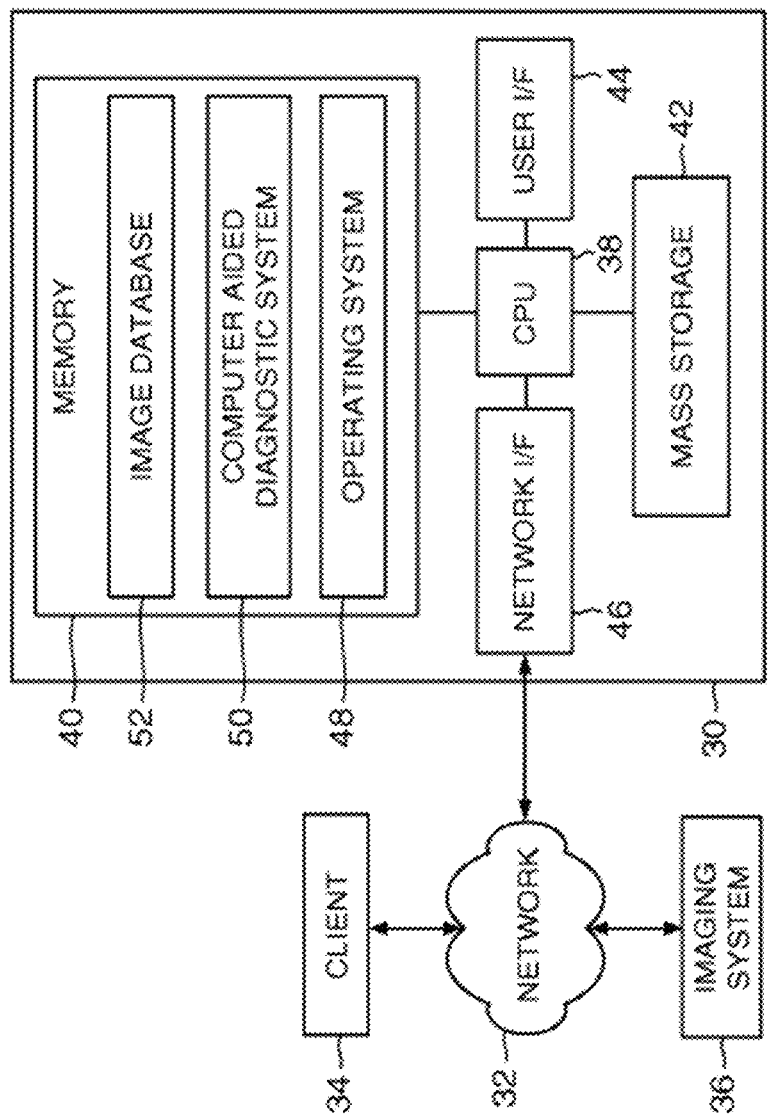
FIG. 2 is a block diagram of an exemplary apparatus suitable for implementing steps from the process of FIG. 1.

One or more steps in process 10 may be implemented in an automated fashion, utilizing a computer or other electronic device to implement such steps. FIG. 2, for example, illustrates an exemplary apparatus 30 within which various steps from process 10 may be implemented in a manner consistent with the invention. Apparatus 30 in the illustrated embodiment is implemented as a server or multi-user computer that is coupled via a network 32 to one or more client computers 34, as well as an imaging system 36, e.g., a two dimensional dynamic contrast-enhanced magnetic resonance imaging device, a helical or multi-slice LDCT scanner, etc. For the purposes of the invention, each computer 30, 34 may represent practically any type of computer, computer system, data processing system or other programmable electronic device. Moreover, each computer 30, 34 may be implemented using one or more networked computers, e.g., in a cluster or other distributed computing system. In the alternative, computer 30 may be implemented within a single computer or other programmable electronic device, e.g., a desktop computer, a laptop computer, a handheld computer, a cell phone, a set top box, etc.

Computer 30 typically includes a central processing unit 38 including at least one microprocessor coupled to a memory 40, which may represent the random access memory (RAM) devices comprising the main storage of computer 30, as well as any supplemental levels of memory, e.g., cache memories, non-volatile or backup memories (e.g., programmable or flash memories), read-only memories, etc. In addition, memory 40 may be considered to include memory storage physically located elsewhere in computer 30, e.g., any cache memory in a processor in CPU 38, as well as any storage capacity used as a virtual memory, e.g., as stored on a mass storage device 42 or on another computer coupled to computer 30. Computer 30 also typically receives a number of inputs and outputs for communicating information externally. For interface with a user or operator, computer 30 typically includes a user interface 44 incorporating one or more user input devices (e.g., a keyboard, a mouse, a trackball, a joystick, a touch pad, and/or a microphone, among others) and a display (e.g., a CRT monitor, an LCD display panel, and/or a speaker, among others). Otherwise, user input may be received via another computer or terminal.

For additional storage, computer 30 may also include one or more mass storage devices 42, e.g., a floppy or other removable disk drive, a hard disk drive, a direct access storage device (DASD), an optical drive (e.g., a CD drive, a DVD drive, etc.), and/or a tape drive, among others.

Furthermore, computer 30 may include an interface 46 with one or more networks 32 (e.g., a LAN, a WAN, a wireless network, and/or the Internet, among others) to permit the communication of information with other computers and electronic devices. It should be appreciated that computer 30 typically includes suitable analog and/or digital interfaces between CPU 36 and each of components 40, 42, 44 and 46 as is well known in the art. Other hardware environments are contemplated within the context of the invention.

Computer 30 operates under the control of an operating system 48 and executes or otherwise relies upon various computer software applications, components, programs, objects, modules, data structures, etc., as will be described in greater detail below. Moreover, various applications, components, programs, objects, modules, etc. may also execute on one or more processors in another computer coupled to computer 30 via network 32, e.g., in a distributed or client-server computing environment, whereby the processing required to implement the functions of a computer program may be allocated to multiple computers over a network.

As an example, computer 30 may include a computer aided diagnostic (CAD) system program 50 used to implement one or more of the steps described above in connection with process 10. For the purposes of implementing such steps, an image database 52, storing medical image scans, may be implemented in computer 30. It will be appreciated, however, that some steps in process 10 may be performed manually and with or without the use of computer 30.

In general, dynamic magnetic resonance imaging time series (i.e., DCE-MRI image data) may be subject to relatively low signal-to-noise, non-uniform intensity distribution over a time series of the image data, which may be due to respiratory and physiological motion. Hence, accurate segmentation of image data for a kidney may be challenging. Embodiments of the invention may generate deformable prototypes with level sets that may provide flexible evolution on an xy-plane with no need for parameterization. A level set function 0 may correspond to a distance map of signed minimal Euclidian distances from every point (x, y) of the plane to the boundary (negative for interior points and positive for exterior points). Generally, the level set function evolves in the discrete time-space domain according to the following equation:

$$\emptyset_{n+1}(x, y) = \emptyset_n(x, y) - \tau F_n(x, y) \mid \nabla \emptyset_n(x, y) \mid, \qquad (1)$$

where $n$ is a discrete instant of time $t = n\tau$ taken with a step $\tau > 0$, $F_n(x, y)$ is a speed function controlling evolution, and $\nabla \emptyset_n(x, y) = \left[ \dfrac{\partial \emptyset_n}{\partial x}, \dfrac{\partial \emptyset_n}{\partial v} \right]$ corresponds to a gradient of $\emptyset_n(x, y)$ For segmentation of image data, embodiments may implement a stochastic speed function that may depend on at least three features: a weighted probabilistic shape prior, pixelwise image intensities, and high-order spatial interactions. The features may be integrated into a joint, bi-level, probabilistic Markov-Gibbs random field (MGRF) model of the kidney and its background. A probabilistic MGRF model of the kidney and background may be described by the following equations:

$$R = \{(x,y): 0 \le x \le X-1, 0 \le y \le Y-1\}, \qquad (2)$$

where R denotes a finite arithmetic lattice of the size XY supporting grayscale images and their region segmentation maps;

$$Q=\{0, 1, \ldots, Q-1\} \quad (3)$$

denotes a finite set of Q integer gray values;

$$L=\{0,1\}, \quad (4)$$

denotes a binary set of object ("1") and background ("0") labels;

$$g=\{g_{x,y}:(x,y)\in R; g_{x,y}\in Q\} \quad (5)$$

is a grayscale image taking values from Q (i.e., g:R→Q); and $$m=\{m_{x,y}:(x,y)\in R; m_{x,y}\in L\} \quad (6)$$

is a region map taking values from L (i.e., m: R→L).

An input image g of the image data may be co-aligned to a shape prior model, and a region map m of the input image may be described with a joint probability model provided by the following equation:

$$P(g,m)=P(g|m)P(m), \quad (7)$$

where P(g|m) is a conditional distribution of the images given the map;

$$P(g,m)=P_s(m)P_V(m) \quad (8)$$

is an unconditional probability distribution of maps;
$P_s(m)$ denotes a weighed shape prior model, and
$P_V(m)$ is a Gibbs probability distribution with potentials V, which specifies a MGRF model of spatially homogenous maps m.

Figure 3:
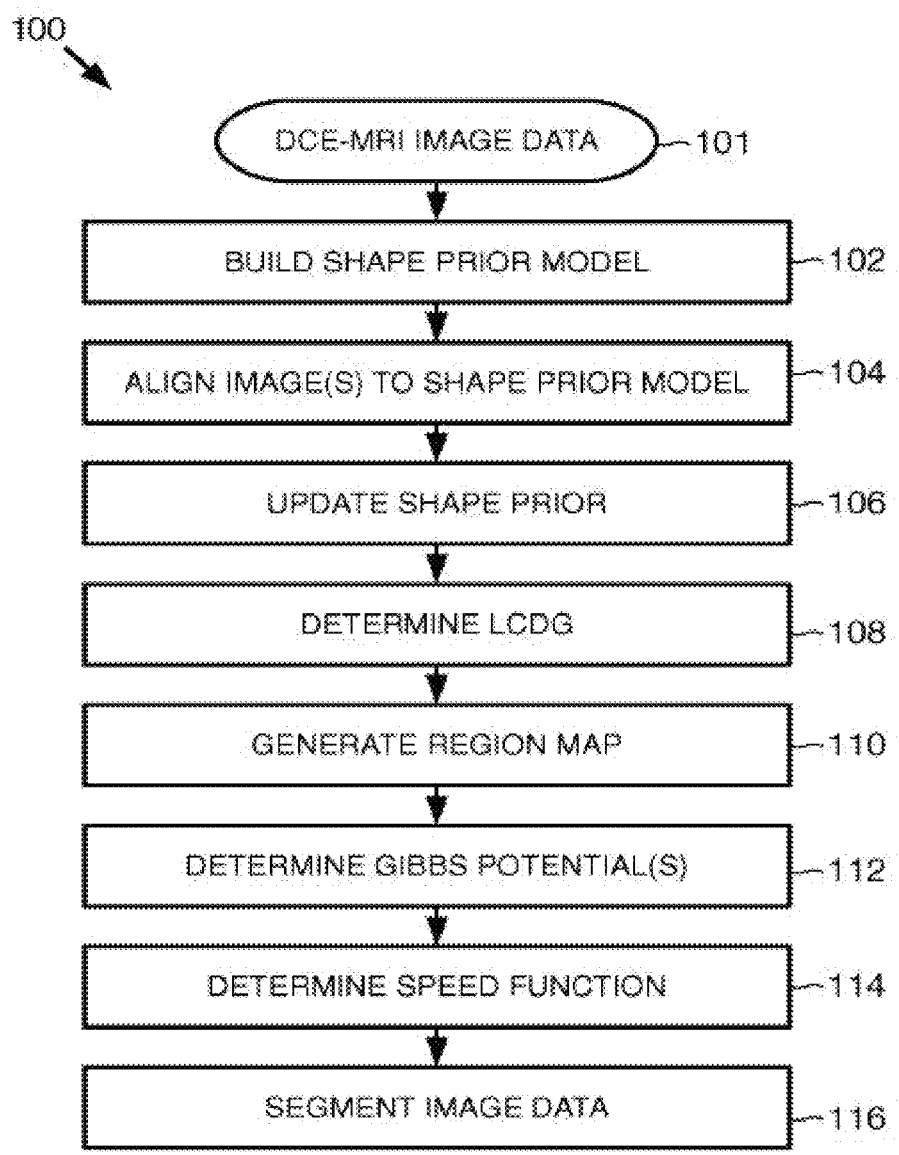
FIG. 3 is a flowchart that illustrates a sequence of operations that may be performed by the computer of FIG. 2.

FIG. 3 provides a flowchart 100 that illustrates a sequence of operations that may be performed by the computer 30 to segment each image received in image data 101 for one or more DCE-MRI scans consistent with embodiments of the invention. As shown, the computer 30 may build a shape prior model that is based on training sets of image data of kidneys (block 102). Generally, embodiments of the invention may implement a level set evolution using an adaptive shape prior of the kidney that may be built for a set of training images, which may be collected from different subjects. Variability of shapes may be reduced to obtain more accurate segmentation by mutually co-aligning training images with a two-dimensional affine transformation, which generally maximizes mutual information for the training images. A shape prior model may be generated based at least in part on training images in which kidney borders have been identified, where the training images may specify region maps for co-aligned training images. A shape prior model may be generated as a spatially variant independent random field of region labels in the following maps:

$$P_s(m)=\Pi_{(x,y)\in R}p_{s:x,y}(m_{x,y}), \quad (9)$$

where $p_{s:x,y}(1)$, and $p_{s:x,y}(0)=1-p_{S:x,y}(1)$,
and correspond to the empirical pixel—wise probabilities of kidney and background.

The computer 30 may align images of the image data to the shape prior model (block 104). Each input image of image data to be segmented may be co-aligned to at least one training image. The computer 30 may update the shape prior based at least in part on the co-aligned images and the shape prior model (block 106). Consistent with embodiments of the invention, normalized cross-correlation (NCC) values (i.e., 1Jj;j=1, . . . , N) between the co-aligned input image and each of the N training images may be determined. A weighted sum of the training region maps may be computed for the aligned images, and the shape prior model may be updated based at least in part on the weighted sums. A pixel-wise kidney probability (i.e., Ps:x,y(1)) may be determined based at least in part on a weighted sum of occurrences of the pixel (x, y) in the kidney region in all training maps based at least in part on the following equation:

$$p_{s:x,y}(1) = \frac{1}{a}\sum_{j=1}^{N} \eta_j m_{j:x,y}, \text{ where } a = \sum_{j=1}^{N} \eta_j. \quad (10)$$

Based on the aligned images the updated shape prior model, the computer 30 determines a linear combination of discrete Gaussians (LCDG) (block 108). In general, to account for inhomogeneity of a kidney (e.g., cortex and medulla), high-order pair-wise spatial interactions between region labels of a map m may be added. Particularly, triple and quad cliques may be added. If $C_a$ denotes a family of s-order cliques of an interaction graph with nodes in the lattice sites (x, y) and edges connecting the interacting, or interdependent, sites, large variations of DCE-MRI based image data related to transit of contrast agent, label interactions may be modeled by a spatially homogenous MGRF with up to fourth-order interactions over a nearest eight neighborhood of pixels based on the following equation:

$$P_V(m) = \frac{1^{(\Sigma_{a=1}^{A} \Sigma_{c\in C_a} V_a(m(x,y):(x,y)\in c))}}{Z_V}, \quad (11)$$

where A clique families describe the geometry of interactions;
$V=[V_a \{0,1\}\to(-\infty,\infty):a=1, \ldots, A]$ is a collection of Gibbs potential functions $V_a$ for the families $C_a$, and the partition function $Z_V$ normalizes the probabilities over the parent population $\mathbb{M}=\{0,1\}^{XY}$ of all the maps.

Based on the LCDGs, the computer 30 may determine a region map that identifies pixels corresponding to the kidney and pixels corresponding to background (block 110). In general, an initial region map m may be determined by pixel-wise classification, and such initial region map may facilitate determination of maximum likelihoods of potentials and determination of pixel-wise probabilities of region labels at each step of a contour evolution. Consistent with some embodiments, equality or inequality of labels may be evaluated for a clique c, such that corresponding second-order potentials may correspond to the following equations:

$$V_a(m(x_1,y_1),m(x_2,y_2))=V_{2:a:eq} \quad (12)$$

if $m((x_1\ y_1)=m(x_2,y_2)$,
otherwise $V_a(m(x_1,y_1),m(x_2,y_2))=-V_{2:a:eq}$.
Third-order potentials may correspond to the following equation:

$$V_a(m(x_1,y_1),m(x_2,y_2),m(x_3,y_3))=V_{3:a:eq_3} \quad (13)$$

if $m(x_1,y_1)=m(x_2,y_2)=m(x_3,y_3)$,
otherwise $V_a(m(x_1,y_1),m(x_2,y_2),m(x_3,y_3))=-V_{3:a:eq_3}$.
Fourth-order potentials may correspond to the following equation:

$$V_a(m(x_1,y_1),m(x_2,y_2),m(x_3,y_3),m(x_4,y_4))=V_{4:a:eq_j} \quad (14)$$

if there are j=4 or j=3 equal labels, otherwise $$V_a(m(x_1,y_1),m(x_2,y_2),m(x_3,y_3),m(x_4,y_4))=-(V_{4:a:eq_3}+V_{4:a:eq_4}).$$

The computer may determine Gibbs potentials for the fourth-order MGRF model of the region map m (block 112). The determined Gibbs potentials from a given map m, i.e., the determination of the values $V_{2:a:eq}$, $V_{3:\ a:eq3}$, $V_{4:\ a:\ eq3}$, and $V_{4:a:eq4}$ may be implemented to extend second-order MGRF models to higher-order MGRF models.

A visual appearance of a kidney region and surrounding tissue (i.e., background) in an image may be modeled by separating a mixed empirical marginal one dimensional distribution of pixel intensities into two individual components corresponding to a dominant kidney and background modes. The empirical distribution may be approximated with a linear combination of LCDG and automatically separated into kidney and its background components to form LCDG models. Additional details regarding the determination of Gibbs potentials may be found, for example, in the incorporated description material [2].

LCDG models may be determined based at least in part on the following equation:

$$\Psi_\theta = (\psi(q|\theta) : q \in Q) \qquad (15)$$

denotes a discrete Gaussian with parameters $\theta=(\mu,\sigma)$.

A continuous one-dimensional Gaussian density with the mean $\mu$ and the variance $\sigma^2$ may be integrated over successive gray level intervals. A particular LCDG with two dominant positive discrete Gaussians and $C_p \geq 2$ positive and $C_n \geq 0$ negative subordinate discrete Gaussians may be defined by the following equation:

$$P_{w,\theta}(q) = \Sigma_{k=1}^{C_p} \omega_{p:k} \psi(q|\theta_{p:k}) - \Sigma_{k=1}^{C_n} \omega_{n:k} \psi(q|\theta_{p:k}), \qquad (16)$$

where weights $W=[w_{p:k}, w_{n:k}]$ are non-negative and meet an obvious constraint $\Sigma_{k=1}^{C_p} w_{p:k} - \Sigma_{k=1}^{C_n} w_{n:k} = 1$.

All LCDG parameters, including a number of discrete Gaussians, may be determined from a mixed empirical distribution to be modeled. The distribution and its components may be modeled with LCDGs more accurately that with a model including only positive discrete Gaussians or other such unimodal distributions associated with each component.

With the weighted probabilistic shape prior, pixel-wise image intensities, and higher-order spatial interaction terms, embodiments of the invention may facilitate pixel-wise guidance of the level set. In general, p(q|l) denotes the pixel-wise probability of the intensity $q \in Q$ of the LCDG model of a kidney (l=1) or background (l=O) appearance, and $pv_{:x,y}(1)$ corresponds to the probability of the kidney label for the pixel (x, y) of the region map m in the MGRF model $P_v(m)$ at the current evolution step. The computer may analyze the Gibbs potentials of the MGRF model based at least in part on the following equations:

$$\text{Let } P_{1:x,y} = \frac{\Omega_{1:x,y}}{\Omega_{1:x,y} + \Omega_{0:x,y}} \text{ and} \qquad (17)$$

$$P_{0:x,y} = \frac{\Omega_{1:x,y}}{\Omega_{2:x,y} + \Omega_{0:x,y}} = 1 - P_{1:x,y},$$

where $\Omega_{1:x,y} = |p(q|1)p_{V:x,y}(1)p_{S:x,y}(1)$, and $\Omega_{0:x,y} = p(q|0)(1 - p_{V:x,y}(1))(1 - p_{S:x,y}(1))$ Then, the speed function of equation (1) may be defined as the following equation:

$$F(x,y) = \kappa d(x,y), \qquad (18)$$

where $\kappa$ corresponds to a mean contour curvature and $\vartheta(x,y)$ corresponds to a magnitude and direction of contour evolution at the point (x,y) and $$v(x, y) = \begin{cases} -P_{1:x,y} & \text{if } P_{1:x,y} > P_{0:x,y} \\ P_{0:x,y} & \text{otherwise} \end{cases}.$$

The computer determines a speed function (block 114) for the image data, where the speed function may be used to compensate for motion over a time series of images of the image data. The computer 30 segments the image data (block 116) by evolving the level set function 0 guided by the speed function. As will be appreciated, the segmented image data comprises image data of each image determined to correspond to a kidney based on the process described above such that image data corresponding to background is removed.

Figure 4A:
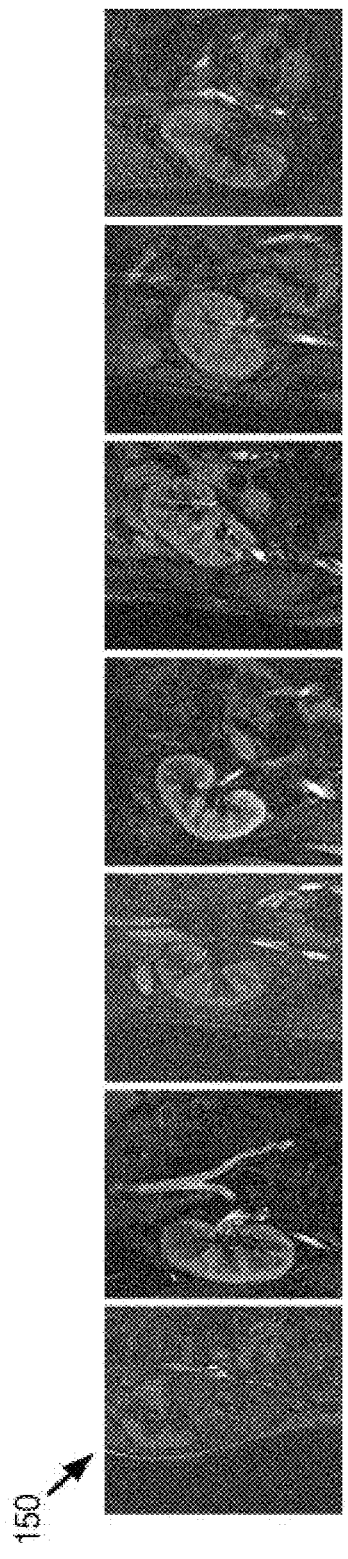
FIGS. 4A, 4B, and 4C provide diagrammatic illustrations of kidney image data and segmented kidney image data that may be processed by the computer of FIG. 2 to build a kidney shape prior model.
Figure 4B:
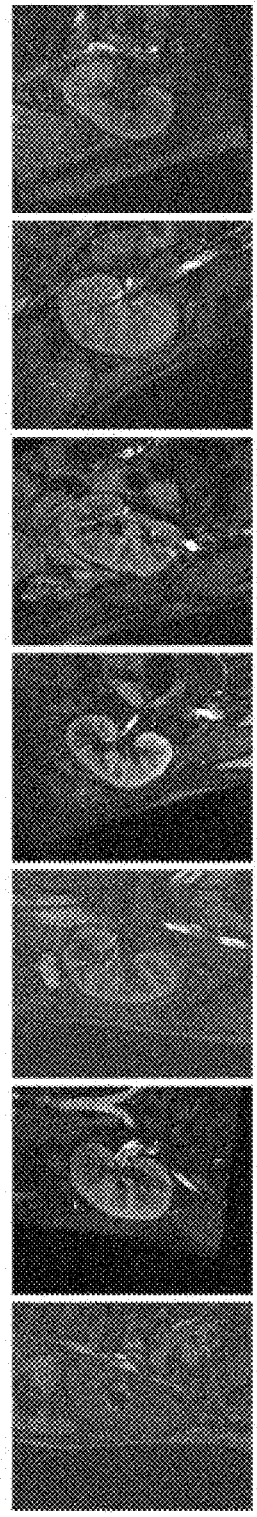
Figure 4C:
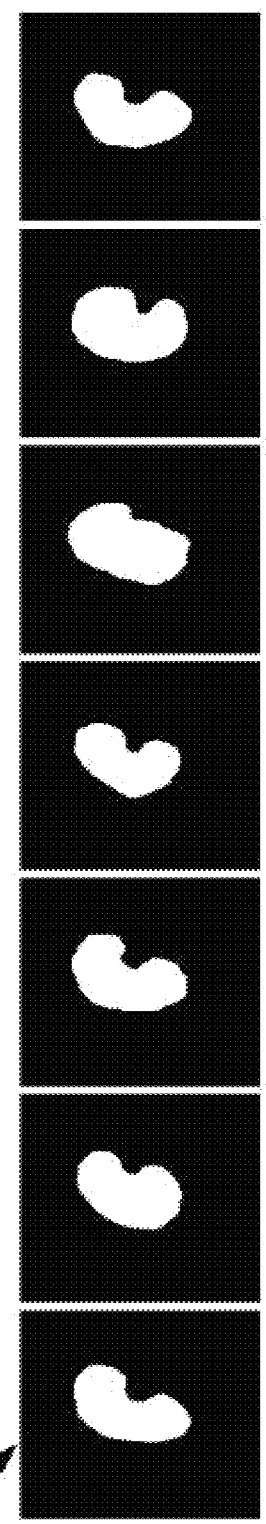
Figure 5:
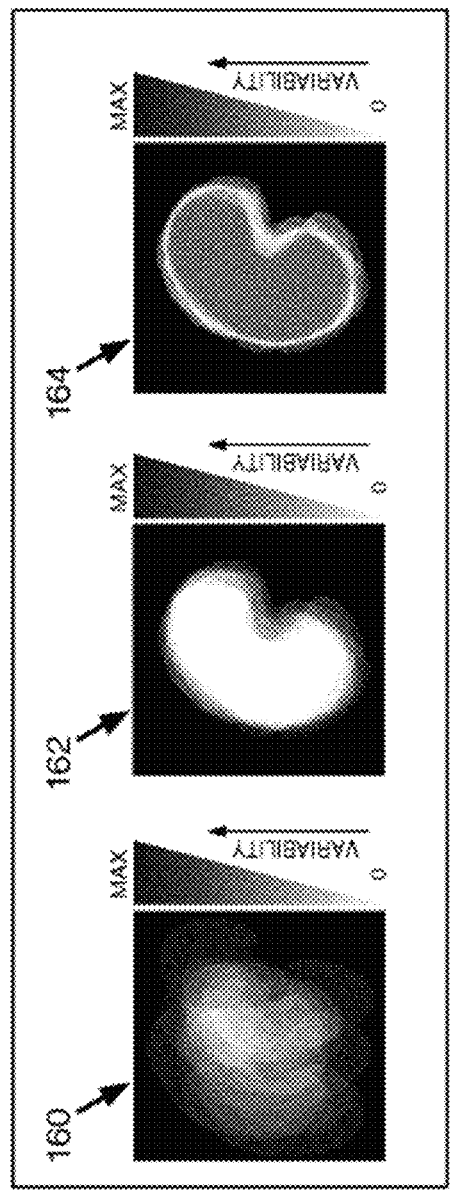
FIG. 5 provides a diagrammatic illustration of kidney shape prior image data that may be processed by the computer of FIG. 2.
Figure 6:
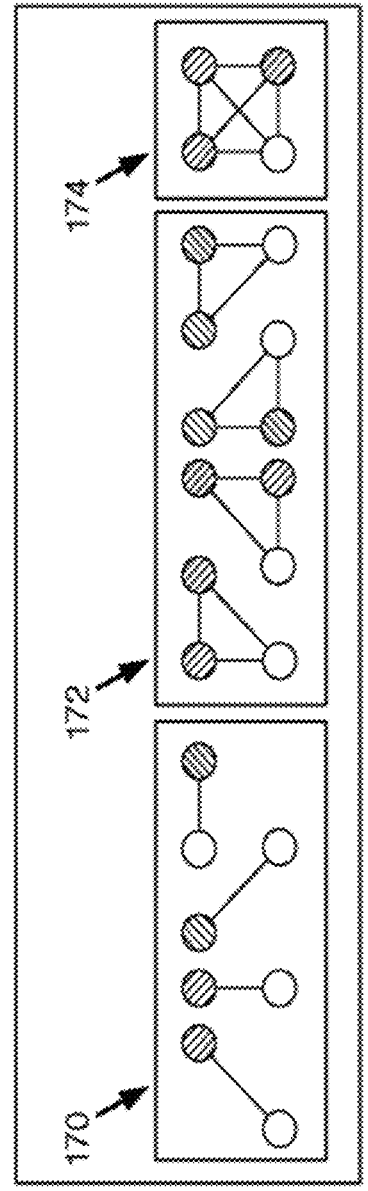
FIG. 6 provides a diagrammatic illustration of example pixel-wise neighborhoods that may be implemented by the computer of FIG. 2 to process image data.

FIGS. 4A-C provide diagrammatic illustrations of image data including images of kidneys that may be segmented consistent with some embodiments. FIG. 4A provides example images of kidneys 150 that may be received as image data consistent with some embodiments of the invention. FIG. 4B illustrates an example affine based alignment data 152 of the images 150 of FIG. 4A. FIG. 4C illustrates example segmented image data 154 that may be determined from the images 150 of FIG. 4A. As will be appreciated, in some embodiments, the images of kidneys 150, the aligned data 152, and the segmented image data 154 may be used to generate a shape prior model. FIG. 5 illustrates example images of kidneys 160 prior to alignment, after affine based registration 162, and a grayscale visualization of a shape prior model 164 generated by analysis and alignment of the example images of kidneys 160. FIG. 6 provides a diagrammatic illustration that illustrates example second-order cliques 170, third-order cliques 172, and fourth-order cliques 174 for a nearest 8-pixel neighborhood.

After affine registration and kidney segmentation, non-rigid registration may be performed to compensate for local kidney motion and/or deformations over a time of the image acquisition for the images of the image data. Consistent with some embodiments of the invention, geometric features of the segmented image data may be used to perform registration of the segmented image data, which may overcome problems associated with intensity variations associated with the temporal dynamic contrast data set of DCE-MRI image data. Solutions for a Laplace partial differential equation may facilitate determining point-to-point correspondences between nested equi-spaced iso-contours in target and reference segmented image data and kidney objects of the segmented image data.

Figure 7:
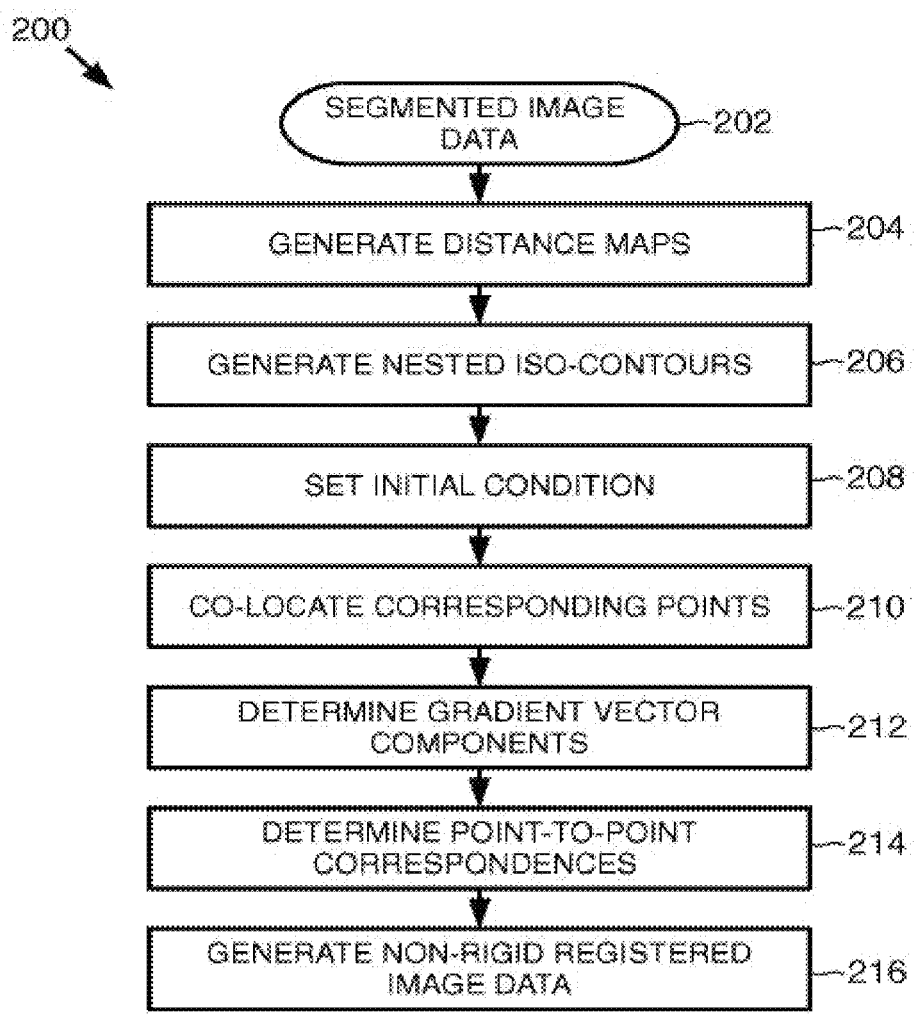
FIG. 7 is a flowchart that illustrates a sequence of operations that may be performed by the computer of FIG. 2.

FIG. 7 provides a flowchart 200 that illustrates sequence of operations that may be performed by the computer 30 to thereby perform iso-contours based nonrigid registration for segmented image data 202 consistent with embodiments of the invention. The computer 30 may analyze the segmented image data to generate distance maps (block 204), where a distance map may be generated inside a binary object area by finding a minimum Euclidean distance for every inner point to an object boundary. External points may be excluded from analysis. A Laplace equation may be applied to a reference iso-contour and a target iso-contour to co-locate corresponding points therebetween. A second order linear partial differential equation (PDE) may be implemented for determining point-to-point correspondences, as defined in the following equation:

$$\nabla^2 \daleth = \frac{\partial^2 \daleth}{\partial x^2} + \frac{\partial^2 \daleth}{\partial y^2} = 0, \qquad (19)$$

where y defines a scalar field, called a harmonic function.

Figure 8:
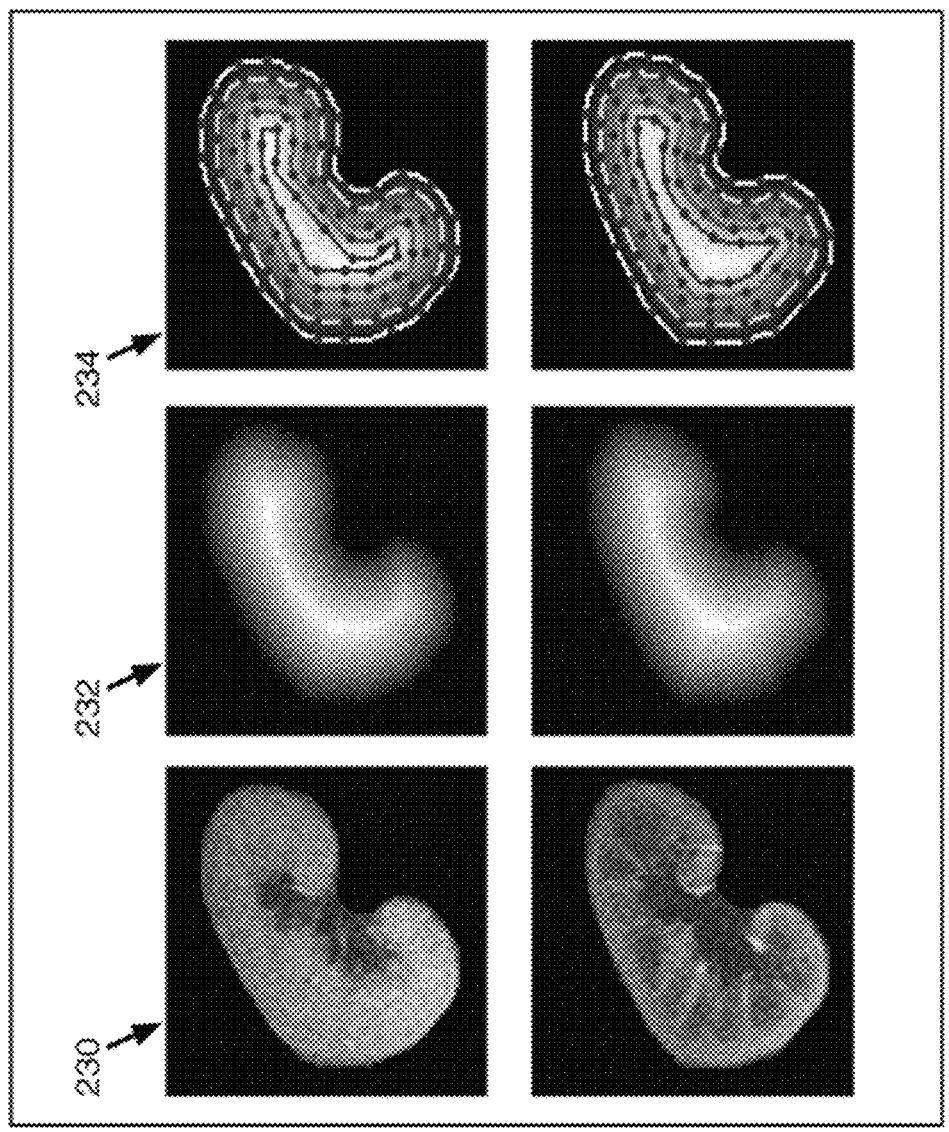
FIG. 8 provides a diagrammatic illustration of example image data and isocontours that may be processed by the computer of FIG. 2.
Figure 9:
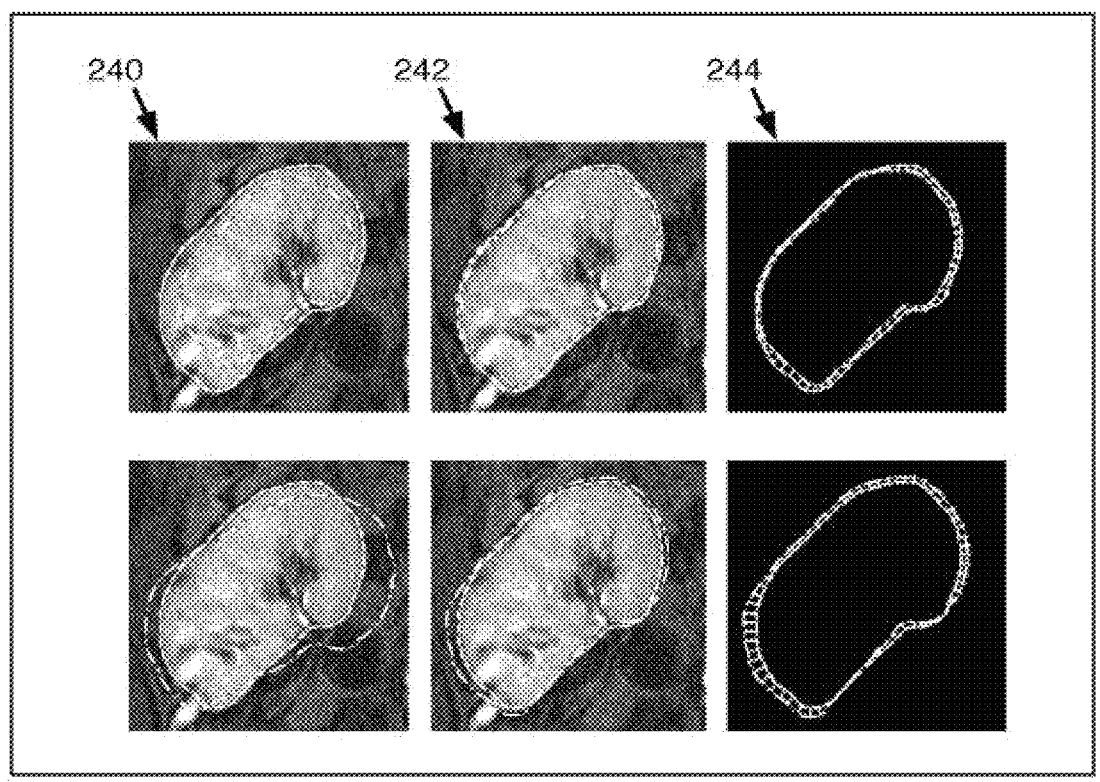
FIG. 9 provides a diagrammatic illustration of example image data and point-to-point correspondences that may be processed by the computer of FIG. 2.

The computer 30 generates nested iso-contours for a target and reference map for the segmented image data (block 206), and the computer 30 sets an initial condition (block 208) by setting a maximum and minimum (zero) potential y at the target iso-contour and corresponding reference iso-contour. Based on the initial condition, the computer co-locates corresponding points between the reference and target iso-contours (block 210) by solving equation (19) using the initial condition. Gradient vector components $$E_x = \frac{\partial \gamma}{\partial x} \text{ and } E_y = \frac{\partial \gamma}{\partial y}$$

may be determined (block 212), and the computer 30 may determine point-to-point correspondences (block 214) between the reference and target iso-contours that may be matched by forming streamlines based on the gradient vector components. Based on the point-to-point correspondences, the computer generates nonrigid registered image data such that iso-contours of segmented image data of a kidney across a time series are registered (block 216). FIG. 8 provides a diagrammatic illustration of example iso-contours that may be generated consistent with embodiments of the invention. As shown, reference and target images 230 may be used to determine distance maps 232, which may be used to generate iso-contours 234 for the segmented image data for performing nonrigid registration. FIG. 9 provides a diagrammatic illustration of co-location of point-to-point correspondences for two possible scenarios of kidney misregistration. As shown, a reference iso-contour (illustrated in dashed line) and a target isocontour (illustrated as a solid line) may be misaligned prior to affine alignment 240. After affine alignment 242, streamlines (illustrated as lines joining the reference iso-contour and target isocontour) 244 may be determined based on the Laplace equation as described above.

Figure 10:
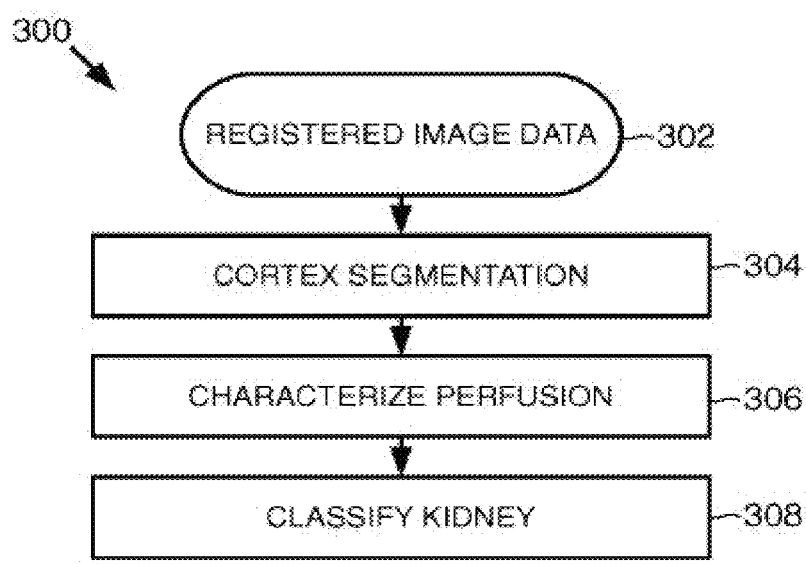
FIG. 10 is a flowchart that illustrates a sequence of operations that may be performed by the computer of FIG. 2.

FIG. 10 provides a flowchart 300 that illustrates a sequence of operations that may be performed by the computer 30 to classify a kidney for which image data has been collected, segmented, and registered. As shown, registered image data 302 may be segmented such that image data corresponding to a cortex of the kidney is determined (block 304). In general, vascular insults directly affect the kidney cortex. Hence, the cortex of the co-aligned kidneys may be segmented after the nonrigid registration. To segment the cortex, the deformable model may be applied again, using only intensity and spatial features to guide the evolution. Since the images are coregistered, the deformable boundary evolves with respect to a circular contour initialized at the center of the registered kidney. After the cortex is segmented, the image data corresponding to the cortex may serve as a mask propagating over the remaining coregistered image frames of a given perfusion time series.

The computer may characterize perfusion for the kidney using the image data corresponding to the cortex (block 306). Following the cortex segmentation, agent kinetic curves (signal intensity versus time curves) may be constructed by estimating average intensities over the entire cortex for each image frame of the time series. In general, characterization of perfusion may comprise generating a time intensity curve (TIC) by calculating the average intensities of the cortex over the time series.

To control for different physiological factors at different patient imaging exams, the computer may normalize perfusion values obtained for the cortex by the perfusion of an adjacent segment of body wall muscle that was obtainable for each subject (i.e., patient). Furthermore, embodiments may also characterize agent delivery (i.e., perfusion) during a more slowly varying phase (e.g., plateau, or tissue distribution phase), starting at approximately 30 seconds and effectively extending to approximately two minutes for peripheral injections. As will be appreciated, the characterization performed during the slowly varying phase may incorporate a large number of data points over the signal intensity time series to characterize perfusion.

Based on the perfusion characterization, the computer may classify the kidney (block 308). To distinguish between the non-rejection and acute rejection cases, the computer 30 may implement a $k_n$-nearest neighbor classifier to analyze statistical characteristics of perfusion curves averaged over the entire cortex. The characteristics may be determined from training sets of image data for kidneys including both non-rejection and acute rejection cases. In some embodiments, four perfusion indexes may be used to classify the test cases. In addition, in some embodiments, the $k_n$ classifier may be augmented by analyzing all four indexes with weights, determined by genetic optimization corresponding to the training data sets. The weights may be determined by maximizing a Euclidean distance between the weighted-combined indexes of the non-rejection and acute rejection groups in order to better classify the training data, based on a biopsy ground truth.

Figure 11:
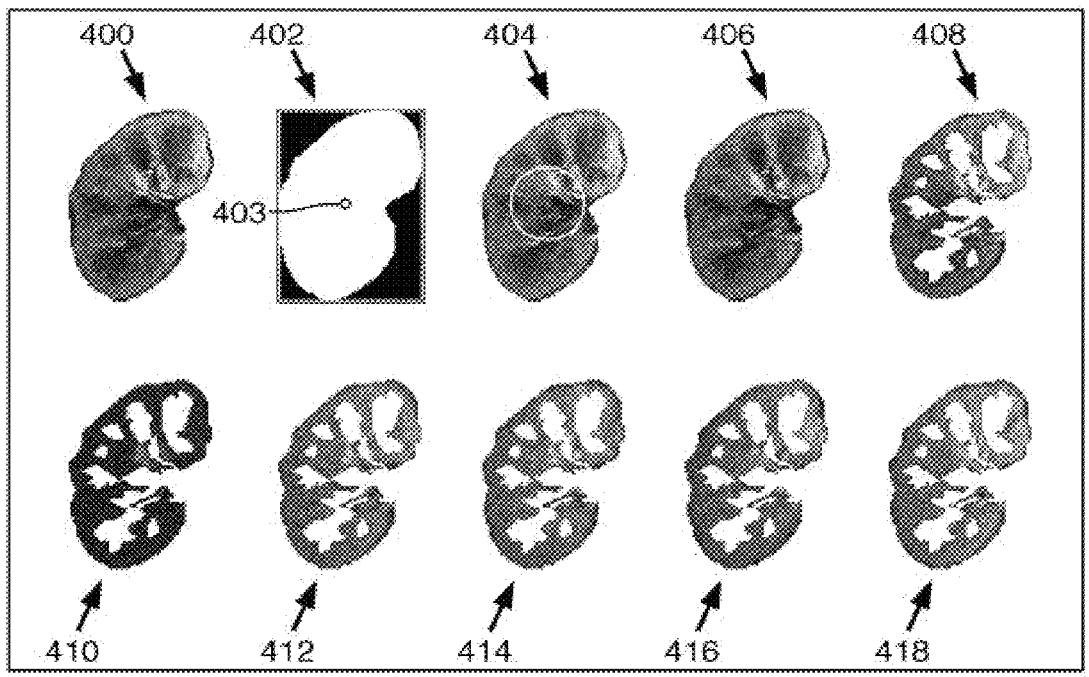
FIG. 11 provides a diagrammatic illustration of image data, a cortex mask, and application of the cortex mask to segment renal cortex image data that may be processed by the computer of FIG. 2.

The computer may classify a kidney corresponding to the received image data based at least in part on the perfusion characterization and/or time intensity curve. FIG. 11 provides a diagrammatic illustration of processing of image data consistent with embodiments of the invention. In this example, a kidney image 400 after nonrigid alignment is shown; a bounding box 402 is determined that yields a seed point 403 that may be used for level set initialization; an initial boundary 404 of the kidney object is based on the seed point 403; a final kidney boundary 406 may be determined that corresponds to a cortex of the kidney object; an extracted cortex mask 408 may be determined and may be applied to time series images corresponding to the kidney object 400 to segment image data from the time series images corresponding to the cortex 410-418.

Figure 12:
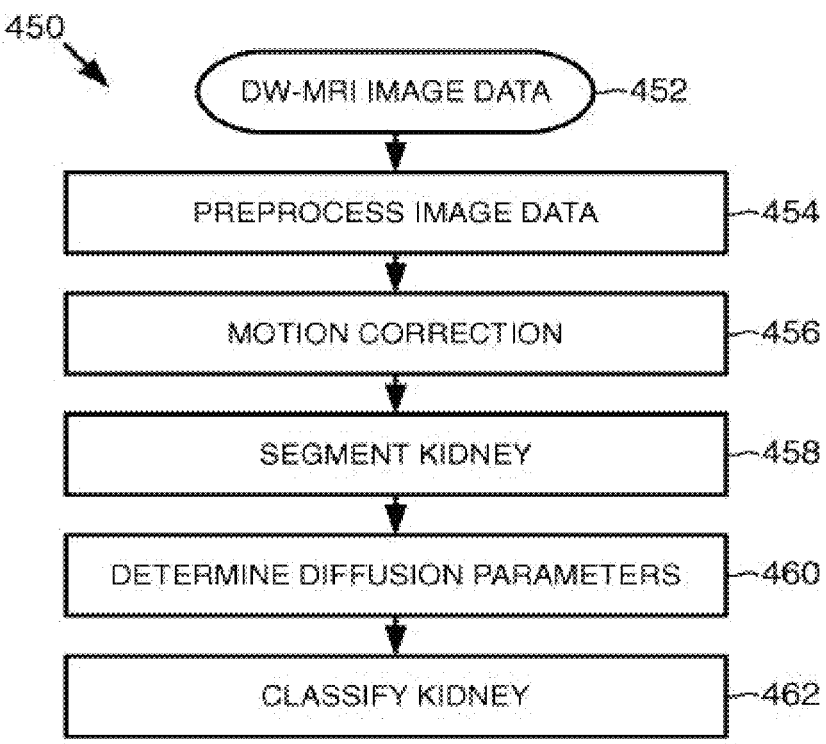
FIG. 12 is a flowchart that illustrates a sequence of operations for diffusion weighted magnetic resonance imaging data that may be performed by the computer of FIG. 2.

Consistent with some embodiments, the image data received by the computer 30 may comprise four-dimensional DW-MRI data that generally includes three-dimensional data and a b-value (which corresponds to a strength and direction of a magnetic diffusion gradient). In these embodiments, an image of a time series may comprise a voxel (i.e., an image data point having three dimensions). FIG. 12 provides a flowchart 450 that illustrates a sequence of operations that may be performed by the computer 30 to process DW-MRI image data 452 consistent with embodiments of the invention. The computer 30 preprocesses the image data 452 (block 454) by applying intensity histogram equalization using a nonparametric bias correction process to the image data. In general, the computer 30 may preprocess the image data to compensate for low frequency intensity non-uniformity or inhomogeneity. The computer 30 performs motion correction on the image data (block 456) by performing a three-dimensional B-splines transformation using a sum of square difference as a similarity metric.

A kidney object may be segmented from the image data (block 458). Consistent with embodiments of the invention, the computer 30 may integrate regional statistics derived from kidney and background regions may be used to determine portions of the image data corresponding to the kidney object and portions of the image data corresponding to background. Embodiments of the invention may analyze appearance, shape, and/or spatial features of the image data using a joint MGRF image model. As will be appreciated, in these embodiments, the image data comprises three-dimensional data and further includes b-value data. Therefore, a joint MGRF image model may be constructed based at least in part on the following equations:

$$R=\{(x,y,z):0 \leq x \leq X-1, 0 \leq y \leq Y-1, 0 \leq z \leq Z-1\}, \quad (20)$$

$$Q=\{0, 1, \ldots, Q-1\}; \text{ and}$$

L={0, 1}, where L denotes a finite 3D arithmetic lattice supporting grayscale images and their region (segmentation) maps, a finite set of Q integer gray values, and a binary set of region labels, i.e., object ("1") and background ("0") labels.

$$g=\{g_{x,y,z}:(x,y,z) \in R; g_{x,y,z} \in Q\},$$

$$m=\{m_{x,y,z}:(x,y,z) \in R; m_{x,y,z} \in L\}$$

is a grayscale image taking values from Q, i.e., g: R→Q, and a region map taking values from L, i.e., m: R→L.

If input DW-MRI image data is defined as g, and co-aligned to a training database of kidney image data, a map m may be described with a joint probability model:

$$P(g,m)=P(g|m)P(m), \quad (21)$$

which combines a conditional distribution of images given the map $P(g|m)$ and an unconditional probability distribution of maps $P(m)=P_s(m)P_v(m)$, where $P_s(m)$ denotes on adaptive shape prior, and $P_v(m)$ is a Gibbs probability distribution with potentials V, which specifies an MGRF model of m.

To reduce the variability across subjects (i.e., image data from different patients) and to enhance the segmentation accuracy, embodiments of the invention may employ an adaptive shape model of an expected kidney shape. To create an expected kidney shape, a training set of kidney image data collected from different subjects may be co-aligned using the 3D B-splines based transformation described above. Probabilistic shape priors may be spatially variant independent random fields of region labels described by the following equations:

$$P_s(m) = \Pi_{(x,y,z) \in R} P_{s:x,y,z}(m_{x,y,z}) \quad (22)$$

where $P_{s:x,y,z}(1)$ corresponds to a voxel—wise empirical probability for each label $l \in L$ For input DW-MRI data to be segmented, a shape prior may be constructed by an adaptive process guided by the visual appearance features of the input image data, where such adaptive process may be trained with previously segmented data sets (e.g., training sets) that may be used to create probabilistic maps for kidney object/background labels. Consistent with embodiments of the invention, for a kidney to be classified, corresponding DW-MRI data to be segmented may be first co-aligned with one of the training sets used to create the prior kidney shapes. Then, an appearance-guided shape prior may be estimated and updated based on an analysis of the aligned image data.

Furthermore, some embodiments of the invention may determine a second-order appearance model that may be used for segmentation. Generally, the second-order appearance model may incorporate three dimensional pair-wise interactions between region labels into a model, where the interactions may be estimated using a Potts model (i.e., an MGRF model with a nearest 26-neighbors of voxels) and analytic bi-valued Gibbs potentials that depend only on whether nearest pairs of labels are equal or not. A second-order appearance model may be determined based at least in part on the following equations:

$f_{eq}(m)$ denotes the relative frequency of equal labels in the neighboring voxel pairs:

$$((x,y,z),(x+\xi,y+\eta,z+\varsigma)) \in R^2; (\xi,\eta,\varsigma) \in \{(\pm1,0,0),(0,\pm1,0),(\pm1,\pm1,0),(\pm1,0,\pm1),(0,\pm1,\pm1),(\pm1,\pm1,\pm1)\}, \quad (23)$$

where the initial map results in an analytical maximum likelihood estimates of the potetials $$V_{eq} = -V_{ae} \approx 2f_{eq}(m)-1,$$

and computing voxel—wise probabilities corresponds to $P_{V:x,y,z}(l); l \in L$.

In addition, some embodiments of the invention may determine a first-order appearance model that may be used for segmentation. Generally, the first-order appearance model may comprise a linear combination of discrete Gaussians (LCDG) with positive and negative discrete Gaussian components. The first-order appearance model generally separates mixed empirical one dimensional distribution of DW-MRI voxel intensities into two distinct components, associated with each label. As will be appreciated, the first-order appearance model yields an initial region map that is formed by the voxel-wise classification of the image gray values.

Consistent with embodiments of the invention, the appearance-based shape model, the second-order appearance model, and the first-order appearance model may be integrated into a joint MGRF model to provide voxel-wise guidance of the level-set. A magnitude and direction of contour evolution at a voxel u=(x, y, z) may be determined based on the following equations:

$$u_{md} = \begin{cases} -\kappa P_{ob:w}, & \text{if } P_{ob:u} > P_{bg:u} \\ \kappa P_{bg:w}, & \text{if } P_{bg:u} > P_{ob:u} \end{cases}, \quad (24)$$

where κ corresponds to a mean contour curvature, $P_{ob:u}$ corresponds to the joint MGRF probability for a kidney object, and $P_{bg:u}$ corresponds to the joint MGRF probability for background.

$$P_{ob:u} = \frac{\Omega_{ob:u}}{\Omega_{nb:u} + \Omega_{rgu}}, \quad (25)$$

$P_{bg:u} = 1 - P_{ob:u}$, where $$\Omega_{ob:u} = p(q|1) P_{V:u}(1) P_{sp:u}(1)$$

$$\Omega_{bg:u} = P(q|0)(1-P_{V:u}(1))(1-P_{sp:u}(1)),$$

p(q|l) denotes the voxel—wise probability of the intensity q∈Q for the LCDG model of the kidney (l=1) or background (l=0) appearance Based on the segmented image data that corresponds to the kidney object, the computer 30 may determine diffusion parameters (block 460). In some embodiments, the computer 30 may determine an apparent diffusion coefficient (ADC) for the kidney object of the segmented image data, where the ADC may be determined based at least in part on the following equation:

$$ADC = \frac{1}{b_0 - h} \ln\left(\frac{S_b}{S_0}\right), \quad (26)$$

where $S_0$ corresponds to DW-MRI data acquired at $b_Q$ and $S_b$ corresponds to a given b-value.

Figure 13:
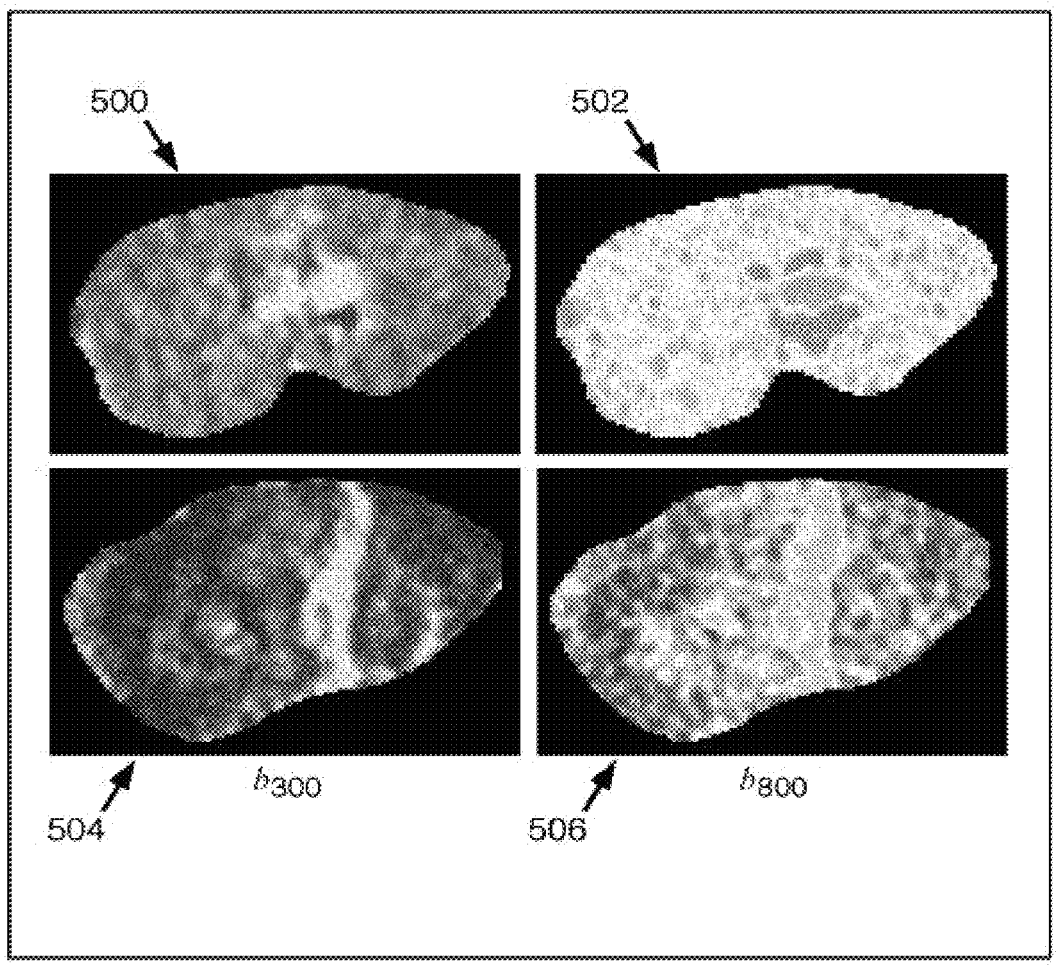
FIG. 13 provides a diagrammatic illustration of image data and a color-coded kidney that may be processed by the computer of FIG. 2.
Figure 14:
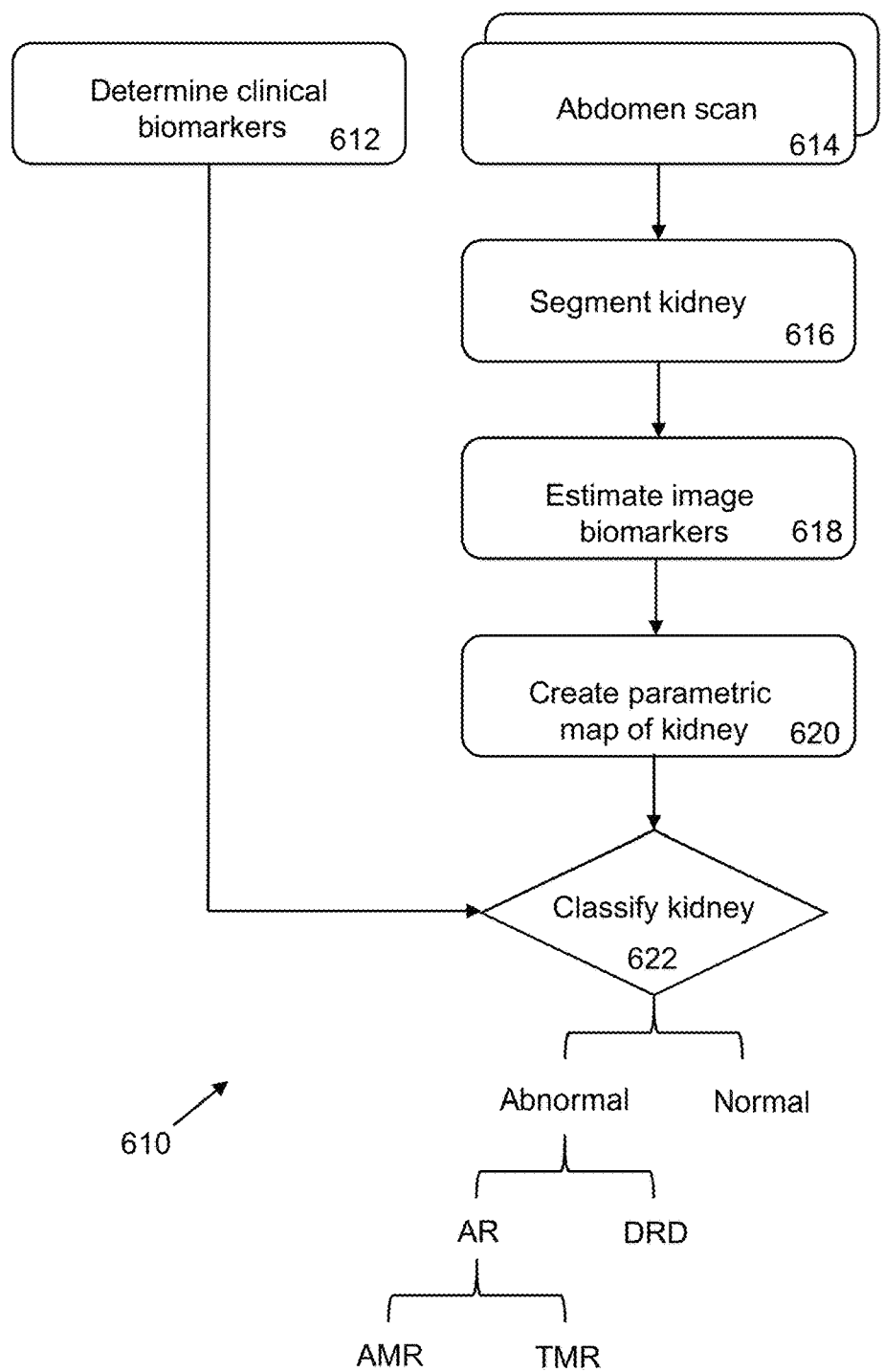
FIG. 14 is a flowchart of a computer-aided system for kidney function evaluation by the integration of image-markers derived from DCE-MRI and/or DW-MRI and BOLD-MRI with clinical biomarkers. Different renal diseases (DRD), anti-body mediated rejection (AMR) T-cell mediated rejection (TMR), CrCl (creatine clearance), serum plasma creatine (SPCr), perfusion indicies (PIs), apparent diffusion coefficients (ADC) and apparent relaxation rate (R2*) denote various renal diseases.

The computer 30 may classify the kidney corresponding to the image data based at least in part on the diffusion parameters (block 462). In general, the computer 30 may compare the ADC determined for different b-values to ADC values determined for a training set. The computer 30 may perform a $k_n$-nearest neighbor classifier and a leave-one-subject out analysis process to classify the kidney as a rejection or non-rejection case. FIG. 13 provides a diagrammatic illustration of a cross-sectional voxel-wise parametric-maps constructed from DWMRI image data collected at different b-values. In this example, a first set of image data corresponds to DW-MRI image data collected for a non-rejection case at b=300 s/mm$^2$ 500 and the non-rejection case at b=800 s/mm$^2$ 502. A second set of image data corresponds to DW-MRI image data collected for a rejection case at b=300 s/mm$^2$ 504 and b=800 s/mm$^2$ 506.

Therefore, embodiments of the invention may be used for the classification of acute rejection versus non-rejection status of kidney transplants. In some embodiments, two-dimensional dynamic contrast-enhanced magnetic resonance imaging data associated with a kidney may be processed and analyzed. In some embodiments, four-dimensional diffusion weighted magnetic resonance imaging data associated with a kidney may be processed an analyzed. In general, kidney objects may be segmented from adjacent structures with a level set deformable boundary guided by a stochastic speed function that accounts for a fourth-order Markov-Gibbs random field model of the kidney/background shape and appearance. A Laplace based nonrigid registration approach may be used to account for local deformations caused by physiological effects. For example, the target kidney object may be deformed over closed, substantially equi-spaced contours (iso-contours) to closely match a reference object. In some embodiments, renal cortex image data may be segmented from kidney image data, as the renal cortex is most affected by rejection. To characterize rejection, one or more features may be determined, including for example, perfusion may be estimated from contrast agent kinetics using empirical indexes. For example, transient phase indexes (peak signal intensity, time-to peak, and initial up-slope), and a steady-phase index defined as the average signal change during the slowly varying tissue phase of agent transit may be used to estimate one or more features. A $k_n$-nearest neighbor classifier may distinguish between acute rejection and non-rejection for classification.

Experimental results in 50 subjects, using a combinatoric $k_n$-classifier, correctly classified 92% of training subjects, 100% of the test subjects, and yielded an area under a receiver operating characteristics (ROC) curve that approached an ideal value. Therefore, embodiments of the invention may be utilized as a reliable non-invasive diagnostic tool. In other experimental results, of 35 subjects, embodiments described herein correctly classified 91.5% of the test subjects. Additional details regarding experimental results may be found in the incorporated description materials [1], [2], [3], and [4].

In general, the routines executed to implement the embodiments of the invention, whether implemented as part of an operating system or a specific application, component, program, object, module or sequence of instructions, or even a subset thereof, will be referred to herein as "computer program code," or simply "program code." Program code typically comprises one or more instructions that are resident at various times in various memory and storage devices in a computer, and that, when read and executed by one or more processors in a computer, cause that computer to perform the steps necessary to execute steps or elements embodying the various aspects of the invention. Moreover, while the invention has and hereinafter will be described in the context of fully functioning computers and computer systems, those skilled in the art will appreciate that the various embodiments of the invention are capable of being distributed as a program product in a variety of forms, and that the invention applies equally regardless of the particular type of computer readable media used to actually carry out the distribution. Examples of computer readable storage media include but are not limited to physical, tangible storage media such as volatile and non-volatile memory devices, floppy and other removable disks, hard disk drives, magnetic tape, optical disks (e.g., CD-ROMs, DVDs, etc.), among others.

In addition, various program code described herein may be identified based upon the application within which it is implemented in a specific embodiment of the invention. However, it should be appreciated that any particular program nomenclature that follows is used merely for convenience, and thus the invention should not be limited to use solely in any specific application identified and/or implied by such nomenclature. Furthermore, given the typically endless number of manners in which computer programs may be organized into routines, procedures, methods, modules, objects, and the like, as well as the various manners in which program functionality may be allocated among various software layers that are resident within a typical computer (e.g., operating systems, libraries, API's, applications, applets, etc.), it should be appreciated that the invention is not limited to the specific organization and allocation of program functionality described herein.

Embodiments of the invention therefore analyze and classify a kidney by analyzing medical image data associated with the kidney. In some embodiments, automated classification of a kidney using the present invention may provide significant benefits over conventional methods, including for example, improved classification speed and accuracy, and non-invasive classification as compared to a biopsy.

In addition, it will be appreciated that the invention may have applicability in terms of classifying other anatomical structures, including other organs. Furthermore, it will be appreciated that some embodiments of the invention may evaluate a non-transplanted kidney for various purposes by using a different learned model.

Now turning to FIGS. 14-32, FIG. 14 illustrates an exemplary automated process 610 for accurate, non-invasive evaluation of the transplant status of a kidney, classification of a kidney. Process 610 in particular is based upon the determination/classification of a transplanted kidney status as either normal (NKT) or abnormal (ABKT), then, for abnormal status, determine/classify the abnormal as acute rejection (AR) or different renal disease (DRD), then, for AR status, determine/classify the AR type as TMR or AMR. In addition, the process 610 provides the clinician with a visual assessment via a color-coded map of the abnormal regions of the transplanted kidney.

Process 610 receives as input one or more clinical biomarker data (block 612). Process 610 also receives as input a plurality of abdomen scans using a plurality of imaging techniques (block 614), including, in some embodiments, BOLD-MRI and at least one of DW-MRI and DCE-MRI. In some embodiments, DCE-MRI is used with patients with GFR>30 ml/min and DW-MRI is used with patients with GFR<30. In other embodiments, all three of DCE-MRI, DW-MRI, and BOLD-MRI are used. In further embodiments, at least one MRI-based imaging technique is combined with at least one other imaging technique, which may or may not be MRI-based.

Process 610 continues by segmenting kidney image data from the other image data of the plurality of abdomen scans (block 616, described in further detail in Section A). In general, an abdomen scan may include one or more two dimensional "slices" of image data generated from a medical imaging device such as an aCT scanner, an MRI imager, or other medical imaging device. As a component of the segmenting step, the kidney image data may also be registered to compensate for motion effects as described earlier in this disclosure.

Process 610 continues by estimating image biomarkers, also referred to as functional parameters derived from image data, to form parametric maps for determining and classifying the status of the transplanted kidney in combination with the clinical biomarkers (blocks 618 and 620, respectively, described in further detail in Sections B, C, and D). Image biomarkers from the different imaging modalities include the perfusion indices (PIs) from the segmented DCE-MR images and/or ADC values from the segmented DW-MR images acquired at multiple low and high b-values, and R2* values from the segmented BOLD-MR images. Generally, a learned model may be developed based on known training sets of classified transplanted kidneys and based on the image biomarkers and clinical biomarkers determined for such classified transplanted kidneys. After analyzing the image data and considering the clinical biomarkers with the learned model, embodiments of the invention may classify the kidney associated with the received abdominal scan (block 622, described in further detail in Section E)). The kidney transplant status is classified as normal (NKT) or abnormal (ABKT), ABKT classified as either AR or DRD, and AR classified as TMR or AMR for diagnostic purposes.

The process 610 employs several novel components that will be described in further detail below. Specifically, components of this process include: (i) A $4^{th}$-order Markov-Gibbs random field (MGRF) model of spatial interactions has been integrated into a 3D level-set deformable model to accurately segment a transplanted kidney in the presence of large grey-level inhomogeneities between its different structures, e.g., the cortex and medulla; (ii) to accurately diagnose the transplanted kidney, the DW-MR images have been acquired at both low and high b-values, which describe blood perfusion and diffusion, respectively, inside the kidney as well as the BOLD-MR images have been acquired at different time series to give a clear picture of the amount of oxygen diffused blood inside the kidney; (iii) to fuse/integrate the ADCs at different b-values, and to fuse/integrate the R2* at different time-sequences, stacked autoencoders (SAEs) have been used after establishing voxel-to-voxel correspondences between the segmented images of the kidney transplants; (iv) fusion of the clinical biomarkers with the image-derived markers to obtain final classification results; and (v) a novel non-negativity constraint (NC) has been applied to all SAEs, (abbreviated then SNCAEs) for more efficient signal dimensionality reduction and faster learning, i.e., faster convergence to goal parameter estimates for encoding and classification layers when an SNCAE is trained. The SNCAE escapes non-causal negative weighting parameters, thus enhancing the final CAD accuracy.

One or more steps in process 610 may be implemented in an automated fashion, utilizing a computer or other electronic device to implement such steps. An exemplary computer 30 is described above. As an example, computer 30 may include a computer aided diagnostic (CAD) system program 50 used to implement one or more of the steps described above in connection with process 610. For the purposes of implementing such steps, an image database 52, storing medical image scans, may be implemented in computer 30. It will be appreciated, however, that some steps in process 610 may be performed manually and with or without the use of computer 30.

172 patients who underwent kidney transplantation were divided according to the MRI modality as 50 DCE-MRIs, 103 DW-MRIs of which 66 are 1.5 T DW-MRIs and 37 are 3T DW-MRIs, and 19 BOLD-MRIs and included 116 males and 56 females and range in age from 10 to 56 years (the mean age of 27.13±10.11 years). Patients were divided into two groups: normal (NKT) and abnormal (ABKT) kidney transplants. As a part of routine medical care after transplantation, all patients of both groups were assessed with serum creatinine laboratory values with a normal (basal) level of ≤1.3 mg dl⁻. The NKT group (68 patients) included patients with healthy graft function. Most of the NKT group patients only underwent the MRI scans two weeks after transplantation. The ABKT group (104 patients) included patients with acute renal rejection (AR) and DRD (e.g., acute tubular necrosis, tubular inflammation, acute tubular injury, graft amyloidosis, chronic allograft injury, etc.) based on their renal biopsy histology. All patients of the ABKT group underwent the MRI scans two weeks after transplantation and just before the renal biopsy. Both the MRI scans and biopsy were included in the final analysis and examined by a nephrologist and a radiologist.

Figure 15:
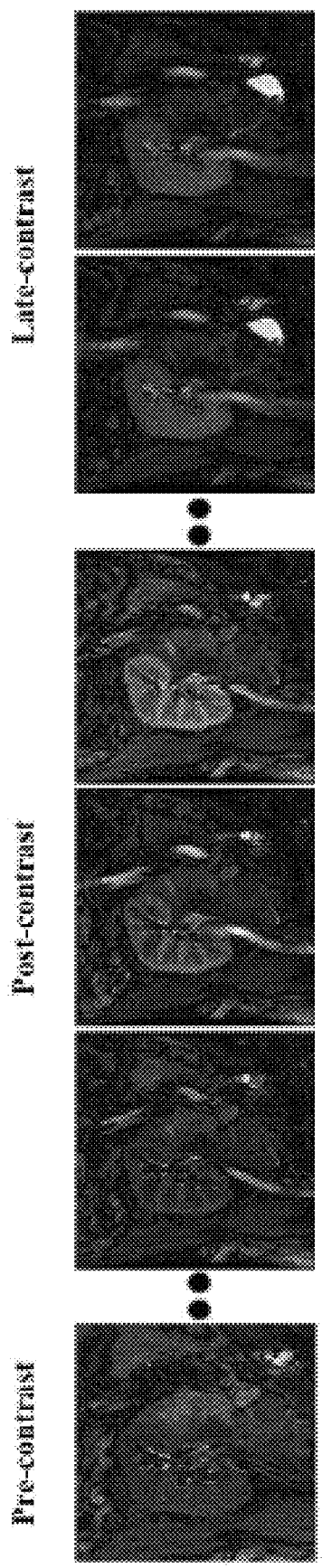
FIG. 15 depicts coronal cross-sections of raw DCE-MRI sequence with Pre-, Post-, and Late-contrast.

The DCE-MRI was performed using temporal sampling adequate to characterize the transit of the contrast agent during the first pass, while maintaining adequate spatial resolution for visualizing the anatomy. We used gradient-echo T1 imaging using a 1.5 T MRI scanner (Signa Horizon LX Echo speed; General Electric Medical Systems, Milwaukee, Wis., USA) with a phased-array torso surface coil. Gadoteric acid (Dotarem 0.5 mmol/mL; Guerbet, France) clinical agent was injected at the rate of 3-4 ml/sec; at the dose of 0.2 ml/kg body weight (BW). Imaging parameters were as follows: slice thickness: 5 mm; repetition time (TR)=30-40 msec; echo time (TE)=2-3 msec; flip angle 70$^{7o}$; field of view (FOV) 38 cm, and matrix size of 256×160. For each patient, to obtain representative sampling to characterize perfusion, we used a single coronal image section at the level of the renal hilum of the transplanted kidney. Approximately 80 repeated temporal frames were obtained at 3 sec intervals. FIG. 15 shows a sample of coronal cross-sections of raw DCE-MRI data sequence with pre-, post, and late-contrast.

The DW-MR images were acquired before any biopsy procedure by using a 1.5 T and 3 T SIGNA Horizon scanner (General Electric Medical Systems, Milwaukee, Wis., USA). Coronal DW-MR images have been obtained by using a body coil and a single-shot spin-echo echo-planar sequence (TR/TE, 8000/61.2 ms; bandwidth, 142 kHz; 1.28×1.28 mm² matrix; section thickness of 4 mm; intersection gap of 0 mm; FOV of 36 cm; 7 acquired signals; water signals acquired at different b-values of ($b_0$, $b_{50}$, $b_{100}$, $b_{200}$, $b_{300}$, $b_{400}$, $b_{500}$, $b_{600}$, $b_{700}$, $b_{800}$, $b_{900}$, and $b_{1000}$) s/mm².

Figure 16:
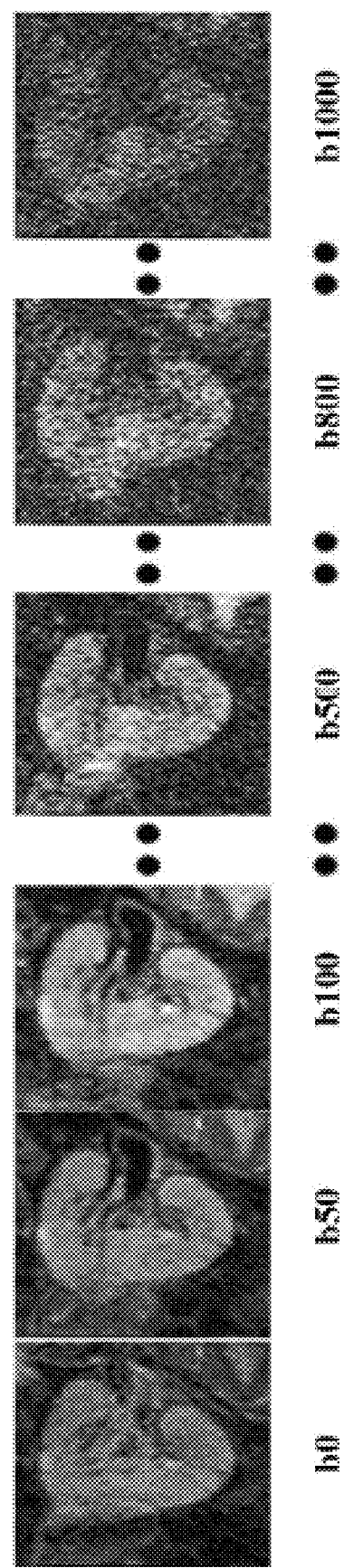
FIG. 16 depicts coronal cross-sections of raw DW-MRI sequence at different b-values, at $b_0$, $b_{50}$, and $b_{100}$-$b_{1000}$, step 100 s/mm$^2$.

Approximately 50 sections have been obtained in 60-120 seconds to cover the whole kidney. FIG. 16 shows a sample of coronal cross-sections of raw DW-MRI data sequence at different b-values, starting at $b_{50}$, $b_{100}$-$b_{1000}$, step 100 s/mm².

Figure 17:
FIG. 17 depicts coronal cross-sections of raw BOLD-MRI sequence at different echo times from 2 msec to 22 msec, step 5 msec.

The BOLD-MR images were acquired before any biopsy procedure by using a 3 T MRI Ingenia, Philips medical system, The Best, Netherlands. Coronal DW-MR images have been obtained and the parameters were as follows: TR=140 ms; TE=2 ms; Flip angle 25 degree; Bandwidth 150 kHz; Matrix 96×96; number of signals acquired 1; FOV 14.4 cm; thickness 6.0 mm. Approximately 5 repeated cross-sections have been obtained at 5 ms interval. FIG. 17 shows a sample of coronal cross-sections of raw BOLD-MRI data sequence at different echo-times, starting at 2-22, step 5 msec.

A. 3D Kidney Segmentation

Segmenting kidneys from surrounding tissues on MR images is a key starting step towards obtaining a goal diagnosis. However, achieving an accurate kidney segmentation is a challenging task because of kidney motions due to breathing and heart beating; kidney shape changes due to inter-patient anatomical differences; low contrast between the kidney and other abdominal structures, (FIGS. 15, 16, and 17); low SNR and artifacts that complicate image alignment; and geometric distortions due to long acquisition time. To overcome these challenges, the instant segmentation relies on multiple image features to accurately delineate the kidney and thus facilitates analysis of transplant status. Basic notations and details of our segmentation are outlined below.

For describing processing steps, let p=(x, y, z) denote a voxel at 3D position with discrete Cartesian coordinates (x, y, z) and let R={(x, y, z):0≤x≤X-1; 0≤y≤Y-1; 0≤z≤Z-1} be a finite 3D arithmetic lattice of unit voxels. The lattice has the size of XYZ and supports both grayscale images and their parametric or region (segmentation) maps. A grayscale image, g={gp: p∈R; gp∈Q}, takes voxel-wise values from a finite set, Q={0, 1, . . . , Q-1}, of Q integer gray levels, i.e. gr: R→Q. A region map, m={mp: p∈R; mp∈L}, takes voxel-wise values from a binary set of region labels, L={0, 1}, where 0 and 1 indicate the background and kidney, respectively, i.e. m: R→L.

Figure 18:
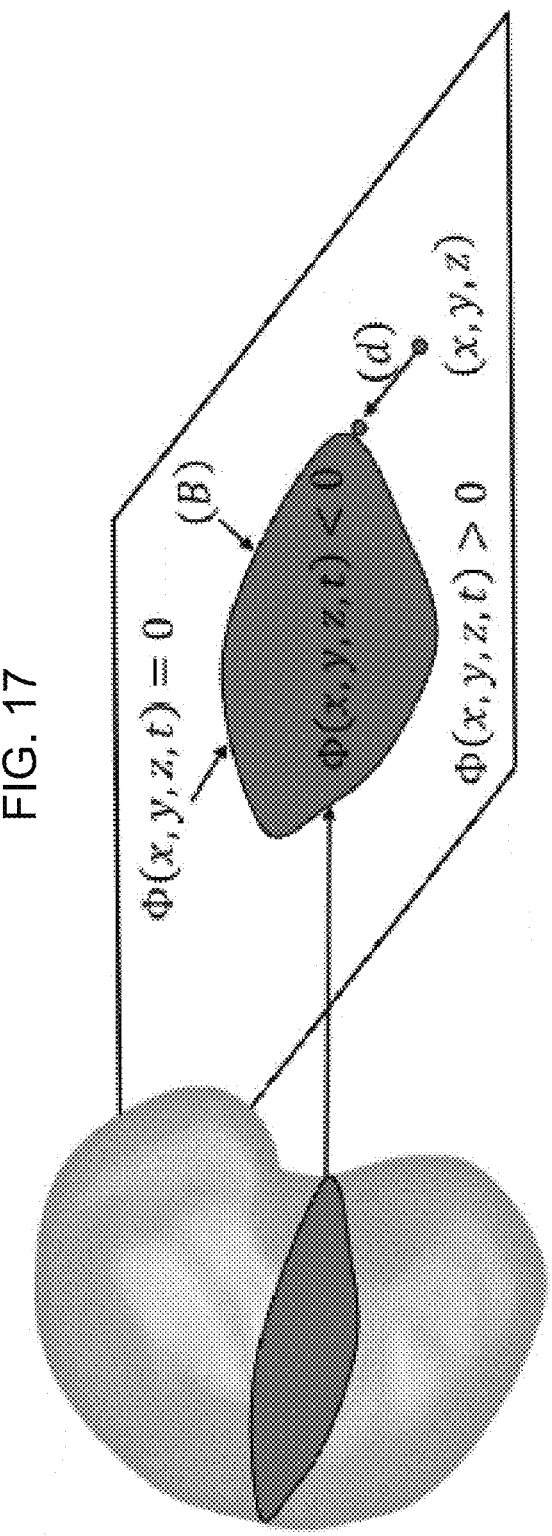
FIG. 18 provides a diagrammatic illustration of a 3D zero-level set of a function $\Phi(p=[x, y, z], t)$.
Figure 20:
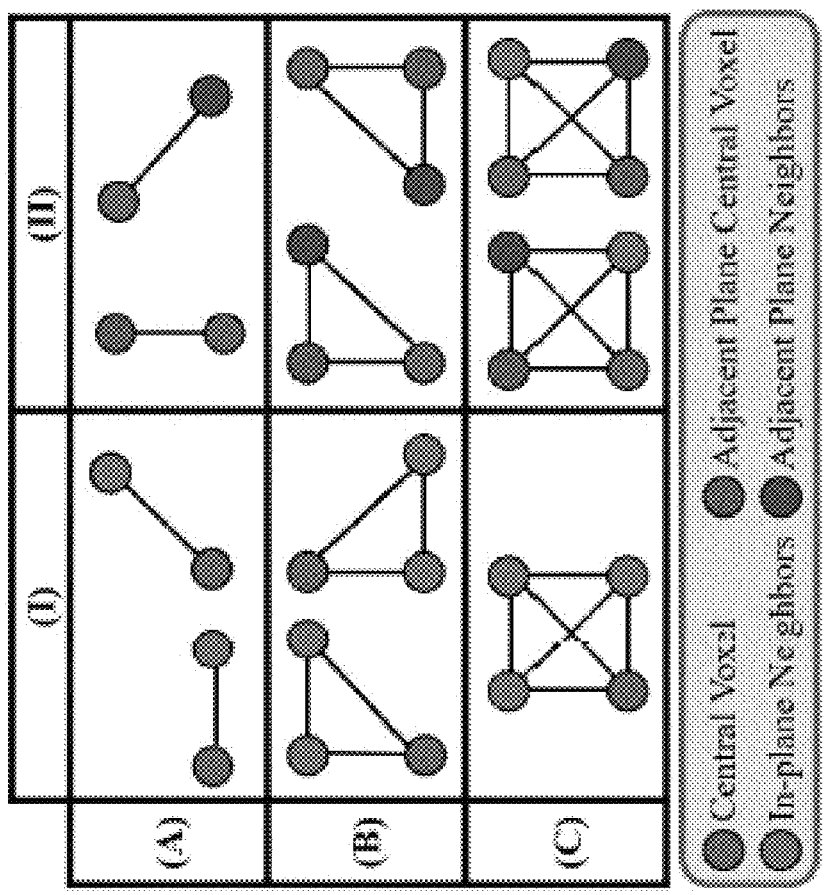
FIG. 20 displays examples of (A) $2^{nd}$-, (B) $3^{rd}$-, and (C) $4^{th}$-order cliques containing the central voxel (purple) of FIG. 19A and its neighbors in the same (I) and adjacent (II) planes.
Figure 19:
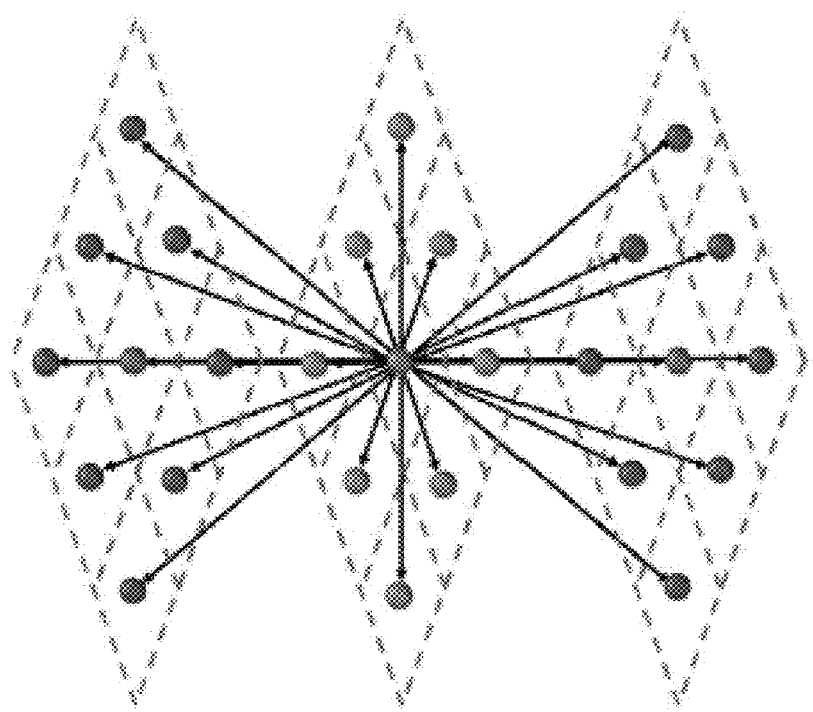
FIG. 19 provides a diagrammatic illustration of the nearest 26-neighborhood of a voxel for the 4th-order spatial model.

A 3D geometric (level-set-based) deformable boundary, is employed for the MRI kidney segmentation due to successful results in a wide range of applications, including medical imaging, e.g., for segmenting brain, prostate, liver, kidney etc. Due to simplicity, flexibility, and ability to handle complex shapes and topological changes independently of surface parameterizations, these deformable boundaries are more popular than the alternative parametric ones. Points of an object—background boundary at each time instant t are specified implicitly as a zero-level set, $B_t = \{p: p \in R; \Phi(p, t)=0\}$, of arguments of a specific higher-dimensional function, $\Phi(p, t)$, on the lattice R. The function is often a signed distance map:

$$\Phi(p, t) = \begin{cases} d(p, B_t) & \text{if } p \text{ is inside the boundary } B_t; \\ 0 & \text{if } p \text{ is at the boundary } B_t; \text{ and} \\ -d(p, B_t) & \text{if } p \text{ is outside the boundary } B_t \end{cases} \quad (27)$$

where $d(p, B_t) = \min_{b \in B_t} d(p, b)$ is the distance from the point p to the boundary $B_t$, and d(p, b) is the Euclidean distance between two lattice points p and b, as shown in FIG. 18. The function $\Phi(p, t)$ evolves in discrete time t=nτ with a fixed step, $\tau > 0$, as [45]: (28),(29)

$$\Phi(p, (n+1)\tau) = \Phi(p, n\tau) - \tau F_n(p)|\nabla \Phi(p, n\tau)|$$

where n = 0, 1, 2, ... , is the time index:

$\nabla \Phi(p, n\tau)$ is the spatial gradient of $\Phi(p, n\tau)$:

$$\nabla \Phi(p, n\tau) = \left[ \frac{\partial \Phi(p, n\tau)}{\partial x}, \frac{\partial \Phi(p, n\tau)}{\partial y}, \frac{\partial \Phi(p, n\tau)}{\partial z} \right];$$

|a| denotes the magnitude of the vector a, and $F_n$ (p) is a speed function guiding the evolution of an initial boundary Bo, defined at the starting instant t=0, i.e., for n=0.

Most of the conventional speed functions quantify visual appearance differences between the object and its background in terms of mean values and variances of image intensities, intensity edges or gradient vector flow, and similar regional signal characteristics. Thus, their guidance may fail if images to be segmented are noisy and/or object-background contrast is low. The noise and inconsistencies due to low-frequency non-uniformity, or inhomogeneity of intensities, are suppressed in part by preprocessing that combines histogram equalization with non-parametric bias correction. To accurately segment the kidneys from noisy and low-contrast MRIs, the instant guiding function accounts for not only regional kidney-background appearance, but also for a kidney shape prior and high-order spatial relations in the goal region map. To provide voxel-wise guidance for the evolving boundary, all appearance and shape descriptors are combined into a joint Markov-Gibbs random field (MGRF) model of an MR image, g, and its binary kidney-background region map, m. The model is specified by a joint probability distribution P (g, m)=P (g|m)P (m), where P (g|m) and P (m) denote a conditional probability distribution of images, given a map, and an unconditional distribution of region maps, respectively. The latter distribution is factored into two terms: P (m)=Psp (m)PV (m), where Psp (m) denotes an appearance-based adaptive shape prior, and PV (m) is a high-order Gibbs probability distribution with potentials V. The potentials evaluate strengths of not only the nearest neighbor pairwise dependencies, but also of triple- and quad-dependencies, which specify a higher-order spatially homogeneous MGRF model of region maps. These components of the joint image-map model are outlined below.

1) First-order kidney/background appearance model: To accurately model MRI appearance, the empirical marginal probability distribution of intensities are approximated with a linear combination of discrete Gaussians (LCDG). The LCDG with two positive dominant components (one each for the kidney and background) and multiple sign-alternate subordinate components allow for separating the mixed marginal of the MRI voxel-wise intensities into the two distinct LCDGs, each associated with the kidney or background label.

2) Higher-order MGRF appearance model: Compared to other imaging modalities, lower SNRs and frequent artifacts, together with geometric distortions due to long acquisition time and larger inhomogeneities of internal structures, such as cortex and medulla, in the MRI hinder the kidney segmentation. To better account for intra-kidney variabilities, spatial dependencies between each voxel and its nearest neighbors in the MR images have been incorporated into the instant segmentation process. Incorporated spatial relationships not only reduce noise impacts, but also reveal homogeneities and thus enhance the overall segmentation accuracy. Unlike more conventional pairwise-spatial homogeneity descriptors, the instant process uses a 4th-order MGRF with analytically estimated potentials to describe those relationships. To find the potential estimates, an initial kidney map, m, is constructed by a simple Bayes classification using joint voxel-wise shape and intensity probabilities. Then, inter-label spatial dependencies in this map, m, are modeled by the 4th-order spatial MGRF with the nearest 26-neighborhood shown in FIG. 19. This model adds triple and quad clique families to the more conventional 2nd-order Potts MGRF.

Let $C_a$ be a family of s-order cliques of the interaction graph with nodes in the lattice sites $p \in R$ and edges connecting interdependent pairs of the sites. Let A clique families describe spatial geometry of interdependencies of region labels in the kidney maps, m. Then the model is specified by the Gibbs probability distribution:

$$P_V(m) = \frac{1}{Z_V} \exp\left(\sum_{a=1}^{A} \sum_{e \in C_a} V_a(m_p : p \in c)\right) \quad (30)$$

where $V=[V_0 (\mu):\mu]$ in $\{0, 1\}^{V_0} \to (-\infty, \infty)$: a=1, ..., A] is a collection of potential functions for the families $C_a$, $v_a$ is the clique size ($v_a \in \{2,3,4\}$) for the family $C_a$; $\mu$ is a label configuration on the clique, i.e., a pair, triple, or quadruple of binary numbers 0 and 1, and $Z_V$ is the normalizing factor, called the partition function, over the entire population $M=\{0,1\}^{XYZ}$ of the maps:

$$Z_v = \sum_{m \in M} \exp\left(\sum_{a=1}^{A} \sum_{e \in C_o} V_a(m_p : p \in c)\right) \quad (31)$$

For equiprobable binary labels, $\mathcal{M}_p \in \{0,1\}$, the marginal co-occurrence probabilities over the $2^{nd}$-, $3^{rd}$-, and $4^{th}$-order cliques are ¼, ⅛, and 1/16, respectively. Provided the cardinalities of the clique families are close to the lattice cardinality for all the families a=1, ..., A and only the quality ("eq") or inequality ("ne") of all the clique-wise labels are taken into account, the corresponding estimates of the $2^{nd}$-, $3^{rd}$-, and $4^{th}$-order potentials are as follows:

$$V_{2:a:eq} = 4\left(F_{a:eq}(m) - \frac{1}{2}\right) = -V_{2:a:ne} \quad (32)$$

$$V_{3:a:eq_3} = \frac{16}{3}\left(F_{a:eq_3}(m) - \frac{1}{4}\right) = -V_{3:a:eq_2} \quad (33)$$

$$V_{4:a:eq} = \begin{bmatrix} V_{4:a:eq_4} \\ V_{4:a:eq_3} \\ V_{4:a:eq_2} \end{bmatrix} = \lambda^* \begin{bmatrix} f_{4:a} \\ f_{3:a} \\ f_{3:a} \end{bmatrix} \quad (34)$$

where $F_{a:eq}(m)$ denote relative frequencies of the equal binary labels in the cliques of each family $C_a$ over a given training map m; "eq" and "ne" denote two equal or non-equal labels, respectively, for a $2^{nd}$-order clique; "eq$_i$" denote i equal labels for a $3^{rd}$- and $4^{th}$-order clique: $f_{4:a} = F_{a:eq4}(m) - \frac{1}{8}$; $f_{3:a} = F_{a:eq3}(m) - \frac{1}{2}$; $f_{2:a} = F_{a:eq2}(m) - \frac{3}{8}$; and $$\lambda^* = \frac{\sum_{a=1}^{A} f_{4:a}^2 + f_{3:a}^2 + f_{2:a}^2}{\sum_{a=1}^{A} \frac{7}{64} f_{4:a}^2 + \frac{1}{4} f_{3:a}^2 + \frac{15}{64} f_{2:a}^2} \quad (35)$$

This approximation is used for computing the higher-order spatial probabilities $Pr_{v:p}(l)$ of each label; $l \in L$.

3) Appearance-based shape prior: In addition to the distinct visual appearances, the well-known geometric shapes of medical structures can enhance the segmentation accuracy. Relying on this fact, an adaptive model of the expected kidney shape is used to both handle kidney motions, e.g., due to breathing and/or heart beating, and account for the kidney's variability due to inter-patient anatomical differences. In addition, the kidney MR images are very noisy, especially at high b-values.

Figure 21:
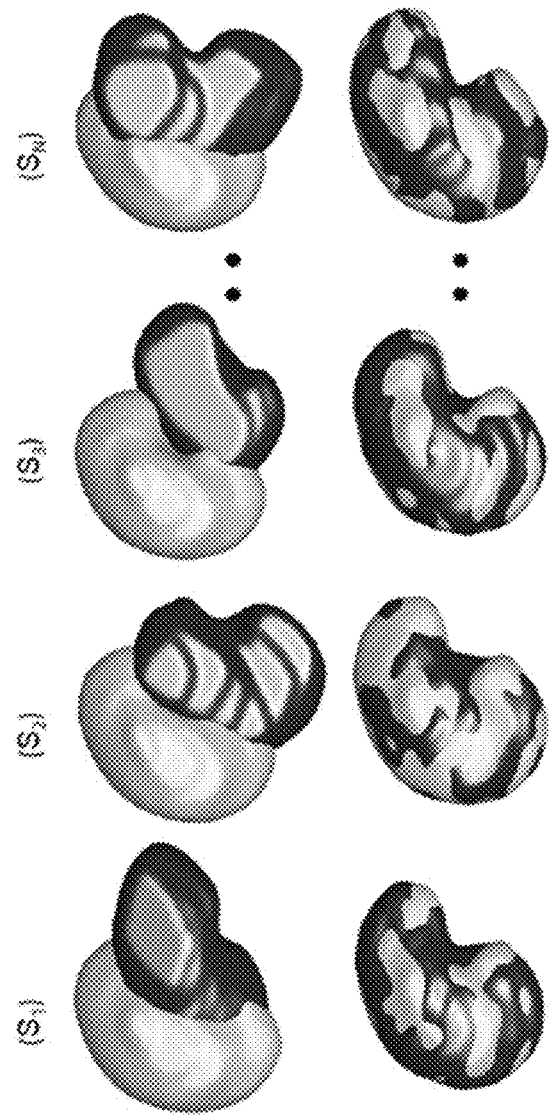
FIG. 21 provides a diagrammatic illustration of 3D co-alignment of training MRI to a single reference: the upper and lower rows present the overlapped 3D kidney volumes before and after the alignment, respectively. The reference subject appears in yellow, while the targets are shown in red.
Figure 22:
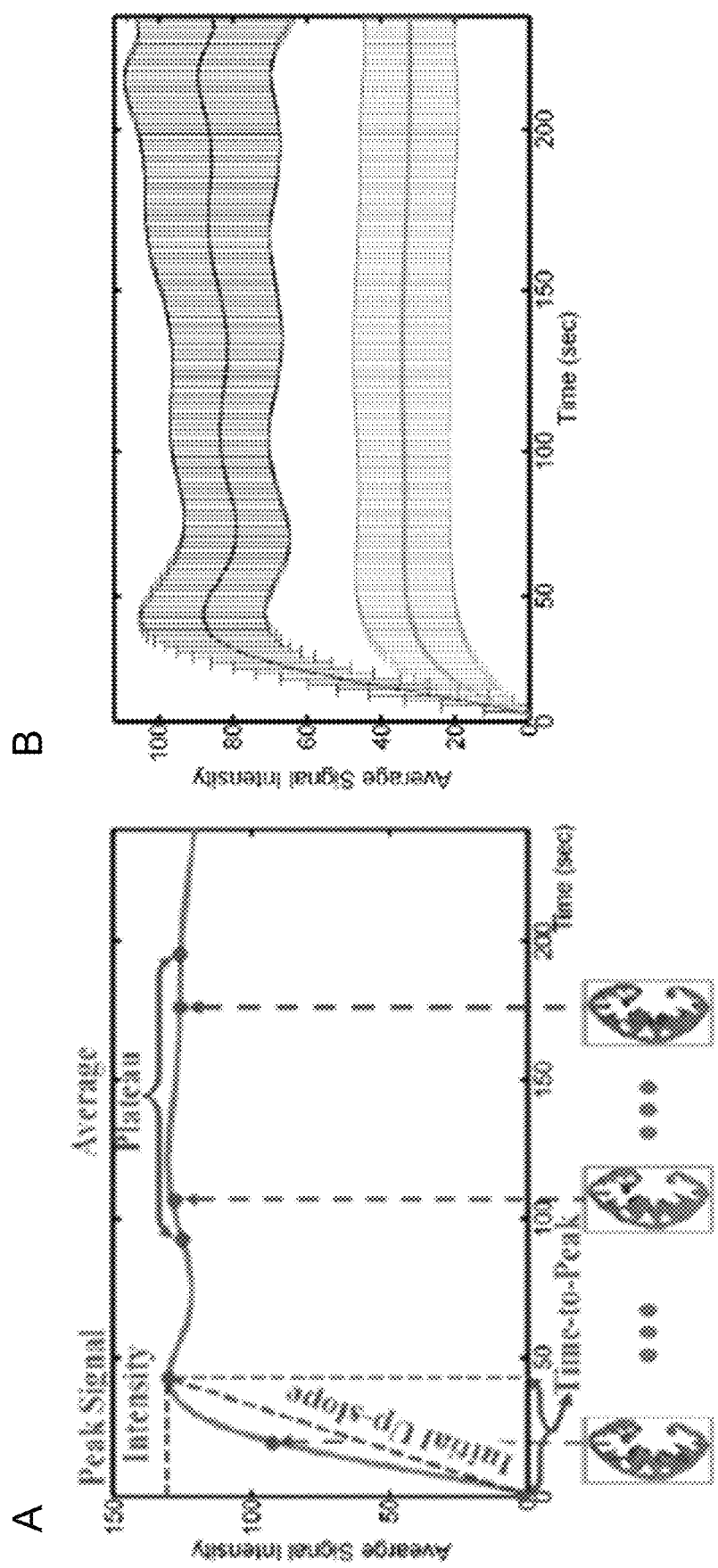
FIG. 22 depicts examples of perfusion parameters estimation from DCE-MRI data showing (A) perfusion indices represented by the constructed signal intensity-time series and (B) normalized signal intensity, averaged over the entire kidney, with respect to timing of contrast agent delivery showing a non-rejection case (line with higher average signal strength) and a rejection case (line with lower average signal strength).

To build the shape prior, the $b_0$ scans (after excluding the test subject) of kidneys formed a training database, and these images have been manually delineated by an MRI expert to get their binary kidney/background region maps. One of the images was chosen as a database reference. All other images were aligned to the reference by a non-rigid 3D B-spline transformation minimizing the sum of squared voxel-wise intensity differences between the two images. Then the kidney/background labels of the co-aligned region maps were used to learn the shape prior. FIG. 21 illustrates the co-alignment of the training MRI. Adapting the shape prior to each input MR image to be segmented is guided by the visual appearance of the latter image.

As the MR images are challenged by the motion, which might lead to different kidney masks at different b-values, each b-scan is segmented separately. The shape prior is built by segmenting manually and co-aligning the baseline scans (at $b_0$ s/mm$^2$) of all subjects. Then, the shape prior is applied to each b-scan in combination with the other estimated probabilistic models for that scan namely, the 1 st-order LCDG model of current kidney appearance, in terms of voxel-wise intensities, and the 4th-order MGRF model of spatial interactions. This joint probabilistic model provides a stochastic force that guides the evolution of a deformable boundary to segment the kidneys at that b-scan. So, the segmentation of all b-value scans uses the same shape prior, but own intensity and spatial interactions models. Algorithm 1 summarizes estimating and updating the appearance-guided shape prior for each test MR image to be segmented (the test images are first removed from the training set).

Algorithm 1 Creating/Updating the Shape Prior

1 Preprocess the training MR images by bias correction and histogram equalization
2 Construct the shape database by applying the co-alignment by Glocker et al. to the preprocessed MR images.
3 Preprocess the MR image for a test subject and co-align with the shape database
4 For each voxel, p ∈ R, in the test MR image, $g_{test}$, calculate its prior shape probabilities as follows:
  A  Use the co-aligning deformation field to relate the voxel p of the test image to the shape database lattice.
  B  Initialize a 3D window of size $N_1 \times N_2 \times N_3$, centered at the related voxel in the shape database lattice.
  C  Find within the window all the voxels with the corresponding intensity, $g_{test:p}$, in all the training images

| Algorithm 1 Creating/Updating the Shape Prior |
|---|
| D  If necessary, increase the window size and repeat Steps 4B to 4D until a non-empty set of such corresponding training intensities is found. |
| E  Estimate label probabilities based on relative occurrences of each label in all the training voxels found. |

4) Appearance- and shape-guided deformable model: Adaptation to both the kidney-background visual appearance, shape prior, and statistical spatial dependencies between kidney labels is one of the main advantages of our segmentation framework. Estimated directly from the input image and a given shape database, these properties guide the evolving deformable boundary by defining, for each voxel p with intensity $g_p=g$, the speed function of Eq. (28), $F_n(p)=\kappa\vartheta p$, where $\kappa$ is the mean contour curvature and $\vartheta p$ specifies the magnitude and direction of moving that voxel:

$$\vartheta_p = \begin{cases} -Pr_p(1) & \text{if } Pr_p(1) > Pr_p(0); \text{ i.e., } Pr_p(1) > 0.5; \\ Pr_p(0) & \text{otherwise} \end{cases} \quad (36)$$

Here, $Pr_p(0)$ and $Pr_p(1)$ are the voxel-wise background and kidney probabilities, respectively:

$$Pr_p(1) = \frac{\Omega_{kd:p}}{\Omega_{kd:p}+\Omega_{bg:p}}; \quad (37)$$

$$Pr_p(0) = \frac{\Omega_{bg:p}}{\Omega_{kd:p}+\Omega_{bg:p}} = 1 - Pr_p(1)$$

where the variables $\Omega_{kd:p}$ and $Q_{bg:p}$ for the kidney and background, respectively, depend on the voxel-wise probabilities $Pr(g|l)$; $l\in L$, for the LCDG submodels of the kidney ($l=1$) or background ($l=0$) appearance and on the kidney label probability in the MGRF spatial region map model, $Pr_{V:p}(1)$, and in the adaptive shape prior, $Pr_{sp:p}(1)$, respectively:

$$\Omega_{kd:p}=Pr(q|1)Pr_{V:p}(1)Pr_{sp:p}(1); \quad (38)$$

$$\Omega_{bg:p}=Pr(q|0)(1-Pr_{V:p}(1))(1-Pr_{sp:p}(1)) \quad (39)$$

Algorithm 2 summarizes the basic steps of the 3D level-set-based kidney segmentation.

| Algorithm 2 MRI Segmentation by Geometric Deformable Boundary |
|---|
| 1  Update the shape prior probability using Step 4 of Algorithm 1. |
| 2  Approximate the marginal of MRI intensities with the LCDG with two dominant components. |
| 3  Form an initial region map, $m_{ini}$, using the estimated shape prior and LCDG submodes of kidney and background appearances. |
| 4  Estimate the Gibbs potentials for the $4^{th}$-order spatial MGRF map model from $m_{ini}$. |
| 5  Find the above speed function, $F_n(p)$, using results of Steps 2 to 4. |
| 6  Segment the input image, g, by evolving the level-set function, $\Phi(p, nr)$, of Eq. (28) with the speed function found in Step 5. |

B. Estimating and Depicting Perfusion Parameters from DCE-MRI

Following the kidney segmentation, agent kinetic curves (signal intensity versus time curves) are constructed by estimating the average intensities over the entire cortex for each image frame of the time series (FIGS. 22A and 22B). To control for different physiological factors at different patient imaging exams, we normalized perfusion values obtained for the cortex by the perfusion of an adjacent segment of body wall muscle that was obtainable for each patient. Established dynamic perfusion analyses of extracellular extravascular agents, such as gadolinium agents, have previously used empirical parameters, including initial upslope, peak signal intensity, and time-to-peak. However, due to rapidly changing contrast agent kinetics during the transient phase, the resulting limited temporal sampling leads to noisy estimates. Therefore, agent delivery is characterized during the more slowly varying phase (plateau, or tissue distribution phase), which starts at approximately 30 seconds after injection and effectively extends to approximately two minutes for peripheral injections. This also serves to incorporate a large number of data points over the signal intensity time series to characterize perfusion.

C. Estimating and Depicting Diffusion Parameters from DW-MRI

Figure 23:
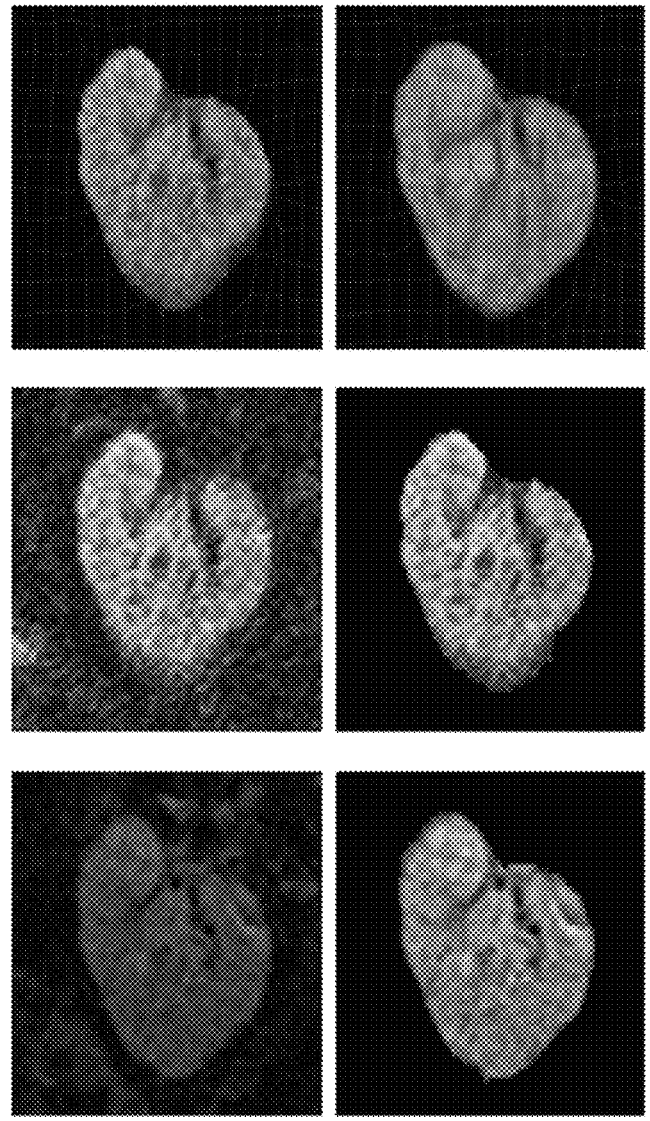
FIG. 23 depicts typical 2D cross section of the $b_0$ scan and its segmented kidney (first column), the $b_{300}$ scan and its segmented kidney (second-column), and the blending overlap before (upper-row) and after (lower-row) the non-rigid registration for motion handling (third-column).

In order to accurately evaluate image features, the segmented kidneys are processed to eliminate their motion, being a common challenge in the DW-MRI. The motion in the scans at different b-values may result in mis-overlaps of kidneys and false correspondences for the same voxel at different phases, leading to inaccurate evaluations of the discriminative features (i.e., ADCs) to be used to derive the final diagnosis. To overcome this problem, another stage of the non-rigid 3D B-spline registration is applied to both the DW-MRI scans and the segmented mask in order to map each b-value scan to the baseline $b_0$-scan. This additional registration accounts for any potential motion between the same kidney at different b-values and ensures accurate voxel-to-voxel matching for better evaluation of the ADC map. FIG. 23 shows how the non-rigid registration handles any potential misalignment of the subject's segmented kidney.

After segmenting the kidneys and excluding potential motions between the different b-value scans, their discriminatory functional features are evaluated from the images and used to distinguish between the rejected and non-rejected kidney transplants. As a transplant status feature, our CAD system uses voxel-wise ADCs:

$$ADC = \frac{1}{b_0-b}\ln\left(\frac{g_{b:p}}{g_{0:p}}\right) = \frac{\ln g_{b:p} - \ln g_{0:p}}{b_0-b} \quad (40)$$

where the segmented DW-MR images $g_0$ and $g_b$ were acquired with the $b_0$ and a different b-value, respectively.

It is worth noting that conventional classification methods that deals directly with the voxel-wise ADCs of the entire kidney volume as discriminative kidney features face two difficulties: (i) varying sizes of input data require either data truncation or zero padding for larger or smaller kidney volumes, respectively, and (ii) large data volumes lead to considerable time expenditures for training and classification.

Figure 24:
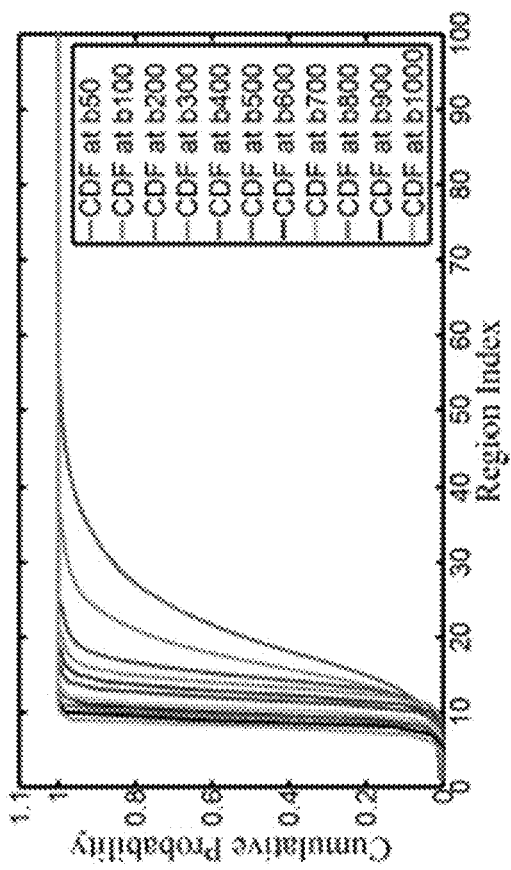
FIG. 24 provides a pair of charts depicting (left) empirical ADC distributions and (right) their cumulative distribution functions (CDFs) for one subject at the 11-different b-values.
Figure 24:
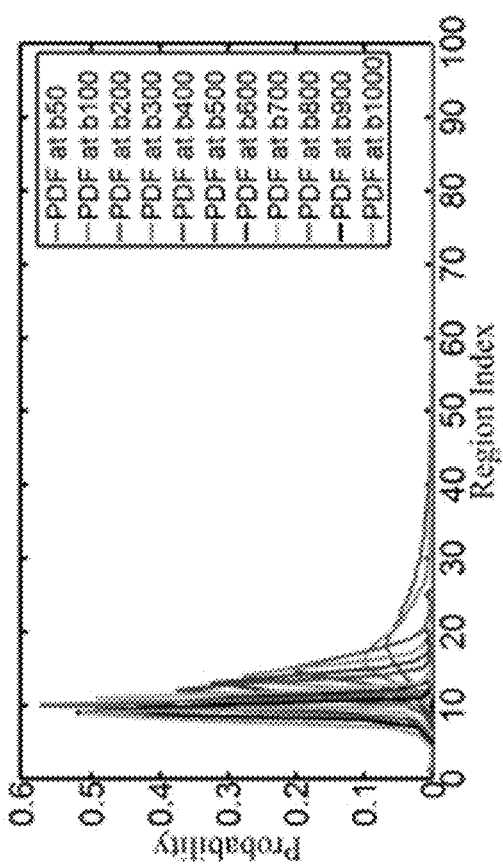

Process 610 overcomes the above challenges by characterizing the entire 3D ADC maps, collected for each subject at the 11 different b-values, by the CDFs of the ADCs, as shown in FIG. 24. The CDFs are independent of the data size and can be quantified in accordance with the actual signal-to-noise ratio (SNR) of the ADCs. Our preliminary experiments have shown that the 1%-accuracy of measuring the ADC within the actual range between the maximum and minimum ADCs for all the b-values and subjects is sufficient to maintain the final classification accuracy. Compared to the empirical probability density functions (PDFs) of the ADCs, the CDFs allow for better differentiation between the PDFs across the whole range of the ADC values. The training CDFs are used for deep learning of a stacked NCAE (SNCAE) classifier detailed in Section E. Limiting the input data size to the 11 CDFs helps to overcome the above difficulties of the arbitrary numbers of the original ADCs and notably accelerates the classification. Simultaneously, all the 3D ADCs evaluated for a certain subject can be displayed as voxel-wise parametric color-coded 3D maps to be visually assessed by radiologists.

D. Estimating and Depicting Relaxation Parameters from BOLD-MRI

Figure 25:
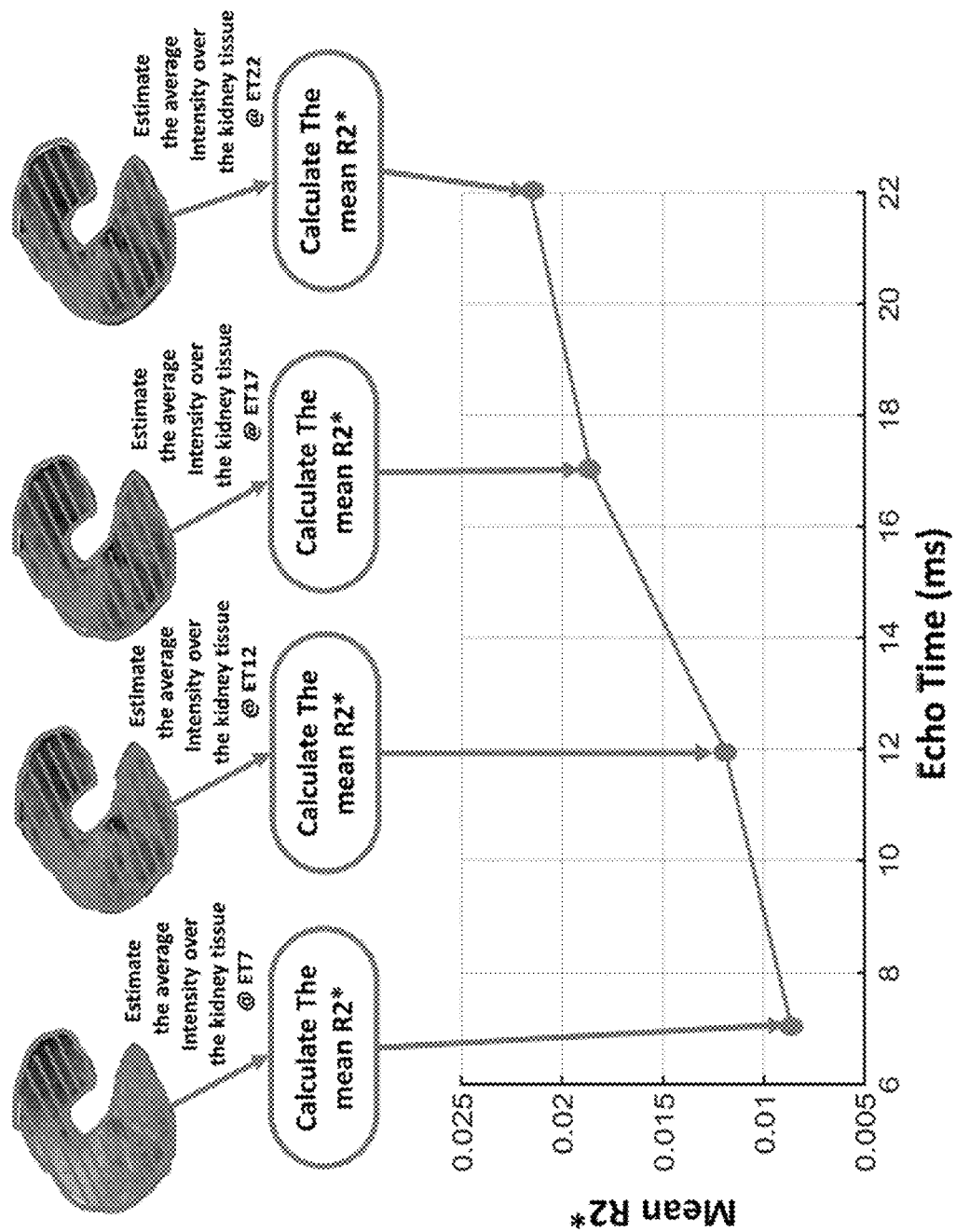
FIG. 25 is an illustrative figure depicting the process of constructing the global features by calculating the mean R2* values from the segmented kidney acquired at four different echo times (7, 12, 17, and 22 msec).
Figure 26:
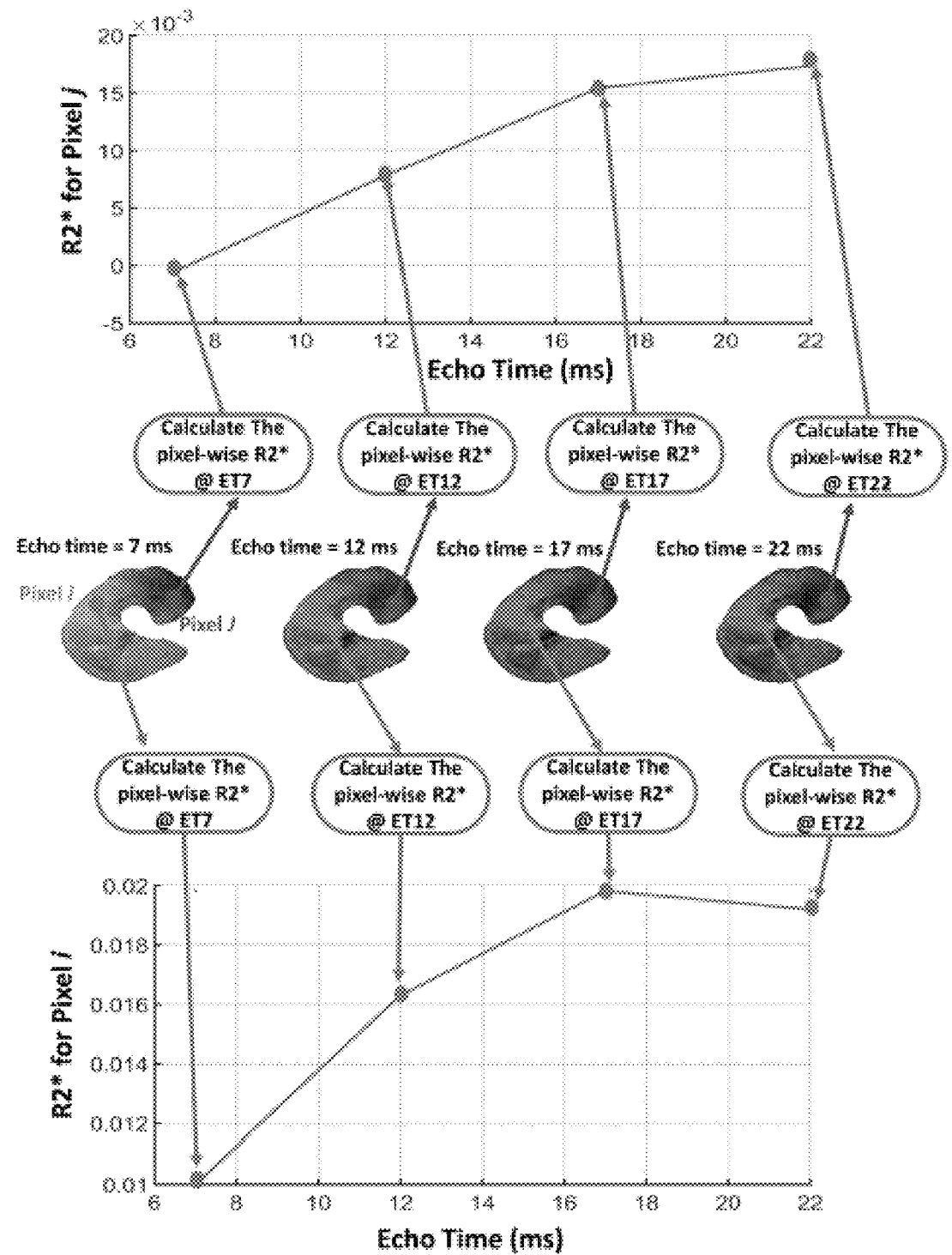
FIG. 26 is an illustrative figure depicting the process of constructing the local features by calculating the pixel-wise R2* values from the segmented kidney at four different echo times (7, 12, 17, and 22 msec) for representative pixels i and j.

In some embodiments, renal function is evaluated by quantifying the amount of deoxygenated hemoglobin in the kidney. BOLD measures T2*, which is the amount of oxygenated hemoglobin in the kidney. R2* (deoxygenated hemoglobin) is the reciprocal of T2* and will be used as our BOLD marker. After segmentation, the global features (i.e. mean R2* over the entire kidney) and the local features (i.e. pixel-wise R2*) are estimated at multiple different echo-times (e.g., 7, 12, 17, and 22 ms, as shown in FIG. 25). These R2* values are used as BOLD-MR image-markers for renal transplant status assessment, while the BOLD-MRI data acquired at echo-time=2 ms was used as the baseline. The pixel-wise T2* maps can be calculated using the following equation as:

$$T2_p^* = \frac{t_0 - t}{\ln(SI_{t:p} - SI_{t_0:p})} \quad (41)$$

while the amount of deoxyhemoglobin (apparent relaxation rate (R2*)) is the reciprocal of T2* and can be calculated using the following equation:

$$R2_p^* = \frac{1}{T2_p^*} \quad (42)$$

p: a pixel at a location with its 2D coordinates (x, y).
SIt: the signal intensity of the pixel (p) of the segmented BOLD-MR image obtained at the echo-time (t ms).
$SI_{t_0}$: the signal intensity of the pixel (p) of the segmented BOLD-MR image obtained at the baseline echo-time ($t_0$=2 ms).

After obtaining the global (i.e. mean R2*) and local features (i.e. pixelwise R2*), two stages of classification were employed using artificial neural networks (ANNs) to obtain the final diagnosis. The first stage uses the global features, shown in FIG. 25, extracted from all subjects, along with a leave-one-subject-out (LOSO) cross validation approach to train and validate an ANN classifier, shown in FIG. 27, with two hidden layers (the first layer with 10 nodes and the second layer with 5 nodes) to obtain a global diagnosis for the entire kidney.

Figure 27:
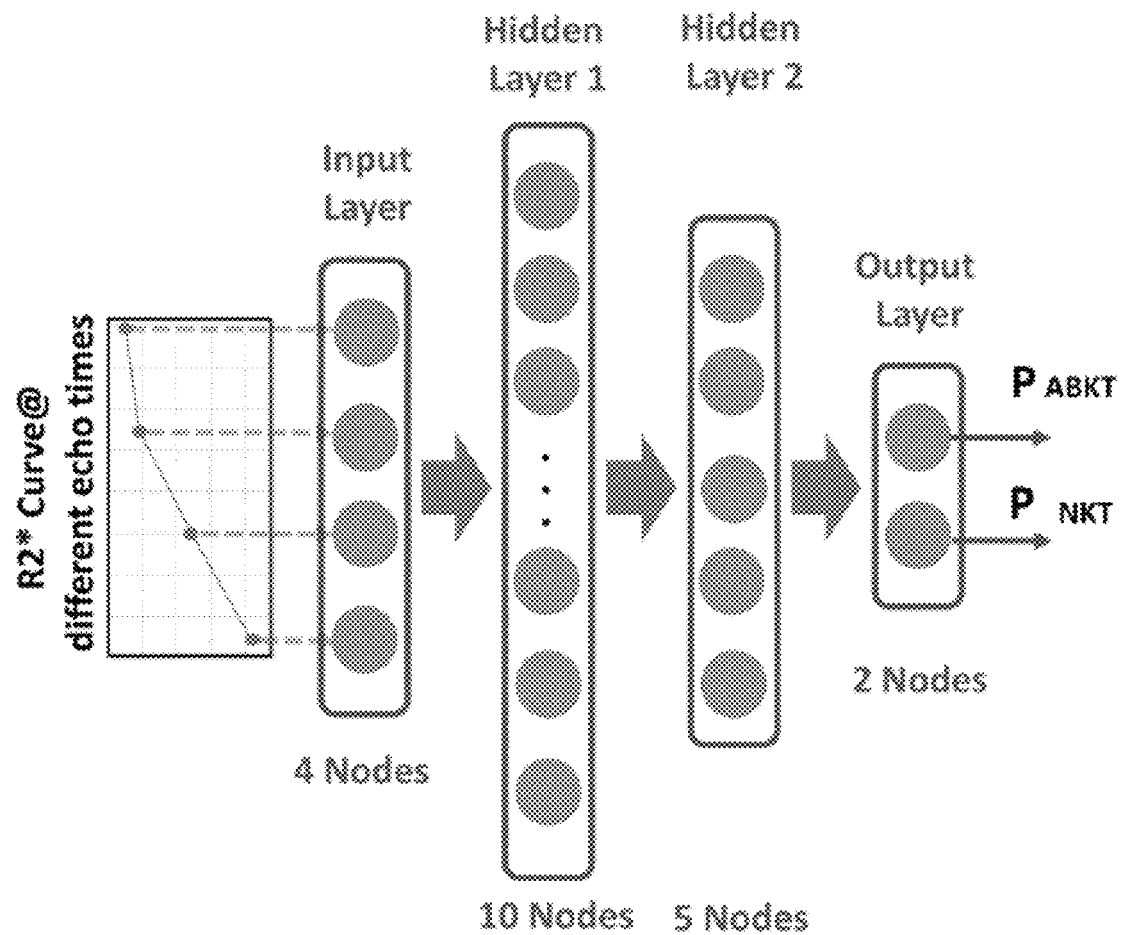
FIG. 27 is a block diagram of an artificial neural network (ANN) and classification process, wherein the global and local features are input into the ANN and the ANN outputs probabilities of the imaged kidney being a normal kidney transplant (NKT) or an abnormal kidney transplant (ABKT).
Figure 28:
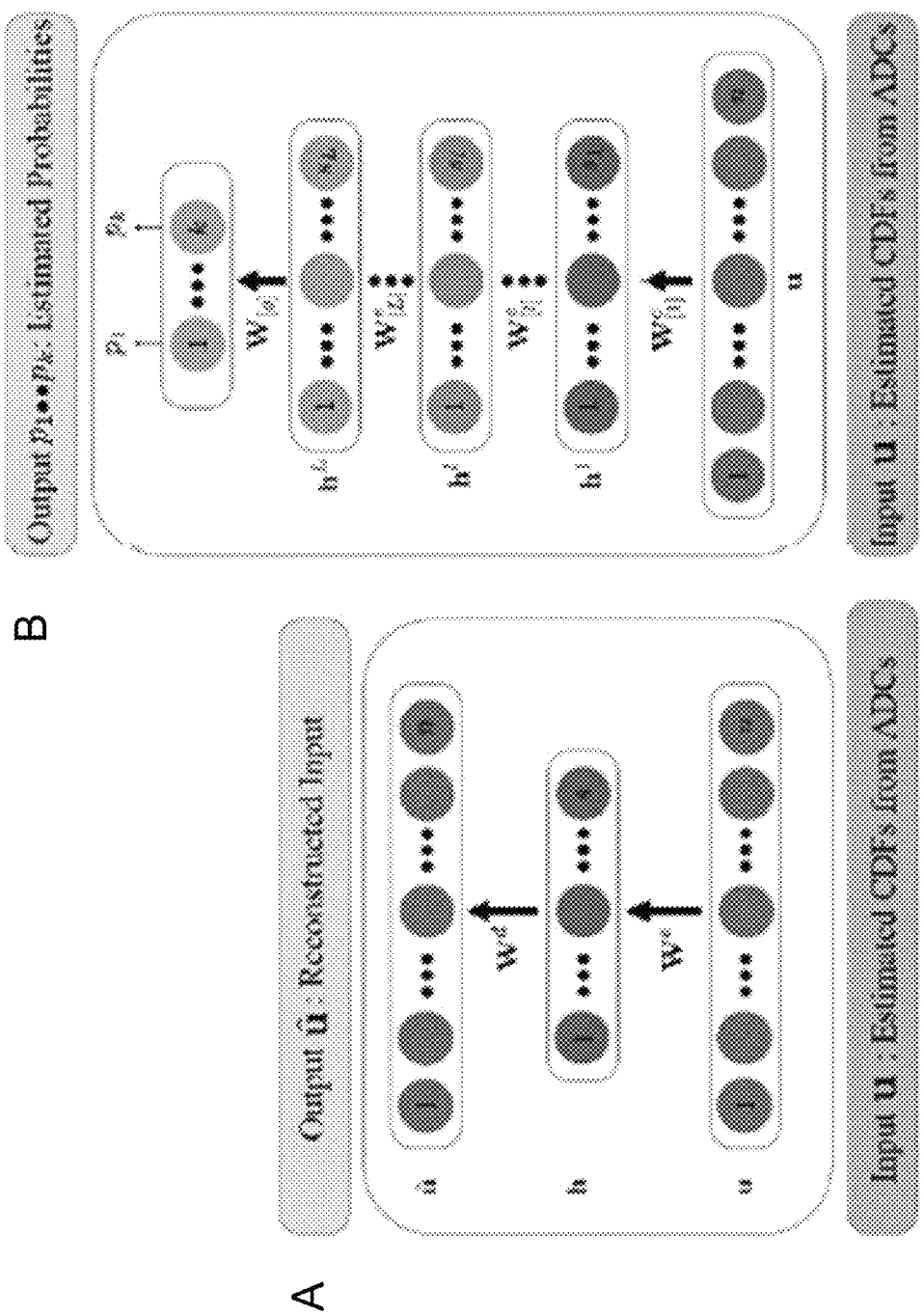
FIG. 28 is a block diagram of (A) an NCAE classifier and (B) a SNCAE classifier.

The classification model obtained from the first stage was then tested using local features (see FIG. 26) to obtain a pixel-wise probabilistic map representing the probability of each pixel being NKT or ABKT, for a local diagnosis, as shown in FIG. 27.

E. Autoencoding and Deep Learning Based Classifier

The process 610 utilizes a learnable classifier for kidney transplantation prediction using clinical and image bio-marker data. In some embodiments, this learnable classifier is an artificial neural network (ANN). While other learnable classifiers may be used, ANN are preferred in some embodiments due to (i) automated dimensionality reduction of large scale data; (ii) automatic extraction of more discriminatory features between classes through hierarchical feature extraction (in this case, the high level (global) features are derived from the low level (local) features for model training); and (iii) flexibility compared to the classical shallow models, i.e. a classifier (e.g., a softmax-based or SVM-based) can be built on the extracted features from the deep learning ANN. In some embodiments, the process 610 includes deep learning and auto-encoders with non-negativity constraint (NCAE) as a core ANN architecture for pre-training and classification to distinguish between the nonrejection and acute rejection of kidney transplants. In particular, the process 610 employs a deep neural network with a stack of auto-encoders (AE) before the output layer that computes a softmax regression, generalizing the common logistic regression to more than two classes. Each AE compresses its input data to capture the most prominent variations and is built separately by greedy unsupervised pre-training. The softmax output layer facilitates the subsequent supervised back-propagation-based fine tuning of the entire classifier by minimizing the total loss (negative log-likelihood) for a given training labeled data. Using the AEs with a non-negativity constraint (NCAE) yields both more reasonable data codes (features) during its unsupervised pre-training and better classification performance after the supervised refinement.

Let W={We, Wd: j=1, . . . , s; i=1, . . . , n} be a set of column vectors of weights for encoding (e) and decoding (d) layers of a single AE in FIGS. 28A and 28B. The AE converts an n-dimensional column vector u=[$u_1$, . . . , $u_n$]T of input signals, where T denotes vector transposition, into an s-dimensional column vector h=[h1, . . . , hs]T of hidden codes (features, or activations), such that s<<n, by a uniform nonlinear transformation of s weighted linear combinations of signals:

$$h_j = \sigma((W_j^e)^T u) \equiv \sigma\left(\sum_{i=1}^n w_{j,i}^e u_i\right) \quad (43)$$

where σ( . . . ) is a certain sigmoid, i.e. a differential monotone scalar function with values in the range [0,1]. Unsupervised pre-training of the AE minimizes total deviations between each given training input vector $u_k$, k= 1, . . . , K, and the same-dimensional vector, $\hat{u}w_{:k}$ reconstructed from its code, or activation vector, $h_k$ FIG. 12(a)). The total reconstruction error of applying such AE to compress and decompress the K training input vectors integrates the $l_2$-norms of the deviations:

$$J_{AE}(W) = \frac{1}{2K} \sum_{k=1}^K \|\hat{u}_{W:k} - u_k\|^2 \quad (44)$$

To reduce the number of negative weights and enforce sparsity of the NCAE, the reconstruction error of Eq. (44) is appended, respectively, with quadratic negative weight penalties, f($w_i$)=(min{0, $w_i$})²; i=1, . . . ,n, and Kullback-Leibler (KL) divergence, $J_{KL}(\gamma\|hw^e)$, of activations, $hw^e$, obtained with the encoding weights $W^e$ for the training data, from a fixed small positive average value, γ, near 0:

$$J_{NCAE}(W) = J_{AE}(W) + \alpha \sum_{j=1}^{s}\sum_{i=1}^{n} f(w_{j:i}) + \beta J_{KL}(\gamma \| h_{w^e}) \quad (45)$$

Here, the factors a≥0 and β≥0 specify relative contributions of the non-negativity and sparsity constraints to the overall loss, $J_{NCAE}(W)$, and $J_{KL}(\gamma\|hw^e)=$ $$J_{KL}(\gamma\|h_{w^e}) = \sum_{j=1}^{s} h_{w^e:j}\log\left(\frac{h_{w^e:j}}{\gamma}\right) + (1 - h_{w^e:j})\log\left(\frac{1-h_{w^e:j}}{1-\gamma}\right) \quad (46)$$

The classifier is built by stacking the NCAE layers with an output softmax layer, as shown in FIG. 28B. Each NCAE is pre-trained separately in the unsupervised mode by using the activation vector of a lower layer as the input to the upper layer. In our case, for the DW-MRI, initial input data consisted of 11 CDFs, each of size 100, i.e. n=1100. In other words, for quantizing the ADCs, the range between the minimum and maximum ADCs for all the input data sets (i.e. all the sets for 11 b-values and 64 subjects) was divided into 100 steps to keep the chosen 1%-accuracy of initial ADC measurements. The PDFs and then CDFs of the ADCs were built for these quantized values. The bottom NCAE compresses the input vector to $s_1$ first-level activators, compressed by the next NCAE to $S_2$ second-level activators, which are reduced in turn by the output softmax layer to $s^o$ values. The number of the NCAE layers and successive data compression ratios for each layer were chosen empirically, on the basis of comparative experiments.

Separate pre-training of the first and second layers by minimizing the loss of Eq. (45) reduces the total reconstruction error, as well as increases sparsity of the extracted activations and numbers of the non-negative weights. The activations of the second NCAE layer, $h[2]=\sigma(W^e_{[2]}{}^T h^{[1]})$, are inputs of the softmax classification layer, as sketched in FIG. 28B to compute a plausibility of decision in favor of each particular output class, c=1, 2.

$$p(c; W^{o:c}) = \frac{\exp(W^T_{o:c} h^{[2]})}{\exp(W^T_{o:1} h^{[2]}) + \exp(W^T_{o:2} h^{[2]})}; \quad (47, 48)$$

$$c = 1, 2 \text{ and } \sum_{c=1}^{2} p(c; W_{o:c}; h^{[2]}) = 1.$$

Its separate pre-training minimizes the total negative log-likelihood $J_o(W_o)$ of the known training classes, appended with the negative weight penalties:

$$J_o(W^o) = -\frac{1}{K}\sum_{k=1}^{K} \log p(c_k; W_{o:c}) + a\sum_{c=1}^{2}\sum_{j=1}^{s_2} w_{o:c_3}$$

---

Algorithm 3 Kidney Transplant Status Classification and PIS, ADC, and R2* Color Mapping 1 Calculate, using Eq. (40), the ADCs from DW-MRI at different b-values, and/or PIs from DCE-MRI for different time sequences and R2* from BOLD-MRI at different echo times for the entire transplanted kidney of each subject.

---

Algorithm 3 Kidney Transplant Status Classification and PIS, ADC, and R2* Color Mapping 2 Classification:
  A  Construct the CDFs of the calculated ADCs from DW-MRI at different
     b-values and/or PIs from DCE-MRI for different time sequences and
     over the entire kidney volume and R2* maps from BOLD-MRI at different echo times for the entire transplanted kidney of each subject.
  B  Use a SNCAE-based deep ANN classifier trained by unsupervised pre-
     training and supervised fine tuning together with a leave-one-subject-
     out (LOSO) approach to discriminate normal from abnormal transplant
     status and get the final diagnosis. If the transplant is classified as
     abnormal, then use thee SCNAE of the second stage to classify the
     abnormal transplant as a DRD or AR renal allograft.
3 Generation of color ADC maps: Generate voxel-wise color-coded maps of
  the PIs, ADCs, and R2* calculated in Step 1 to demonstrate visually
  perceived differences between the normal and abnormal states of kidney
  transplants.

---

Finally, the entire stacked NCAE classifier (SNCAE) is fine-tuned on the labeled training data by the conventional error back-propagation through the network and penalizing only the negative weights of the softmax layer. The network was trained and tested based on a leave-one-out scenario, so that the test accuracies were averaged to estimate the overall accuracy of the classifier. These experiments were conducted for different structures and parameters of the classifier. In one embodiment, the two-layer SNCAE with $s_1$=50, $S_2$=5, $s^o$=2, α=3*10$^{-5}$, β=3, and γ=0.1 gave the best diagnostic accuracy and was accepted for the proposed CAD system. Algorithm 3 summarizes classification of kidney transplant status and generation of color ADC maps.

Figure 29:
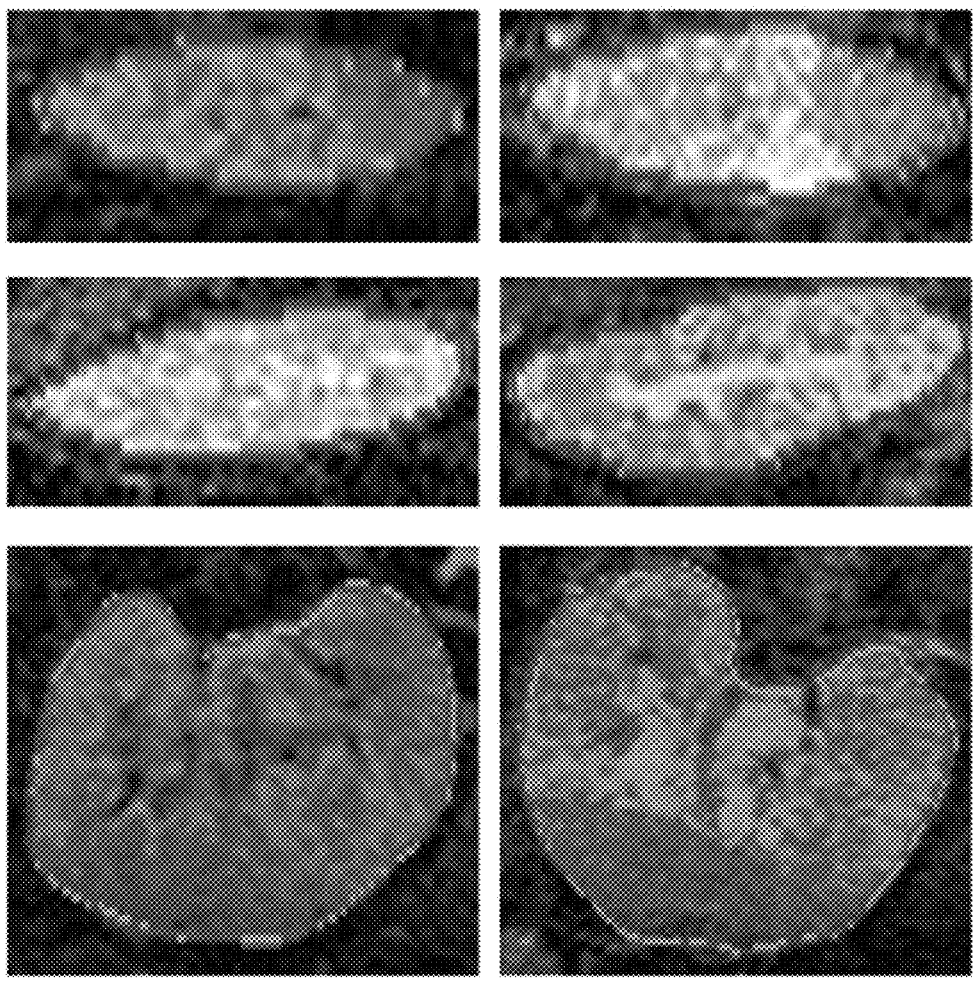
FIG. 29 depicts an example of segmentation of MRI images according to the second method disclosed herein (red) with respect to the expert's manual ground truth (green): the coronal (left column), axial (middle column), and sagittal (right column) cross-sections for two subjects, $S_1$ and $S_2$.

Segmentation results: The performance of the proposed segmentation was tested first on the collected DW-MRI data (total of 103 subjects), the DCE-MRI data (total of 50 subjects), and the BOLD-MRI data (Total of 19 subjects). FIG. 29 shows some segmentation results for different kidney cross-sections (coronal, axial, and sagittal) for two subjects at $b_0$. The segmentation accuracy was evaluated by three volumetric measures, namely, the Dice similarity coefficient (DSC) in Eq. (49) and percentage kidney volume difference (PKVD) in Eq. (50), volume overlap ratio (VOR) in Eq. (51), and one distance-based metric—the 95-percentile modified Hausdorff distance (MHD) in Eqs. (52,53), which characterize the spatial overlap and distribution of the surface to surface distances between the segmented and ground truth kidneys, respectively. The ground truth kidney maps were manually outlined by an MRI expert (a board certified radiologist)

$$DSC = \frac{2TP}{2TP + FP + FN} \quad (49)$$

where TP, FP, and FN denote the true positive, false positive, and false negative respectively. Better segmentation is indicated is indicated by higher DSC values (ideal segmentation is indicated by a DSC value of one). If there is no overlap, DSC will be assigned a value of zero.

$$PKVD\ \% = \frac{|GT| - |SR|}{|GT|} * 100 \qquad (50)$$

where |GT| and |SR| indicate the total number of voxels in the ground rush and the segmented region, respectively.

$$VOR(GT, SR) = \frac{|GT \cap SR|}{\min(|GT|, |SR|)} \qquad (51)$$

If set GT is a subset of SR or the converse, then the overlap coefficient is equal to one.

$$HD(A_1, A_1) = \max_{c \in A_1} \{\min_{e \in A_2} \{d(c, e)\}\} \qquad (52)$$

where c and e denote points of set A1 and A2 respectively, and d(c, e) is the Euclidean distance between c and e. The Modified bidirectional HD (M H $D_{Bi}$) between SR and its GT is defined as:

$$MHD_{Bi}(GT,SB) = \max\{HD(GT,SB), HD(SB,GT)\} \qquad (53)$$

Figure 30:
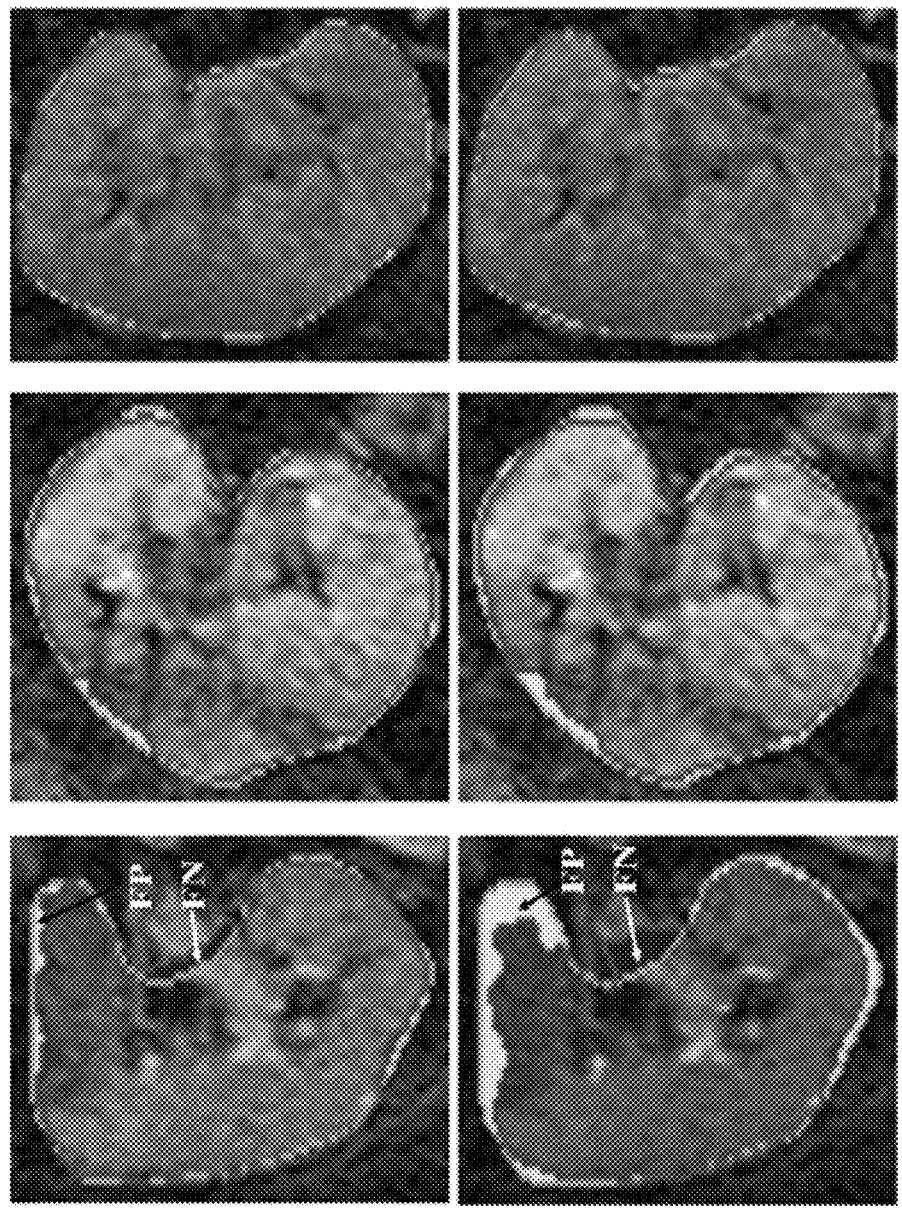
FIG. 30 depicts an example of segmentation of MRI images according to the second method disclosed herein (red) with respect to the expert's manual ground truth (green) using the $4^{th}$-order MGRF (top row) compared to the first method disclosed herein using the $2^{nd}$-order MGRF (second row) for three different subjects (each column a different subject), where the first, second, and third columns show comparatively large, moderate, and small differences (yellow or false positive (FP) and blue or false negative (FN) regions), respectively.

To show the effect of adding the higher-order MGRF model to our segmentation, we compared the current results with our previous segmentation using the 2nd order—MGRF, as shown in FIG. 30. In addition, Table I compares both segmentation methods in terms of the DSC, MHD, VOR, and PKVD metrics. As shown in FIG. 30 and documented in Table I, the disclosed segmentation method has been notably enhanced after adding the higher-order MGRF. Without being bound by theory the $4^{th}$-order MGRF may be more capable of capturing more intricate inhomogeneities of qrey levels between different structures, e.g. cortex and medulla.

TABLE I

Segmentation accuracy by the DSC, MHD (mm), VOR, and PKVD (%).

| Metric | $2^{nd}$-MGRF [49], [50] | | | $4^{th}$-MGRF | | |
|---|---|---|---|---|---|---|
| | Min | Max | mean ± SD | Min | Max | mean ± SD |
| DSC | 0.89 | 0.96 | 0.93 ± 0.17 | 0.92 | 0.97 | 0.96 ± 0.04 |
| MHD (mm) | 4.00 | 8.00 | 5.43 ± 1.70 | 2.50 | 6.37 | 4.00 ± 0.77 |
| VOR | 0.88 | 0.98 | 0.93 ± 0.03 | 0.93 | 0.99 | 0.97 ± 0.16 |
| PKVD (%) | 7.00 | 19.6 | 13.8 ± 2.90 | 5.50 | 16.0 | 9.3 ± 2.50 |

Figure 31:
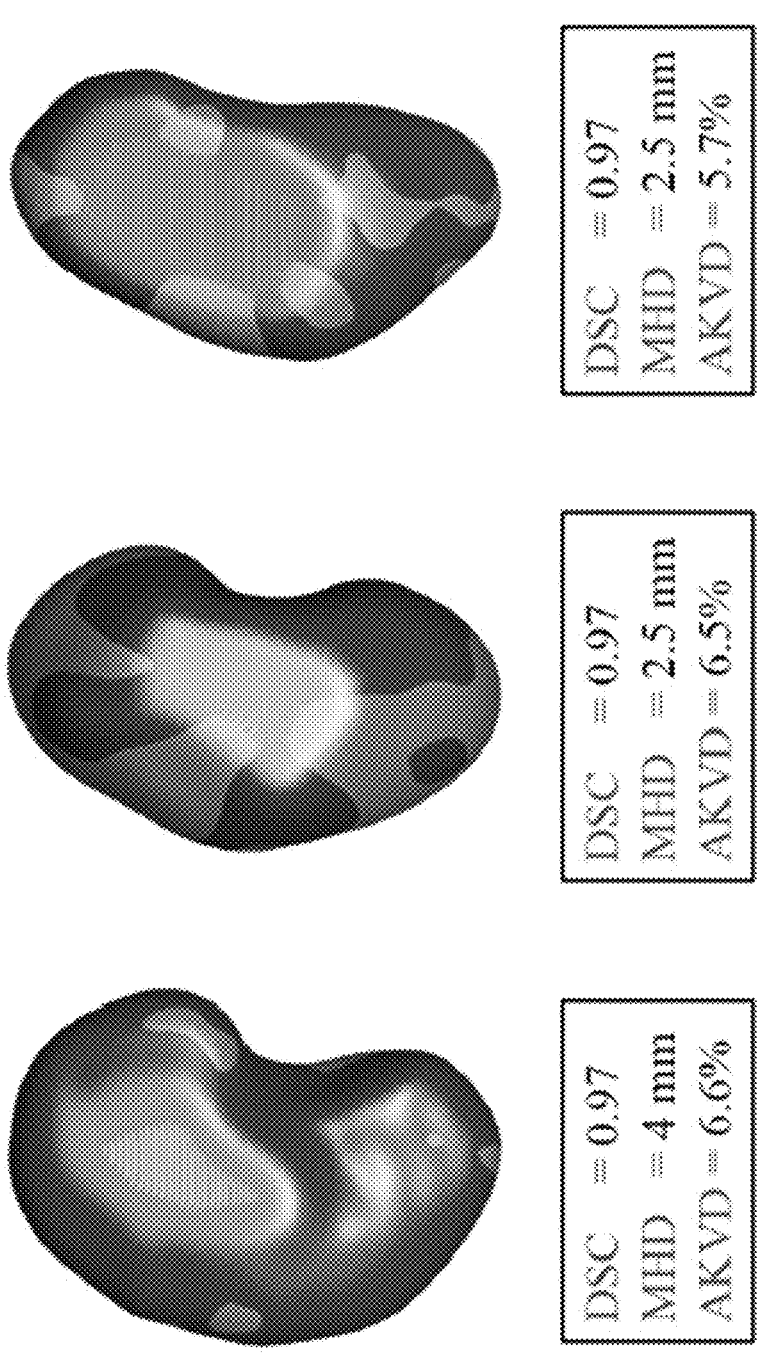
FIG. 31 provides diagrammatic illustrations comparing 3D segmentation according to the second method (red) with respect to the expert's manual ground truth (green) for three subjects with the associated accuracy scores.
Figure 32:
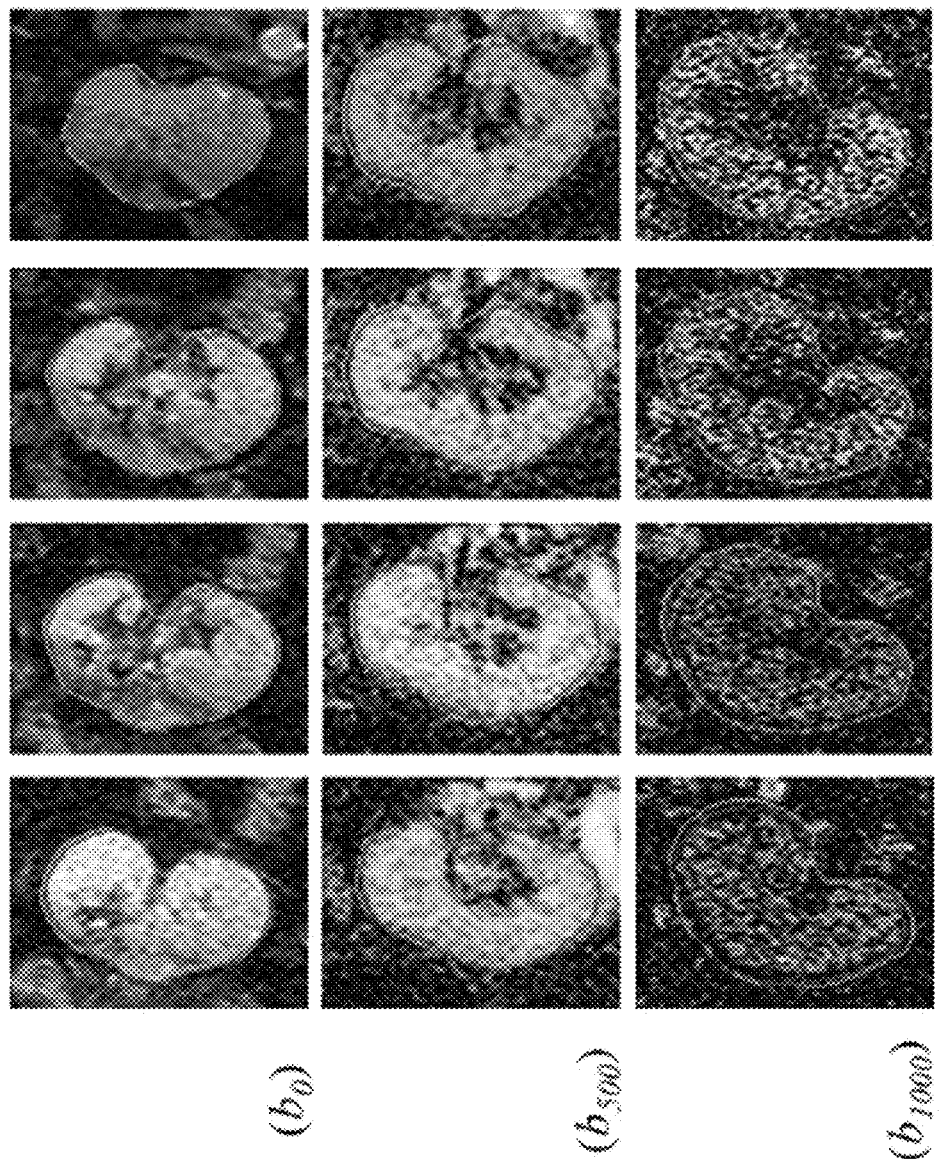
FIG. 32 depicts image data comparing four coronal cross-sections (columns) for our segmentation of the DW-MRI acquired at different b-values s/mm$^2$ (red: our method, green: expert's manual ground truth).

All metrics are represented by the minimum (Min), (Max), and Mean ± Standard Deviation Values FIG. 31 shows 3D segmentation results for three subjects with their evaluation metrics. In particular, the developed segmentation proved its ability to precisely segment the kidney at higher b; values. Shown in FIG. 32, coronal cross-sectional segmentation results for three other subjects at $b_0$ and higher $b_i$ values ($b_{500}$ and $b_{1000}$) also confirm the high accuracy and robustness to noise of our segmentation.

Diagnostic results: To evaluate the ability of process 610 to differentiate ABKT from NKT kidney transplant status, its accuracy is tested using (i) the clinical biomarkers alone, which the current clinical approach uses for diagnosis, (ii) the MRI-derived biomarkers, and (iii) the fusion/integration of both the clinical and the MRI-derived biomarkers. For the DCE-MRI the transplant status is characterized using the TIPCs-estimated biomarkers, which are calculated for all 50 patients and are fused/integrated with CrCl and SPCr for classification. To distinguish between NKT and ABKT cases a SNCAE-based classifier using a LOSO approach is used. On the other hand, the 103 DW-MRI patients are classified based on the fusion/integration of the calculated CDFs of the ADCs with CrCl and SPCr using the LOSO approach and a SNCAE-based classifier. The diagnostic accuracies including the sensitivity, specificity, and accuracy for the DCE-, DW-, and BOLD-MRI data are shown in Table II, Table III, and Table IV, respectively.

As shown in Tables II and III the accuracy based on the clinical biomarkers is very low for both DCE-MRI and DW-MRI, which is mainly due to the large overlap of these biomarkers between both groups. Secondly, classification based on image biomarkers has higher accuracy compared to that based on clinical biomarkers. To show the advantages of fusing/integrating both clinical and image biomarkers, the kidney status was also assessed by augmenting the classifier with both biomarkers and the same LOSO. As expected, the overall accuracy notably increases after fusion/integration of both types of biomarkers, as evidenced in Tables II & III.

TABLE II

Diagnostic accuracy using DCE-MRI individual parameters and clinical biomarkers. Note that, "SENS," "SPEC," and "ACC" stand for sensitivity, specificity, and overall accuracy

| | SENS (%) | SPEC (%) | ACC (%) |
|---|---|---|---|
| DCE-MRI Biomarkers | | | |
| Peak value | 97.00 | 89.00 | 92.00 |
| Time-to-peak | 70.00 | 96.00 | 80.00 |
| Initial up-slope | 97.00 | 93.00 | 94.00 |
| Average plateau | 91.00 | 81.00 | 84.00 |
| Clinical Biomarkers | 91.00 | 81.00 | 84.00 |
| Fused Biomarkers | 100.00 | 96.00 | 98.00 |

TABLE III

Diagnostic accuracy for our CAD system using clinical and MRI-driven biomarkers. Note that, "SENS," "SPEC," and "ACC" stand for sensitivity, specificity, and overall accuracy.

| | SENS (%) | SPEC (%) | ACC (%) |
|---|---|---|---|
| DW-MRI Biomarkers | 92.00 | 94.00 | 94.00 |
| Clinical Biomarkers | 76.00 | 44.00 | 66.00 |
| Fused Biomarkers | 96.00 | 100.00 | 97.00 |

Figure 33:
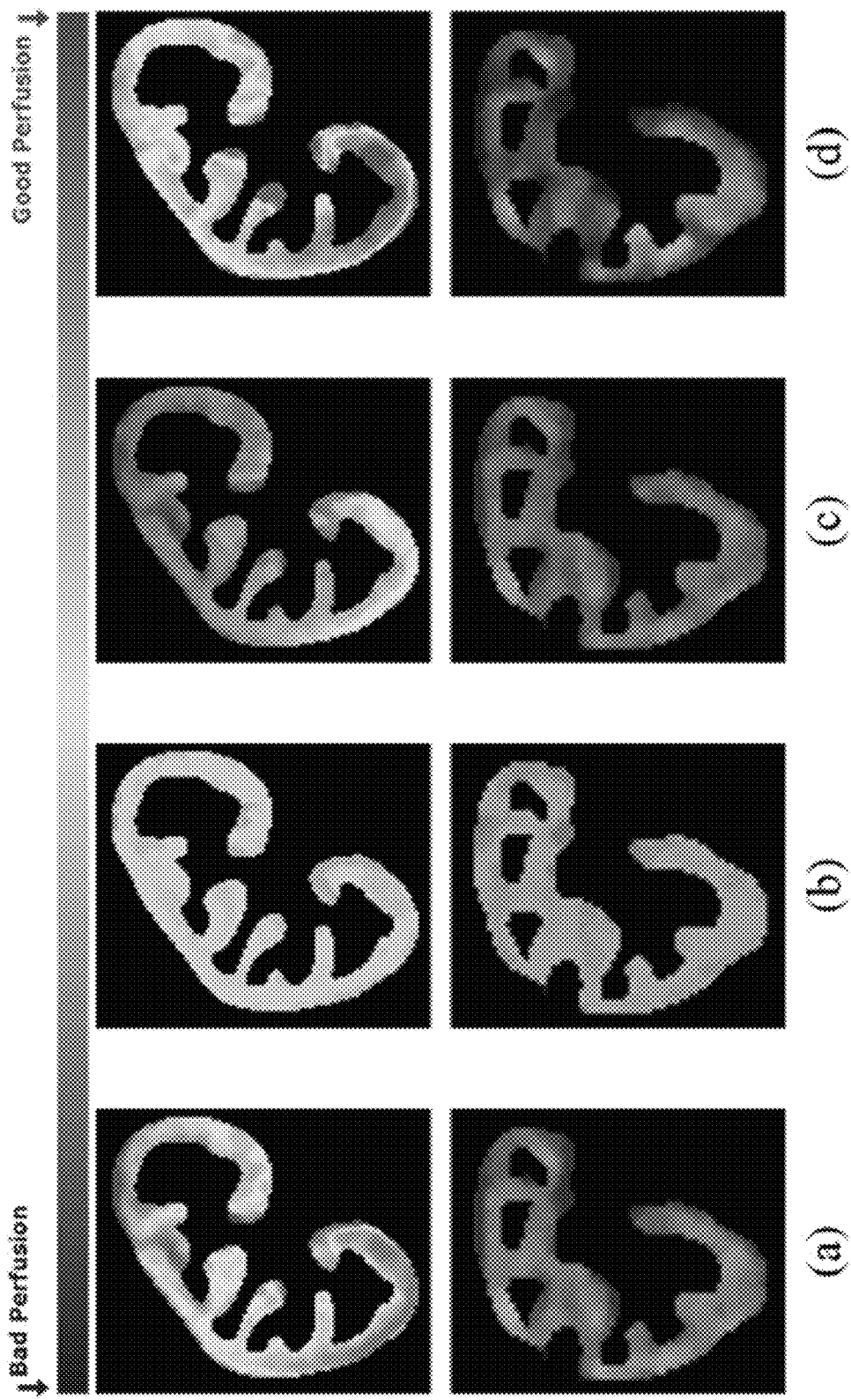
FIG. 33 depicts perfusion maps for the four perfusion indexes: peak signal intensity (a); time-to-peak (b); initial up-slope (c), and average plateau (d) for a representative non-rejection case (upper row) and an acute rejection case (lower row). The red and blue hues of each color scale correspond to highest and lowest values, respectively.
Figure 34:
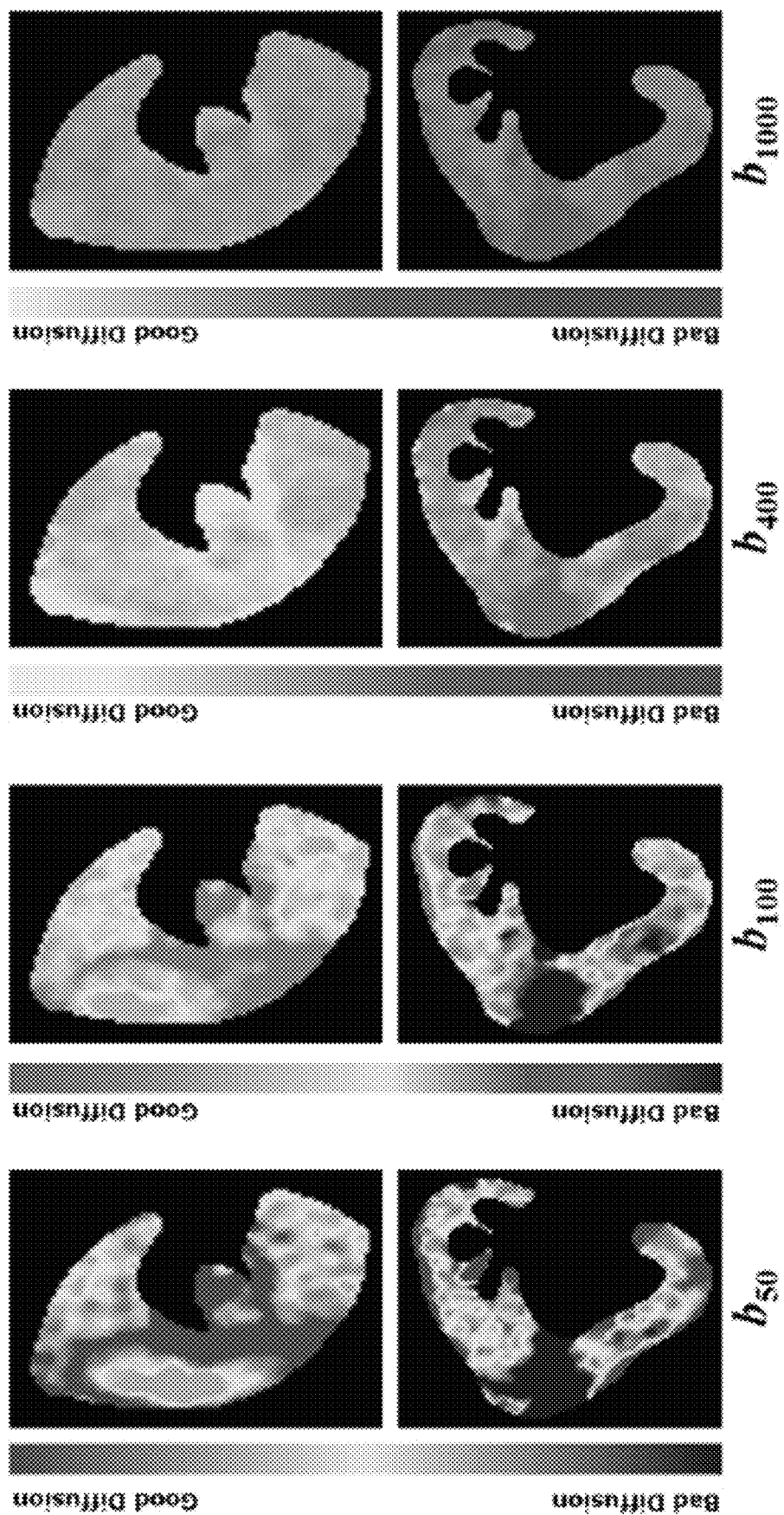
FIG. 34 depicts a sample of voxel-wise parametric-maps constructed for DW-MRI data at different b-values for a non-rejection/normal case in the top row and an abnormal case in the bottom row. Here, we have different color-codes representing the blood diffusion rate at each b-value.
Figure 35:
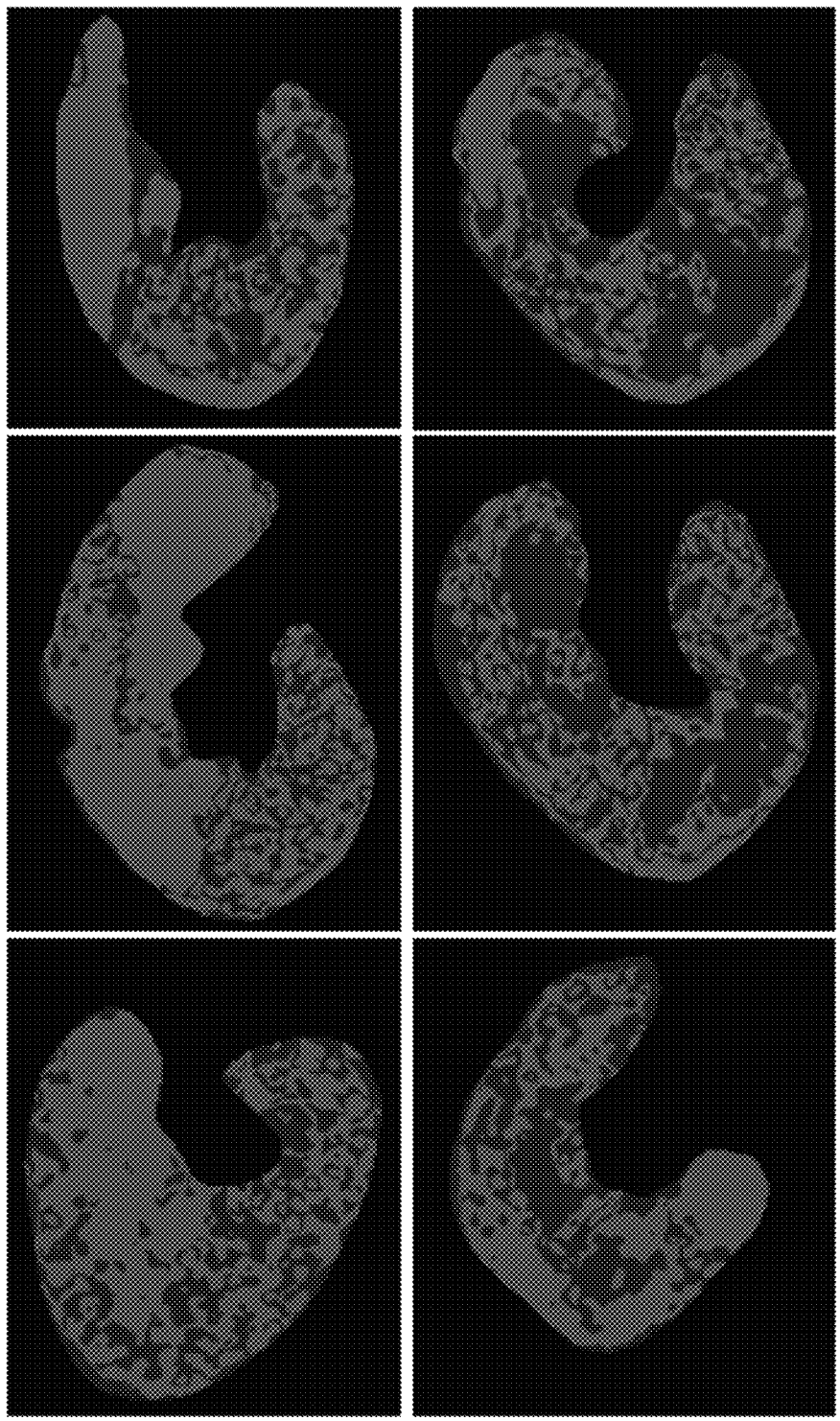
FIG. 35 depicts pixel-wise color-coded probabilistic maps obtained from the local feature analysis. The upper row displays NKT and the lower row displays ABKT. Red color indicates the probability of being NKT and blue color indicates the probability of being ABKT.

In addition to the global diagnosis of the transplant status as normal/nonrejection or abnormal, process 610 is also designed to demonstrate the local (pixel/voxel-wise) perfusion/diffusion of the registered data as color maps. These regional display mapping are of great importance for the radiologists to help investigate which region of the kidney needs attention and follow-up with appropriate treatment. FIG. 33 demonstrates the parametric maps for the four indexes-peak signal intensity (a), time-to-peak (b), initial up-slope (c), and average plateau (d) for a non-rejection case (upper row) and an acute rejection case (lower row). Similar to DCE-MRI, the voxel-wise diffusion of the transplanted kidney is displayed as parametric color-coded maps, as shown in FIG. 34. For the local features (i.e. the pixel-wise R2* maps), extracted from BOLD-MRI, were used to test the ANN classification model resulting in a pixel-wise probabilistic map for each kidney. The local features analysis outputs the probability of each pixel in the kidney to be ABKT or NKT. These probabilistic maps were then color-coded to assist in the visualization of the local kidney function by the clinicians, as shown in FIG. 35. The local features analysis will also enable tracking of the progression of ABKT or improvement with treatment during follow up. The data in FIGS. 33, 34, and 35 reveal the expected relation of the MRI parameters for NKT versus ABKT status.

TABLE IV

Diagnostic accuracy for our CAD system using BOLD-MRI-driven markers and clinical biomarkers. Note that, "SENS," "SPEC," and "ACC" stand for sensitivity, specificity, and overall accuracy.

|  | SENS (%) | SPEC (%) | ACC (%) |
|---|---|---|---|
| BOLD-MRI Biomarkers | 89.00 | 80.00 | 89.00 |
| Clinical Biomarkers | 67.00 | 70.00 | 68.00 |
| Fused Biomarkers | 100.0 | 90.00 | 95.00 |

Following the first SNCAE-based classification stage and starting with the 1.5 T DW-MRI data (total of 66) and 3 T DW-MRI data (total of 37), process 610 assesses the ABKT transplant status with a second-stage SNCAE-based classifier using the constructed CDFs and the clinical biomarkers. A leave-one-subject-out (LOSO) approach is applied to distinguish between acute rejection (AR) from different renal disease (DRD). First, accuracy was evaluated using the clinical biomarkers alone. As demonstrated in Table V, diagnostic accuracy using the clinical biomarkers only is very low due to the large overlap of these biomarkers between NKT and ABKT groups. Secondly, overall accuracy was evaluated using the image biomarkers (i.e. CDFs). As shown in Table V, classification using image derived biomarkers has higher accuracy compared to that based on clinical ones. To show the advantages of integrating both clinical and image biomarkers, the kidney status was also assessed using the same LOSO approach and an SNCAE classifier augmented with both biomarkers. As expected, the overall accuracy notably increases after fusion/integration as shown in Table V.

TABLE V

Diagnostic accuracy (ACC), sensitivity (SENS), and specificity (SPEC) for our CAD system with the SNCAE classifier using clinical and image-driven biomarkers.

| | Clinical Biomarkers | | | Image Biomarkers | | | Fused Biomarkers | | |
|---|---|---|---|---|---|---|---|---|---|
| | ACC % | SENS % | SPEC % | ACC % | SENS % | SPEC % | ACC % | SENS % | SPEC % |
| AR vs. DRD | 88.00 | — | — | 93.00 | — | — | 95.00 | — | — |

Note that "AR" and "DRD" stand for acute rejection and different renal disease, respectively.

Following the second SNCAE-based classification stage, the system assesses the AR transplant type with a third-stage SNCAE-based classifier using the constructed CDFs and the clinical biomarkers. A leave-one-subject-out (LOSO) approach is applied to distinguish between TMR from AMR. First, accuracy was evaluated using the clinical biomarkers alone. As demonstrated in Table VI, diagnostic accuracy using the clinical biomarkers only is very low due to the large overlap of these biomarkers between TMR and AMR groups. Secondly, the overall accuracy was evaluated using the image biomarkers (i.e. CDFs). As shown in Table VI, classification using image-derived biomarkers has higher accuracy compared to that based on clinical ones. To show the advantages of integrating both clinical and image biomarkers, the kidney status was also assessed using the same LOSO approach and an SNCAE classifier augmented with both biomarkers. As expected, the overall accuracy notably increases after fusion as shown in Table VI.

TABLE VI

Diagnostic accuracy (ACC), sensitivity (SENS), and specificity (SPEC) for our CAD system with the SNCAE classifier using clinical and image-driven biomarkers.

| | Clinical Biomarkers | | | Image Biomarkers | | | Fused Biomarkers | | |
|---|---|---|---|---|---|---|---|---|---|
| | ACC % | SENS % | SPEC % | ACC % | SENS % | SPEC % | ACC % | SENS % | SPEC % |
| TMR vs. AMR | 70.00 | — | — | 90.00 | — | — | 93.00 | — | — |

Note that "TMR", and "AMR" stand for T-cell and anti-body mediated rejection, respectively.

Table VII displays a comparison of the diagnostic accuracy from the disclosed segmentation method using $4^{th}$ order-MGRF as compared to calculations of ADCs and CDFs for the segmented kidney regions using a previously developed segmentation method using only the $2^{nd}$ order-MGRF spatial interactions and the Chan and Vese (CV) segmentation method. In each case, the constructed CDFs were used to train and test the SNCAE classifier using the same LOSO scenario. Without being bound by theory, the improved accuracy of the instant segmentation technique may result from more accurate and reliable segmentation of the 3D kidneys.

TABLE VII

Diagnostic accuracy for our CAD system for our level-set segmentation-based $4^{th}$ order-MGRF spatial interactions, level-set segmentation-based only $2^{nd}$ order-MGRF spatial interactions, and the level-set approach by CV).
(Diagnostic Accuracy) % Based on Segmentation

| CV [70] | $2^{nd}$ order-MGRF | $4^{th}$ order-MGRF |
|---|---|---|
| 81.00 | 95.00 | 97.0 |

The diagnostic accuracy of process 610 was compared with the current clinical method, which is based on using the clinical biomarkers (i.e. SPCr, in which an average basal level for abnormality of >1.3 mg dl$^{-1}$ is used and CrCl, in which normal values are 88-128 mL/min for healthy women and 97-137 mL/min for healthy men). Significant deviations from the patient's SPCr basal level and CrCl normal range was detected using a LOSO approach along with a k-nearest neighbor (kNN) classifier and was used for abnormality detection and a "for cause" biopsy needs to be performed. An additional method that is currently used in the clinical research by clinicians is to place a 2D ROI on the largest mid cross-section of the kidney, using a certain pair of b-values (e.g., $b_0$ and $b_{1000}$) s/mm$^2$. Next, the average ADC value is calculated from this cross-section for each subject. Then, a LOSO approach is used along with a kNN classifier to find the final diagnosis. Comparison of this method's accuracy with the aforementioned clinical methods is summarized in Table VIII. As documented in Table VIII, this approach shows the superiority over the currently used and well-validated clinical methods by clinicians in hospitals and clinical research.

TABLE VIII

Comparative accuracy of this technique to the standard clinical methods used by physicians. Note that DiagTech, DiagAcc, and SPCr denote diagnostic technique, diagnostic accuracy, and serum plasma creatine, respectively

| DiagTech | Our (3D + b-value) | SPCr | manual 2D-ROI |
|---|---|---|---|
| DiagAcc % | 97.0 | 72.0 | 65.7 |

In order to evaluate the effect of the CDFs encoding step (Δ) on the overall accuracy, we reconstructed the CDFs using two different Δi(Δ=0.02 and 0.04). Then, we applied our SNCAE classifier on the reconstructed CDFs and the results are shown in Table IX. As demonstrated in Table IX, the overall accuracy, sensitivity, and specificity, have been greatly reduced. This can be explained in part by the fact that increasing the value of Δ results in losing important data information, thus making the data not well-presented, which in turn affects the classifier performance.

TABLE IX

Diagnostic accuracy, sensitivity, and specificity for the CAD system with the SNCAE classifier using different CDF encoding steps (Δi).

| | Quality of classification % ≈ | | |
|---|---|---|---|
| Δi | Accuracy | Sensitivity | Specificity |
| Δi = 0.01 | 97 | 96 | 100 |
| Δi = 0.02 | 87 | 87 | 82 |
| Δi = 0.04 | 83 | 87 | 77 |

Furthermore, the effect of changing the SNCAE structure on the overall accuracy has been investigated by using different SNCAE layouts (different number of hidden layers (l) and hidden nodes at each layer (sl)). From the results in Table X, the network structure with two hidden layers s1=50 and s2=5, demonstrated the highest accuracy.

TABLE X

Diagnostic accuracy, sensitivity, and specificity for this CAD system with the SNCAE classifier using different structures, i.e., different number of hidden layers (l) and hidden nodes at each layer ($S_1$), using the same input size of 1100 (11 CDFS each of 100 region),
$a = 3 * 10^{-5}, \beta = 3, \text{ and } \gamma = 0.1.$

| | Quality of classification % ≈ | | |
|---|---|---|---|
| SNCAE Structure: | Accuracy | Sensitivity | Specificity |
| $S_1 = 5$ | 84 | 83 | 88 |
| $S_1 = 25$ | 61 | 66 | 53 |
| $S_1 = 50$ | 69 | 70 | 65 |
| $S_1 = 50$ and $S_2 = 5$ | 97 | 96 | 100 |
| $S_1 = 50$ and $S_2 = 25$, and $S_3 = 5$ | 81 | 95 | 53 |

In addition to the LOSO approach, we have performed a four-fold cross-validation test where 75% of the data was used for training and the other 25% for testing, and a 10-fold cross-validation test where 90% of the data was used for training and the other 10% for testing, to further validate and justify the performance of the developed SNCAE classifier. As documented in Table XI, the diagnostic accuracy of the combined SNCAE classification system is almost independent of the choice of the training and testing data sets. The four-fold and 10-fold cross-validation experiments demonstrated an average accuracy of 96.0% and 94.0%, respectively.

TABLE XI

Sensitivity to a training set based on four-fold and 10-fold cross-validation scenarios.

| | Testing group (25%) | | | |
|---|---|---|---|---|
| | 1 | 2 | 3 | 4 |
| | 4-fold Cross-validating SNCAE | | | |
| Correct/All | 15/16 | 15/16 | 16/17 | 17/17 |
| Average accuracy, % | 95.0 | | | |
| | 10-fold Cross-validating SNCAE | | | |
| Average accuracy, % | 94.0 | | | |

To evaluate capabilities of the developed SNCAE classifier, it has been compared with seven well-known learnable classifiers from the Weka collection: K*, Naïve Bayes Tree (NBT), Multi-Class Classifier (MCC), Decorate, Random Tree (RT), Random Forest (RF), and Support Vector Machine (SVM). Table XII presents their and our diagnostic accuracy in terms of the numbers of correctly classified ABKT and NKT cases with respect to the overall numbers of subjects, sensitivity, specificity, and area under the curve (AUC). The instant classifier demonstrated the best total diagnostic accuracy of 97% with 100% specificity (16 out of 16 correctly classified NKT transplants), and 96% sensitivity (48 out of 50 correctly classified ABKT transplants). In addition, the SNCAE demonstrated the highest AUC (approaches the top-most unit value). These initial diagnostic results confirm that the proposed system holds promises as a reliable non-invasive diagnostic tool. To better compare with the instant classifier, all other classifiers were tuned several times until best accuracies were obtained.

TABLE XII

Diagnostic results in terms of correctly classified vs. true normal (NKT) and abnormal (ABKT) kidney transplants cases, accuracy, sensitivity, specificity, and AUC for the instant CAD system with our SNCAE classifier and seven classifiers from the Weka collection.

| | | | Classification Accuracy % ≈ | | | |
|---|---|---|---|---|---|---|
| | NR | AR | Accuracy | Sensitivity | Specificity | AUC |
| K* | 12/16 | 40/50 | 79 | 80 | 75 | 0.81 |
| NBT | 11/16 | 43/50 | 82 | 86 | 69 | 0.81 |
| MCC | 15/16 | 46/50 | 92 | 92 | 94 | 0.92 |
| Decorate | 8/16 | 44/50 | 79 | 88 | 50 | 0.81 |
| RT | 10/16 | 40/50 | 76 | 80 | 63 | 0.74 |
| RF | 10/16 | 46/50 | 85 | 92 | 63 | 0.83 |
| SVM | 12/16 | 47/50 | 89 | 94 | 75 | 0.87 |
| SNCAE | 16/16 | 48/50 | 97 | 96 | 100 | 0.96 |

Clinical value of the contributions: Preliminary diagnostic results outlined here have shown that the process 610 can differentiate the normal and abnormal kidney transplants, as well as has the ability to differentiate renal rejection from different renal disease, such as acute tubular necrosis, acute tubular injury, graft amyloidosis, and tubular inflammation. Moreover, the process 610 has shown the ability in discriminating different types of renal rejection such as T-cell and anti-body mediated rejection with a high diag system provides fast diagnostic results (in approximately 20 minutes with this MATLAB version) compared to a week or more turnaround for the final diagnostic biopsy results. These abilities of the process 610 will help clinicians to initiate timely interventions with appropriate treatments. Thus, the process 610 can improve the delivery of healthcare in the USA and worldwide as a new and relatively inexpensive diagnostic tool for early assessment of renal transplant status.

To conclude, the disclosed system for early evaluation of renal transplant status from multi-modality MRI data provides new techniques for non-rigid image alignment, kidney segmentation with a deformable boundary, estimation of spatial perfusion/diffusion and relaxation parameters (e.g., PIs/ADCs, and R2* maps), and classification of the transplanted kidney status using the fusion/integration of these estimated image-markers with the clinical/laboratory biomarkers as integral status descriptions and a trainable SNCAE classifier.

Various aspects of different embodiments of the present invention are expressed in paragraphs X1, X2, and X3 as follows:

X1. One aspect of the present invention pertains to a method for classifying a kidney, the method comprising receiving image data associated with an abdomen scan that includes image data of a kidney; receiving at least one clinical biomarker; segmenting, with at least one processor of a computer, kidney image data associated with the kidney from other image data of the abdomen scan; and classifying the functionality of the kidney by analyzing at least one feature determined from the kidney image data and the at least one clinical biomarker.

X2. Another aspect of the present invention pertains to a system, comprising at least one data processor; at least one memory; and program code stored on the at least one memory and configured to be executed by the at least one processor to cause the at least one processor to receive image data associated with an abdomen scan that includes image data of a kidney, receive at least one clinical biomarker, segment, with at least one processor of a computer, kidney image data associated with the kidney from other image data of the abdomen scan, and classify the functionality of the kidney by analyzing at least one feature determined from the kidney image data and the at least one clinical biomarker.

X3. A further aspect of the present invention pertains to a computer program product comprising a non-transitory computer readable medium; and program code stored on the computer readable medium and configured upon execution by at least one processor to cause the at least one processor to receive image data associated with an abdomen scan that includes image data of a kidney, receive at least one clinical biomarker, segment, with at least one processor of a computer, kidney image data associated with the kidney from other image data of the abdomen scan, and classify the functionality of the kidney by analyzing at least one feature determined from the kidney image data and the at least one clinical biomarker.

Yet other embodiments pertain to any of the previous statements X1, X2, or X3 in combination with one or more of the following other aspects:

Wherein the image data includes image data derived from a plurality of imaging techniques.

Wherein segmenting kidney image data includes registering, with the at least one processor, at least one iso-contour of the kidney image data.

Wherein registering at least one iso-contour of the kidney image data includes identifying the at least one iso-contour of the kidney image data to determine corresponding contours in each of a plurality of time slices of the kidney image data to thereby compensate for kidney motion across the plurality of time slices of the kidney image data.

Wherein segmenting kidney image data is based at least in part on a weighted probabilistic shape associated with the kidney and uses a four level joint Markov-Gibbs random field probabilistic model associated with the kidney.

Wherein classifying the functionality of the kidney includes classifying the kidney as one of an abnormal transplant or a normal transplant by analyzing the at least one clinical biomarker and at least one feature determined from the kidney image data using a learned model.

Wherein a non-negativity constraint is applied to the learned model.

Further comprising classifying the abnormal transplant as acute rejection or different renal disease by analyzing the at least one clinical biomarker and at least one feature determined from the kidney image data using the learned model.

Further comprising classifying the acute rejection as T-cell mediated-rejection (TMR) or anti-body mediated-rejection (AMR) by analyzing the at least one clinical biomarker and at least one feature determined from the kidney image data using the learned model.

Wherein the at least one feature includes perfusion values, and wherein the method further comprises determining the perfusion values based at least in part on the kidney image data.

Wherein the at least one feature includes apparent relaxation rate values, and wherein the method further comprises determining the apparent relaxation rate values based at least in part on the kidney image data.

Wherein the at least one feature includes apparent diffusion coefficient values, and wherein the method further comprises determining the apparent diffusion coefficient values based at least in part on the kidney image data.

Wherein the kidney image data includes a time series of images.

Wherein the image data includes MRI image data.

Wherein the image data includes at least one of DW-MRI, DCE-MRI, and BOLD-MRI image data.

Wherein the image data includes at least two of DW-MRI, DCE-MRI, and BOLD-MRI image data.

Wherein the image data includes DW-MRI, DCE-MRI, and BOLD-MRI image data.

Wherein the at least one clinical biomarker includes at least one of creatinine clearance (CrCl) and serum plasma creatinine (SPCr).

Wherein the at least one clinical biomarker includes creatinine clearance (CrCl) and serum plasma creatinine (SPCr).

Wherein classifying the functionality of the kidney includes classifying the kidney as one of an abnormal transplant or a normal transplant by analyzing the at least one clinical biomarker and at least one feature determined from the kidney image data using a learned model.

Wherein the at least one feature includes at least one of perfusion values, apparent relaxation rate values, and apparent diffusion coefficient values.

Wherein the program code is configured upon execution by the at least one processor to cause the at least one processor to classify the functionality of the kidney as one of an abnormal transplant or a normal transplant by analyzing the at least one clinical biomarker and at least one feature determined from the kidney image data using a learned model.

Wherein the program code is configured upon execution by the at least one processor to cause the at least one processor to classify the functionality of the kidney as one of an abnormal transplant or a normal transplant, and to classify any abnormal transplant as one of an acute rejection or a different renal disease by analyzing the at least one clinical biomarker and at least one feature determined from the kidney image data using a learned model.

Wherein the program code is configured upon execution by the at least one processor to cause the at least one processor to classify the functionality of the kidney as one of an abnormal transplant or a normal transplant, and to classify any abnormal transplant as one of an acute rejection or a different renal disease, and to classify any acute rejection as T-cell mediated-rejection (TMR) or anti-body mediated-rejection (AMR) by analyzing the at least one clinical biomarker and at least one feature determined from the kidney image data using a learned model.

The foregoing detailed description is given primarily for clearness of understanding and no unnecessary limitations are to be understood therefrom for modifications can be made by those skilled in the art upon reading this disclosure and may be made without departing from the spirit of the invention.

What is claimed is:

1. A method for classifying a kidney, the method comprising:
receiving image data associated with an abdomen scan that includes image data of a kidney;
receiving at least one clinical biomarker;
segmenting, with at least one processor of a computer, kidney image data associated with the kidney from other image data of the abdomen scan; and
classifying the functionality of the kidney by analyzing at least one feature determined from the kidney image data and the at least one clinical biomarker;
wherein segmenting kidney image data is based at least in part on a weighted probabilistic shape prior associated with the kidney, the weighted probabilistic shape prior based on a training set of kidney image data, and based at least in part on a Markov-Gibbs random field probabilistic model associated with the kidney.

2. The method of claim 1, wherein the image data includes image data derived from a plurality of imaging techniques.

3. The method of claim 1, wherein segmenting kidney image data includes registering, with the at least one processor, at least one iso-contour of the kidney image data.

4. The method of claim 3, wherein registering at least one iso-contour of the kidney image data includes identifying the at least one iso-contour of the kidney image data to determine corresponding contours in each of a plurality of time slices of the kidney image data to thereby compensate for kidney motion across the plurality of time slices of the kidney image data.

5. The method of claim 1, wherein the Markov-Gibbs random field probabilistic model associated with the kidney is a four level joint Markov-Gibbs random field probabilistic model associated with the kidney.

6. The system of claim 5, wherein the at least one feature includes at least one of perfusion values, apparent relaxation rate values, and apparent diffusion coefficient values.

7. The method of claim 1, wherein classifying the functionality of the kidney includes classifying the kidney as one of an abnormal transplant or a normal transplant by analyzing the at least one clinical biomarker and at least one feature determined from the kidney image data using a learned model.

8. The method of claim 7, wherein a non-negativity constraint is applied to the learned model.

9. The method of claim 7, further comprising classifying the abnormal transplant as acute rejection or different renal disease by analyzing the at least one clinical biomarker and at least one feature determined from the kidney image data using the learned model.

10. The method of claim 1, wherein the at least one feature includes perfusion values, and wherein the method further comprises determining the perfusion values based at least in part on the kidney image data.

11. The method of claim 1, wherein the at least one feature includes apparent relaxation rate values, and wherein the method further comprises determining the apparent relaxation rate values based at least in part on the kidney image data.

12. The method of claim 11, wherein determining the apparent relaxation rate values based at least in part on the kidney image data comprises determining the apparent relaxation rate values based at least in part on kidney image data derived from blood oxygen level dependent magnetic resonance imaging (BOLD-MRI).

13. The method of claim 1, wherein the at least one feature includes apparent diffusion coefficient values, and wherein the method further comprises determining the apparent diffusion coefficient values based at least in part on the kidney image data.

14. The method of claim 1, wherein the kidney image data includes a time series of images.

15. The method of claim 1, wherein the at least one clinical biomarker includes at least one of creatinine clearance (CrCl) and serum plasma creatinine (SPCr).

16. The method of claim 1, wherein the image data includes image data derived from blood oxygen level dependent magnetic resonance imaging (BOLD-MRI) and at least one of diffusion-weighted magnetic resonance imaging (DW-MRI) and dynamic contrast-enhanced magnetic resonance imaging (DCE-MRI).

17. The method of claim 16,
wherein the image data is derived from a patient having a glomerular filtration rate;
wherein the image data includes image data derived from DCE-MRI when the glomerular filtration rate is >30 ml/min; and
wherein the image data includes image data derived from DW-MRI when the glomerular filtration rate ≤30 ml/min.

18. A method for classifying a kidney, the method comprising:
receiving image data associated with an abdomen scan that includes image data of a kidney;
receiving at least one clinical biomarker;
segmenting, with at least one processor of a computer, kidney image data associated with the kidney from other image data of the abdomen scan; and
classifying the functionality of the kidney by analyzing at least one feature determined from the kidney image data and the at least one clinical biomarker;
wherein classifying the functionality of the kidney includes classifying the kidney as one of an abnormal transplant or a normal transplant by analyzing the at least one clinical biomarker and at least one feature determined from the kidney image data using a learned model;
further comprising classifying the abnormal transplant as acute rejection or different renal disease by analyzing the at least one clinical biomarker and at least one feature determined from the kidney image data using the learned model;
further comprising classifying the acute rejection as T-cell mediated-rejection (TMR) or anti-body mediated-rejection (AMR) by analyzing the at least one clinical biomarker and at least one feature determined from the kidney image data using the learned model.

19. A system, comprising:
at least one data processor;
at least one memory; and
program code stored on the at least one memory and configured to be executed by the at least one processor to cause the at least one processor to:
receive image data associated with an abdomen scan that includes image data of a kidney;
receive at least one clinical biomarker;
segment, with at least one processor of a computer, kidney image data associated with the kidney from other image data of the abdomen scan based at least in part on a weighted probabilistic shape prior associated with the kidney, the weighted probabilistic shape prior based on a training set of kidney image data, and based at least in part on a Markov-Gibbs random field probabilistic model associated with the kidney; and
classify the functionality of the kidney by analyzing at least one feature determined from the kidney image data and the at least one clinical biomarker.

20. The system of claim 19, wherein classifying the functionality of the kidney includes classifying the kidney as one of an abnormal transplant or a normal transplant by analyzing the at least one clinical biomarker and at least one feature determined from the kidney image data using a learned model.

21. A computer program product comprising:
a non-transitory computer readable medium; and
program code stored on the computer readable medium and configured upon execution by at least one processor to cause the at least one processor to:
receive image data associated with an abdomen scan that includes image data of a kidney;
receive at least one clinical biomarker;
segment, with at least one processor of a computer, kidney image data associated with the kidney from other image data of the abdomen scan based at least in part on a weighted probabilistic shape associated with the kidney, the weighted probabilistic shape prior based on a training set of kidney image data, and based at least in part on a Markov-Gibbs random field probabilistic model associated with the kidney; and
classify the functionality of the kidney by analyzing at least one feature determined from the kidney image data and the at least one clinical biomarker.

22. The computer program product of claim 21, wherein the program code is configured upon execution by the at least one processor to cause the at least one processor to classify the functionality of the kidney as one of an abnormal transplant or a normal transplant, and to classify any abnormal transplant as one of an acute rejection or a different renal disease by analyzing the at least one clinical biomarker and at least one feature determined from the kidney image data using a learned model.

23. The computer program product of claim 21, wherein the at least one feature includes at least one of perfusion values, apparent relaxation rate values, and apparent diffusion coefficient values.

* * * * *